US009351971B2

(12) United States Patent
Cardone et al.

(10) Patent No.: US 9,351,971 B2
(45) Date of Patent: *May 31, 2016

(54) SUBSTITUTED 2,2'-BIPHENAZINES FOR TREATING DISEASES

(71) Applicant: Eutropics Pharmaceuticals, Inc., Cambridge, MA (US)

(72) Inventors: Michael H. Cardone, Dorchester, MA (US); Xiang Y. Yu, Acton, MA (US); Andrew F. Kolodziej, Winchester, MA (US)

(73) Assignee: Eutropics Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,263

(22) Filed: Feb. 17, 2015

(65) Prior Publication Data
US 2015/0216862 A1 Aug. 6, 2015

Related U.S. Application Data

(62) Division of application No. 13/335,287, filed on Dec. 22, 2011, now Pat. No. 8,987,271.

(60) Provisional application No. 61/425,909, filed on Dec. 22, 2010.

(51) Int. Cl.
C07D 241/46 (2006.01)
A61K 31/498 (2006.01)
C07C 217/92 (2006.01)
C07C 229/18 (2006.01)
C07C 229/34 (2006.01)
C07C 229/36 (2006.01)
C07C 229/48 (2006.01)
(Continued)

(52) U.S. Cl.
CPC ............ A61K 31/498 (2013.01); A61K 31/454 (2013.01); A61K 31/573 (2013.01); A61K 31/69 (2013.01); A61K 45/06 (2013.01); C07C 217/92 (2013.01); C07C 229/18 (2013.01); C07C 229/34 (2013.01); C07C 229/36 (2013.01); C07C 229/48 (2013.01); C07C 229/58 (2013.01); C07C 229/60 (2013.01); C07C 229/64 (2013.01); C07C 311/21 (2013.01); C07C 317/36 (2013.01); C07C 317/44 (2013.01); C07D 209/08 (2013.01); C07D 209/34 (2013.01); C07D 211/46 (2013.01); C07D 211/60 (2013.01); C07D 213/79 (2013.01); C07D 215/48 (2013.01); C07D 231/14 (2013.01); C07D 231/38 (2013.01); C07D 235/26 (2013.01); C07D 239/28 (2013.01); C07D 239/42 (2013.01); C07D 241/46 (2013.01); C07D 261/18 (2013.01); C07D 263/34 (2013.01); C07D 263/48 (2013.01); C07D 309/14 (2013.01); C07C 2101/08 (2013.01); C07C 2101/14 (2013.01)

(58) Field of Classification Search
CPC ..................................................... C07D 241/46
USPC ......................................................... 544/347
See application file for complete search history.

(56) References Cited

U.S. PATENT DOCUMENTS 6,242,602 B1  6/2001 Giri et al.
6,387,902 B1  5/2002 Zhang et al.
(Continued)

FOREIGN PATENT DOCUMENTS

ES      2130992 A1     7/1999
JP      2007-142308    6/2007
WO      WO 2012-088438 6/2012

OTHER PUBLICATIONS

Hackam, et al. JAMA, 296(14), 2006, 1731-1732.*
(Continued)

Primary Examiner — Douglas M Willis
(74) Attorney, Agent, or Firm — Cooley LLP; J. Dean Farmer; Fraser D. Brown

(57) ABSTRACT

The invention relates to a chemotherapeutic cancer treatment in which compounds (BH3Is) are administered to a mammal to treat B-cell Lymphoma or other hematopoietic cancers, including diseases associated with MCL-1. The invention also provides a method for treating types of hematopoietic cancers, such as B-cell lymphoma, using a combination of one or more disclosed compounds in combination with other therapes, for example, 26S proteasome inhibitors, such as, for example, Bortezomib. The invention also relates to autoimmune treatment with pharmaceutical compositions comprising one or more disclosed compounds. The invention also relates to methods for identifying compounds, for example, compounds of the BH3 mimic class, that have unique in vitro properties that predict in vivo efficacy against B-cell lymphoma tumors and other cancers as well as autoimmune disease.

Illustrative compounds are those of Formula II:

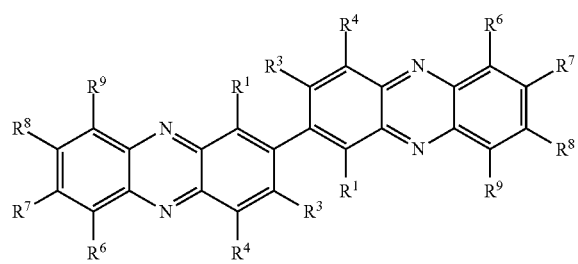

20 Claims, 16 Drawing Sheets

(51) Int. Cl.

| | |
|---|---|
| C07C 229/58 | (2006.01) |
| C07C 229/60 | (2006.01) |
| C07C 229/64 | (2006.01) |
| C07C 311/21 | (2006.01) |
| C07C 317/36 | (2006.01) |
| C07C 317/44 | (2006.01) |
| C07D 209/08 | (2006.01) |
| C07D 209/34 | (2006.01) |
| C07D 211/46 | (2006.01) |
| C07D 211/60 | (2006.01) |
| C07D 213/79 | (2006.01) |
| C07D 215/48 | (2006.01) |
| C07D 231/14 | (2006.01) |
| C07D 231/38 | (2006.01) |
| C07D 235/26 | (2006.01) |
| C07D 239/28 | (2006.01) |
| C07D 239/42 | (2006.01) |
| C07D 261/18 | (2006.01) |
| C07D 263/34 | (2006.01) |
| C07D 263/48 | (2006.01) |
| C07D 309/14 | (2006.01) |
| A61K 31/454 | (2006.01) |
| A61K 31/573 | (2006.01) |
| A61K 31/69 | (2006.01) |
| A61K 45/06 | (2006.01) |

(56) References Cited

U.S. PATENT DOCUMENTS

| | | |
|---|---|---|
| 8,987,271 B2 | 3/2015 | Cardone et al. |
| 2008/0044379 A1 | 2/2008 | Bachand et al. |
| 2009/0203050 A1 | 8/2009 | Bonavida et al. |
| 2009/0264382 A1 | 10/2009 | Chaplin et al. |
| 2010/0086544 A1 | 4/2010 | Mass et al. |

OTHER PUBLICATIONS

Gordienko et al., "Polarography and IR spectra of 2,2'-biphenazinyl and its derivatives," Elektrohimia 7(12):1830-1833 (1971).

Guirado et al., "One-Pot Synthesis of 1,4-Dichlorophenazines," Tetrahedron 53(17):6183-6194 (1997).

International Preliminary Report on Patentability for International Application No. PCT/US2011/066888, dated Jun. 25, 2013, 5 pages.

International Search Report for International Application No. PCT/US2011/066888, dated Jun. 28, 2012, 3 pages.

Jordan, "Tamoxifen: A Most Unlikely Pioneering Medicine," Nature Reviews: Drug Discovery 2:205-213 (2003).

Musso and Rathjen, "Die Autoxydationprodukte des 2.5-Dimethylresorcins in Ammoniak und Kalilauge," Chemische Berichte 96(6):1593-1609 (1963).

Musso, Synthese, Konstitution und Lichtabsorption des Henrichschen Chinons, Chemische Berichte 91:349-363 (1958).

Supplementary Partial European Search Report, EP 11851853.9, 8 pages (Dec. 1, 2014).

Vippagunta et al., "Crystalline solids," Adv. Drug Deliv. Rev. 48:3-26 (2001).

Written Opinion for International Application No. PCT/US2011/066888, dated Jun. 22, 2012, 4 pages.

* cited by examiner

Fluorescence Polarization Assay showing activity of compound A against Mcl-1 and Bcl-xL

Fluorescence Polarization Assay showing activity of compound II-19 against Mcl-1 and Bcl-xL

Myeloid tumor NCI-H929 cell killing by treatment with compound A

Haematological cancer cell killing by treatment with compound II-19

NCI-H929 Cell Line Treated with Compound II-19

SUDHL-6 Lymphoma Cells Treated with Compound II-19

SUDHL-10 Lymphoma Cells Treated with Compound II-19

NCI-H929 and SUDHL-10 Cell Lines Treated with Obatoclax

Response to compound A in Bax-Bak-functional mitochondria indicating on-target activity

Non-response to compound A in Bax-Bak deficient mitochondria indicating on-target and selective activity

Response of mitochondria in semi-permeablized lymphoid cell lines to II-19.

Pharmacokinetic profile of compound II-19 in mouse plasma

Average tumor volume over time of SCID Mice in a Myeloma (NCI-H929) Xenograft Model treated with compound II-19, Bortezomib, or vehicle

US 9,351,971 B2

SUBSTITUTED 2,2'-BIPHENAZINES FOR TREATING DISEASES

RELATED APPLICATIONS

This application is a divisional of non-Provisional application Ser. No. 13/335,287, filed Dec. 22, 2011, and claims the benefit of Provisional Application 61/425,909, filed Dec. 22, 2010, all of which are incorporated herein in their entirety for all purposes.

GOVERNMENT SUPPORT

Research leading to this invention was in part funded by SBIR grant number R44 CA135915-02 from the National Cancer Institute, National Institutes of Health, Bethesda, Md.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: EUTR_006_03US_SeqList_ST25.txt, date recorded: Feb. 17, 2015, file size 747 bytes).

FIELD OF THE INVENTION

This invention relates generally to compositions and methods for treating cancer and autoimmune diseases. This cancer may be hematological malignancies, such as Multiple Myeloma, B-cell lymphoma, and more specifically, the invention relates to treating autoimmune diseases and cancers, including hematological malignancies, with one or more compounds that inhibit the Bcl-2 family of protein Mcl-1 as well as other of the Bcl-2 family proteins. In addition, this invention relates to methods for determining selectivity of these newly classified "BH3 mimic" compounds to predict efficacy in treating hematological and other malignancies involving Mcl-1. All patents, patent applications, and publications cited herein are hereby incorporated by reference in their entireties.

BACKGROUND

Currently the prevalence of Multiple Myeloma (MM) is 63,000 people in the US with about 13,000 cases per year. There are 360,000 cases of non-Hodgkin's lymphoma (NHL) in the United States and 550,000 worldwide, with about 56,000 cases diagnosed per annum and 23,000 deaths per annum (American Cancer Society, The SEER Cancer Statistics Review (CSR) web site, http://seer, cancer.gov/esr/1975_2002/). Twenty percent of these do not respond to current therapy, In terms of all NHL cases. 60% are aggressive, of which 50% do not respond to from line therapy. In addition, chronic lymphocytic leukemia (CLL) is the most common form of adult leukemia in the U.S. and in most of Western Europe. There are approximately 70,000 cases of CLL in the U.S., with 10,000 new eases diagnosed per annum (www.cancer.gov/cancertopics/types/leukemia). CLL patients have a poor survival prognosis with a five-year survival rate of 46%.

Mcl-1 is a key regulator of lymphoid cancers including multiple-myeloma (MM) (Zhang B et al. (2002), Blood 99: 1885-1893), non-Hodgkin's lymphomas (Cho-Vega J H et. al (2004) Hum. Pathol. 35(9); 1095-100) and chronic lymphocytic leukemia (CLL) (Michaels J, et. al (2004), Oncogene 23:4818-4827). Additionally, treatment of myeloma cells with the proteosome inhibitor Bortezomib (Velcade) has been shown to cause elevated Mcl-1 expression (Nencioni A, et al. (2005) Blood; 105(8):3255-62) and this is seen in some myeloma patients (Podar K et al (2008) Oncogene 27(6); 721-31). It is proposed that an Mcl-1 inhibitor would enhance the efficacy of Velcade treatment in MM patients.

Though Rituxan, which targets B-cell surface protein CD-20, has proven to be a valuable front line therapeutic for many NHL and CLL patients, resistance to this drug has been, shown to correlate with elevated expression of B-cell lymphoma 2 (Bcl-2) or Myeloid Cell factor-1 (Mcl-1) proteins (Hanada et al. (1993) Blood 82: 1820-28; Bannerji et al. (2003) J. Clin. Oncol 21(8): 1466-71). Notably, there is a high correlation of elevated Mel-1 with non-responsiveness to chemotherapies in B-cells from CLL patients. (Kitada et al (2002) Oncogene 21: 3450-74). Rituxan-resistant CLL cells also have a higher Mcl-1/Bax ratio than normal cells, while there is no significant correlation of the Bcl2/Bax ratio, (Bannerji et al. (2003) supra).

Moreover, approximately 30% of diffuse large cell lymphomas (DLCLs) have increased Bcl-2 expression levels. This con-elates with poor patient response to treatment with combination, chemotherapy (Mourner et al (2003) Blood 101: 4279-84). In follicular non-Hodgkin's lymphomas and plasms cell myeloma, Mcl-1 expression positively correlates with increasing grade of the disease (Cho-Vega et al. (2004) Hum, Pathol. 35(9): 1095-100).

The value of Bcl-2 as a target in anti-tumor therapy has been well established. The literature also reports on Mel-1 as a target in treating NHL, CLL, and acute myiogenous leukemia (AML) (Derenne et al. (2002) Blood, 100: 194-99; Kitada et al. (2004) J. Nat. Cane, Inst. 96; 642-43; Petlickovski et al. (2005) Blood 105: 4820-28). Researchers nave recognized that proteins in the Bcl-2 family regulate apopiosis and are key effectors of tumorigenesis (Reed (2002) Nat Rev. Drug Discov. 1(2): 111-21). Bcl-2 promotes cell survival, and normal cell growth and is expressed hi many types of cells including lymphocytes, neurons and self-renewing cells, such as basal epithelial cells and hematopoietic progenitor cells in the bone marrow.

In many cancers, anti-apoptotic Bcl-2 proteins, such as Bcl-2 and Mcl-1, unfortunately block the sensitivity of tumor cells to cytostatic or apoptosis inducing drugs. These proteins are therefore targets for anti-tumor therapy. A recently described class of small molecules that inhibit Bcl-2 family proteins are the BH3 mimetic compounds (Nat. Reviews Drug Discovery vol 4:399-409). these compounds function by inhibiting BH3 mediated protein/protein interactions among the Bcl-2 family proteins. Several studies have described BH3 mimetic small molecules that function as Bcl-2 inhibitors by blocking BH3 binding (reviewed in Reed, et al. (2005) Blood 106: 408-418). Compounds with BH3 mimic function include HA-14-1 (Wang et al. (2000) Proc. Natl. Acad. Sci. USA 97: 7124-9, Antimycin-A (Tzung et al. (2001) Nat. Cell. Biol. 3: 183-191), BH3I-1 and BH3I-2 (Degterev et al. (2001) Nat. Cell. Biol. 3:173-82), and seven un-amed compounds (Enyedy et al. (2001) J. Med Chem 44: 4313-24), as well as a series of terphenyl derivatives (Kutzki et al. (2002) J. Am. Chem. Soc. 124: 11838-9), and two new classes of molecules (Rosenberg et al. (2004) Anal. Biochem. (2004) 328: 131-8). More recently, a BH3 mimic compound has been tested in a mouse tumor model (Oltersdorf et al. (2005) Nature 435(7042): 677-81).

The promise for using BH3 mimetic compounds as anti-tumor therapeutics has been recognised, and is described in the literature; however, to date there are no conclusive reports from, the clinic on the efficacy of any anti-cancer drags with this mode of action. While pharmacological manipulation of the Bcl-2. family proteins is a feasible approach to achieving therapeutic benefit for cancer patients, the complexity of the network of proteins that comprise this family makes this prospect difficult. Therefore, with the large unmet medical need for treating hematological malignancies, new approaches to assessing and utilising the detailed activity of the BH3 mimic molecules will, have value in developing this class of therapeutics.

SUMMARY OF THE INVENTION

The present invention is directed to compositions and methods useful for treating cancer and autoimmune diseases.

There is provided in accordance with one aspect of the invention, compounds of Formula Ia:

$$Ar_1\text{-}L_1\text{-}Ar_2\text{-}L_2\text{-}Ar_3\text{-}L_3\text{-}Ar_4 \qquad \text{Formula Ia}$$

and stereoisomers, tautomers, solvates, and pharamceutically acceptable salts, thereof, wherein:

$Ar_1$, $Ar_2$, $Ar_3$, and $Ar_4$ are each independently null, $C_{6-10}$ aryl, $C_{6-10}$ heteroaryl, $C_{5-10}$ membered heterocycl, $C_5\text{-}C_{10}$ cycloalkyl, $C_5\text{-}C_{10}$ heterocycle, $C_1\text{-}C_6$ straight, or branched alkyl, each of which is optionally substituted with one or more substituents $R^s$;

$L_1$, $L_2$, and $L_3$ are each independently a covalent bond, or a saturated or unsaturated $C_{1-3}$ carbon chain, or a branched or unbranched $C_{1-3}$ carbon chain, wherein one or more methylene groups are optionally independently replaced by heteroatoms chosen from O, NR and $S(O)_m$; and wherein L is optionally substituted with 0-2 oxo-groups and one or more $C_{1-4}$ branched or unbranched alkyl optionally substituted by one or more F, Cl, Br, I, cyano, —C(O)R, C(O)NR$_2$, C(O)OR, OR, NR$_2$, SiR$_3$, —S(O)$_m$R, each R is independently hydrogen, or linear or cyclic $C_{1-6}$ alkyl, branched or unbranched $C_{1-6}$ alkyl, or saturated or unsaturate $C_{1-6}$ alkyl;

each m is independently 0, 1 or 2;

each $R^s$ is independently F, Cl, Br, I, cyano —C(O)R, C(O)NR$_2$, C(O)OR, OR, NR$_2$, SiR$_3$, —S(O)$_m$R, substituted or unsubstituted straight, or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted saturated, or unsaturated 3-11 member heterocyclyl or heteroeyclylalkyl containing 1, 2, 3, or 4 heteroatoms selected independently from N, O, $S(O)_m$;

provided that the compound of Formula Ia is not 2,2'-(3,3'-dimethoxybiphenyl-4,4'-diyl)bis(azanediyl)dibenzoic acid or N4,N4'-bis(1-iminoisoindolin-5-yl)biphenyl-4,4'-diamine. diamine.

In another aspect, there is provided compounds of Formula Ib:

Formula Ib

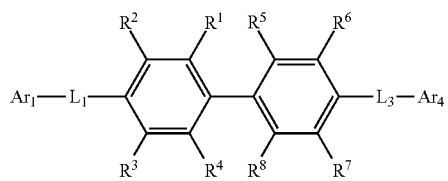

and stereoisomers, tautomers, solvates, and pharmaceutically acceptable salts, thereof, wherein:

$Ar_1$ and $Ar_4$ are each independently null, $C_{6-10}$ aryl, $C_{6-10}$ heteroaryl, $C_{5-10}$ heterocycle, $C_5\text{-}C_{10}$ cycloalkyl, $C_5\text{-}C_{10}$ heterocycle, each of which is optionally substituted with one or more substituents $R_1$, $R^2$, $R^3$, $R^4$, $R^5$, $R^6$, $R^7$, and $R^8$;

$L_1$ and $L_3$ are each independently a covalent bond, or a saturated or unsaturated $C_{1-3}$ carbon chain, or a branched or unbranched $C_{1-3}$ carbon chain, wherein one or more methylene groups are optionally independently replaced, by O, MR or $S(O)_m$; and wherein $L_1$ and $L_3$ are optionally substituted with 0-2 oxo groups and one or more $C_{1-4}$ branched or unbranched alkyl optionally substituted by one or more F, Cl, Br, I, cyano, —C(O)R, C(O)NR$_2$, C(O)OR, OR, NR$_2$, SiR$_3$, —S(O)$_m$R, each R is independently hydrogen, or linear or cyclic $C_{1-6}$ alkyl, branched or unbranched $C_{1-6}$ alkyl, or saturated or unsaturate $C_{1-6}$ alkyl;

each m is independently 0, 1 or 2;

each $R^1$, $R^2$, $R^3$, $R^4$, $R^5$, $R^6$, $R^7$, and $R^8$ is independently F, Cl, Br, I, cyano, —C(O)R, C(O)NR$_2$, C(O)OR, OR, NR$_2$, SiR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubatituted $C_{5-8}$ cycloalkenyl, substituted or unsubstituted $C_{7-20}$ alkyl, substituted or unsubstituted saturated or unsaturated 3-11 member heterocyclyl or heterocyclylalkyl, containing 1, 2, 3, or 4 heteroatoms selected independently from N, O, $S(O)_m$;

provided, that the compound, of Formula Ib is not 2,2'-(3,3'dimethoxybiphenyl-4,4'-diyl)bis(azanediyl)dibenzoic acid, and $Ar_1$ and $Ar_4$ are not simultaneoulsy isoindolin-1'-imine.

In another apsect, there is provided compounds, of Formula Ic;

Formula Ic

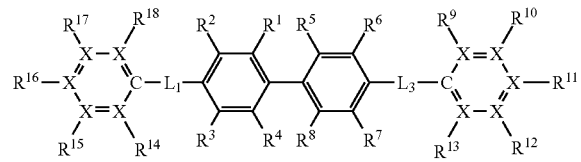

and stereoisomers, tautomers, solvates, and pharmaceutically acceptable salts, thereof, wherein:

each X is independently selected from N or C to form a phenyl, pyridyl, pyrazinyl, pyrimidyl, triazinyl, or tetrazinyl moiety;

$L_1$ and $L_3$ are each independently a covalent bond, or a saturated or unsaturated $C_{1-3}$ carbon, chains, or a branched or unbranched $C_{1-3}$ carbon chain, wherein one or more methylene groups are optionally independently replaced by O, NR or $S(O)_m$; and wherein $L_1$ and $L_3$ are optionally substituted with 0-2 oxo groups and one or more $C_{1-4}$ branched or unbranched alkyl optionally substituted by one or more F, Cl, Br, I, cyano, —C(O)R, C(O)NR$_2$, C(O)OR, OR, NR$_2$, SiR$_3$, —S(O)$_m$R, each R is independently hydrogen, or linear or cyclic alkyl, branched or unbranched $C_{1-6}$ alkyl, or saturatred or unsaturate $C_{1-6}$ alkyl;

each m is independently 0, 1 or 2;

each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently F, Cl, Br, I, cyano, —C(O)R, C(O)NR$_2$, C(O)OR, OR, NR$_2$, SIR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted saturated or unsaturated 3-11 member hetetocyclyl or heterocyclylalkyl containing 1, 2, 3, or 4 heteroatoms selected independently from N, O, $S(O)_m$;

provided that the compound of Formula Ic is not 2,2'-(3, 3'-dimethoxybiphenyl-4,4'-diyl)bis(azanediyl)dibenzoic acid; and wherein at least one of $R^9$, $R^{10}$, $R^{11}$, $R^{12}$, $R^{13}$, $R^{14}$, $R^{15}$, $R^{16}$, $R^{17}$, and $R^{18}$ is C(O)OR.

There is provided in accordance with another aspect of the invention, compounds of Formula II:

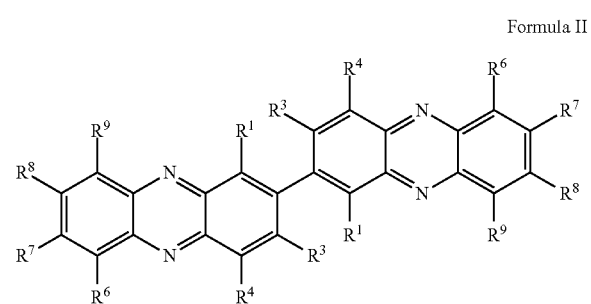

Formula II and stereoisomers, tautomers, solvates, and pharmaceutically acceptable salts, thereof, wherein:

each of $R^1$, $R^3$, $R^4$, $R^6$, $R^7$, $R^8$, and $R^9$ is independently selected from the group consisting of hydrogen, hydroxyl, —($C_1$-$C_6$) alkyl, —($C_1$-$C_6$)alkylhydroxyl, —($C_1$-$C_6$)alkylamino, —($C_1$-$C_6$)alkylamide, —O($C_1$-$C_6$)alkylhalo, —OC(O)($C_1$-$C_6$)alkyl, halo, —C(O)R, —C(O)NR$_2$, and —C(O)OR. Each R is independently selected from the groups consisting of hydrogen, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ arylalkyl, substituted or unsubstituted saturated or unsaturated 3-11 member heterocyclyl or heterocyclylalkyl containing 1, 2, 3, or 4 heteroatoms selected independently from N, O, S.

There is provided in accordance with another aspect of the invention, pharmaceutical compositions comprising a compound of Formula Ia':

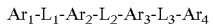

Ar$_1$-L$_1$-Ar$_2$-L$_2$-Ar$_3$-L$_3$-Ar$_4$   Formula Ia' or a stereoisomer, tautomer, solvate, or a pharmaceutically acceptable salt, thereof, wherein:

Ar$_1$, Ar$_2$, Ar$_3$, and Ar$_4$ are each independently null, $C_{6-10}$ aryl, $C_{6-10}$ heteroaryl, $C_{5-10}$ membered heterocycle, $C_5$-$C_{10}$ cycloalkyl, $C_5$-$C_{10}$ heterocycle, $C_1$-$C_6$ straight or branched alkyl, each of which is optionally substituted with one or more substituents $R^s$;

L$_1$, L$_2$, and L$_3$ are each independently a covalent bond, or a saturated or unsaturated $C_{1-3}$ carbon chain, or a branched or unbranched $C_{1-3}$ carbon chain, wherein one or more methylene groups are optionally independently replaced by heteroatoms chosen from O, NR and $S(O)_m$; and wherein L is optionally substituted with 0-2 oxo groups and one or more $C_{1-4}$ branched or unbranched alkyl optionally substituted by one or more F, Cl, Br, I, cyano, —C(O)R, C(O)NR$_2$, C(O)OR, OR, NR$_2$, SiR$_3$, —S(O)$_m$R, each R is independently hydrogen, or linear or cyclic $C_{1-6}$ alkyl, branched or unbranched $C_{1-6}$ alkyl, or saturated or unsaturate $C_{1-6}$ alkyl;

each m is independently 0,1 or 2;

each $R^s$ is independently F, Cl, Br, I, cyano, —C(O)R, C(O)NR$_2$, C(O)OR, Or NR$_2$, SiR$_3$, —S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted saturated or unsaturated 3-11 member heterocyclyl or heterocyclylalkyl containing 1, 2, 3, or 4 heteroatoms selected independently from n, O, $S(O)_m$; and a pharmaceutically acceptable carrier.

There is provided in accordance with another aspect of the invention, pharmaceutical compositions comprising a compound of Formula Ib':

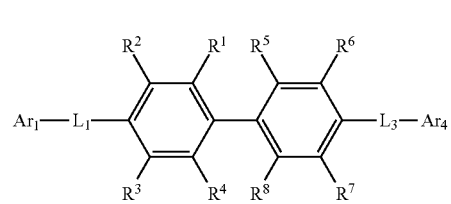

Formula Ib' or a stereoisomer, tautomer, solvate, or a pharmaceutically acceptable salt, thereof, wherein:

Ar$_1$ and Ar$_4$ are each independently null, c$_{6-10}$ aryl, $C_{6-10}$ heteroaryl, $C_{5-10}$ heterocycle, $C_5$-$C_{10}$ cycloalkyl, $C_5$-$C_{10}$ heterocycle, each of which is optionally substituted with one or more substituents $R^1$, $R^2$, $R^3$, $R^4$, $R^5$, $R^6$, $R^7$, and $R^8$;

L$_1$ and L$_3$ are each independently a covalent, bond, or a saturated or unsaturated $C_{1-3}$ carbon chain, or a branched or unbranched $C_{1-3}$ carbon chain, wherein one or more methylene groups are optionally independently replaced by O, NR or $S(O)_m$; and wherein L$_1$ and L$_3$ are optionally substituted with 0-2 oxo groups and one or more $C_{1-4}$ branched or unbranched alkyl optionally substituted by one or more F, Cl, Br, I, cyano, —C(O)R, C(O)NR$_2$, C(O)OR, OR, NR$_2$, SiR$_3$, —S(O)$_m$R, each R is independently hydrogen, or linear or cyclic $C_{1-6}$ alkyl, branched or unbranched $C_{1-6}$ alkyl, or saturated or unsaturate c$_{1-6}$ alkyl;

each m is independently 0, 1 or 2;

each $R^1$, $R^2$, $R^3$, $R^4$, $R^5$, $R^6$, $R^7$, and $R^8$ is independently F, Cl, Br, I, cyano, —C(O)R, C(O)NR$_2$, C(O)OR, OR, NR$_2$, SiR$_3$—S(O)$_m$R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted saturated or unsaturated 3-11 member heterocyclyl or heterocyclylalkyl, containing 1, 2, 3, or 4 heteroatoms selected independently from N, O, $S(O)_m$; and a pharmaceutically acceptable carrier.

There is provided in accordance with another aspect of the invention, pharmaceutical compositions comprising a compound of Formula Ic':

Formula Ic'

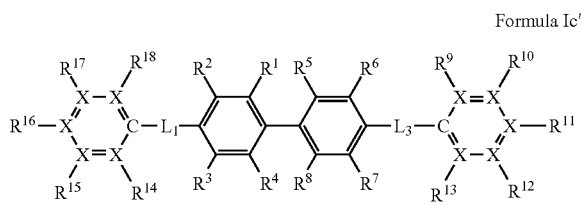

or a stereoisomer, tautomer, solvate, or a pharmaceutically acceptable salt, thereof, wherein;

each X is independently selected from N or C to form a phenyl, pyridyl, pyrazinyl, pyrimidyl, triaxinyl, or tetrainyl moiety;

$L_1$ and $L_3$ are each independently a covalent bond, or a saturated or unsaturated $C_{1-3}$ carbon chain, or a branched or unbranched $c_{1-3}$ carbon chain, wherein one or more methylene groups are optionally independently replaced by O, NR or $S(O)_m$; and wherein $L_1$ and $L_3$ are optionally substituted with 0-2 oxo groups and one or more $C_{1-4}$ branched or unbranched alkyl optionally substituted by one or more F, Cl, Br, I, cyano, —C(O)R, C(O)NR$_2$, C(O)OR, OR, NR$_2$, SiR$_3$, —S(O)$_m$R, each R is independently hydrogen, or linear or cyclic $C_{1-6}$ alkyl, branched or unbranched $C_{1-6}$ alkyl, or saturated or unsaturate $C_{1-6}$ alkyl;

each m is independently 0, 1 or 2;

each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently F, Cl, Br, I, cyano, —C(O)R, C(O)NR$^2$, C(O)OR, OR, NR$_2$, SiR$_3$—S(O)$_m$ R, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ alkyl, substituted or unsubstituted saturated or unsaturated 3-11 member heterocyclyl or heterocyclylalkyl containing 1, 2, 3, or 4 heteroatoms selected independently from N, O, $S(O)_m$; wherein at least one of $R^9$, $R^{10}$, $R^{11}$, $R^{12}$, $R^{13}$, $R^{14}$, $R^{15}$, $R^{16}$, $R^{17}$, and $R^{18}$ is C(O)OR; and a pharmaceutically acceptable carrier.

There is provided in accordance with another aspect of the invention, pharmaceutical compositions comprising a compound of Formula II':

Formula II'

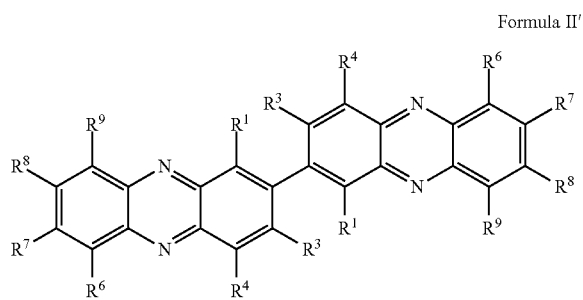

or a stereoisomer, tautorner, solvate, or a pharmaceutically acceptable salt, thereof, wherein:

each of $R^1$, $R^3$, $R^4$, $R^6$, $R^7$, $R^8$, and $R^9$ is independently selected from the groups consisting of hydrogen, hydroxyl, —($C_1$-$C_6$) alkyl, —($C_1$-$C_6$)alkylhydroxyl, —($C_1$-$C_6$)alkylamino, —($C_1$-$C_6$)alkylamide, —O($C_1$-$C_6$)alkylhalo, —OC(O)($C_1$-$C_6$alkyl, halo, —C(O)R, —C(O)NR$_2$, and —C(O)OR. Each R is independently selected from the groups consisting of hydrogen, substituted or unsubstituted straight or branched $C_{1-10}$ alkyl, $C_{2-10}$ alkenyl, or $C_{2-10}$ alkynyl, substituted or unsubstituted $C_{3-10}$ cycloalkyl, substituted or unsubstituted $C_{5-8}$ cycloalkenyl, substituted or unsubstituted $C_{7-20}$ arylalkyl, substituted or unsubstituted saturated or unsaturated 3-11 member heterocyclyl or heterocyclylalkyl containing 1, 2, 3, or 4 heteroatoms selected independently from N, O, S; and a pharmaceutically acceptable carrier.

In another aspect, the invention is directed to methods of treating cancer in patients with pharmaceutical compositions comprising one or more compounds of Formula Ia', Ib', Ic', or II'. This cancer may be a hematological malignancies. Such hematological malignancies include, for example. Multiple Myeloma, B-cell lymphoma, acute myelogenous leukemia, and chronic lymphocytic leukemia. Such treatment results in, for example, tumor regression. Tumor regression can include, for example, killing a cancer cell.

In another aspect, the invention is directed to methods of treating autoimmune diseases in patients with pharmaceutical compositions comprising one or more compounds of Formula Ia', Ib', Ic', or II'. The autoimmune disease may be rheumatoid arthritis, osteo arthritis, psoriatic arthritis, psoriasis, neuromyaotonia, mayasthenia gravis, lupus erythematosus, endometriosis, Graves disease, granulomatosis, Crohns disease, interstitial cystitis, or multiple sclerosis.

A further embodiment of the invention is a method for treating particular types of hematopoietic cancers, using pharmaceutical compositions comprising one or more compounds of Formula Ia', Ib', Ic', or II'. The use of these compounds for particular types of hematopoietic cancers have unexpected results in terms of efficacy and/or ability to inhibit particular anti-apoptotic (pro-survival) members of the Bcl-2 family or to mimic particular members of the pro-apoptotic Bcl-2 family proteins. Accordingly, hematological tumor cells that that arc hyper-dependent on a particular member of the Bcl-2 family of proteins will be most affected by that BH3 mimic which targets that protein, Accordingly, in one aspect the invention, provides a method for killing a cancer cell comprising administering an amount of pharmaceutical compositions comprising one or more compounds of Formula Ia', Ib', Ic', or II' effective to kill a cancer cell of a hematopoietic cancer. The types of hematopoietic cancer include, but are not limited to, Multiple Myeloma, B cell lymphoma, chronic lymphocytic leukemia, and acute myelogenous leukemia.

In another aspect, the invention provides a method for killing a cancer cell comprising administering an amount of pharmaceutical, compositions comprising one or more compounds of Formula Ia', Ib', Ic', or II' in combination with a 26S proteosome inhibitor to kill the cancer cell The types of 26S proteosome inhibitors include, but are not limited to, bortezomib.

In another aspect, the invention provides a method for killing a cancer cell comprising administering an amount of pharmaceutical compositions comprising one or more compounds of Formula Ia', Ib', Ic', or II' in combination with a chemotherapeutic agent that increases the level of Mel-1 in the cancer cell. Such chemotherapeotic agents are 26S proteosome inhibitors and inhibitors of the BB3 domain containing e3 ligase called Mule. Such agents may be, but are not limited to, bortezomib or rituximab.

In another aspect, the invention provides a method for determining whether a candidate compound mimics a ligand specific for a target, the method comprising the steps of (a) providing in a first reaction, the target, a first labeled peptide specific for the target, and a first unlabeled peptide specific for the target, (b) providing in a second, reaction, the target, the first labeled peptide specific for the target, and a first candidate compound, (c) comparing binding specificity of the first unlabeled peptide with binding specificity of the first candidate compound to determine whether the candidate compound mimics the first unlabeled peptide, In certain embodiments, this method further comprises repeating steps (a), (b), and (c) wherein the first labeled peptide specific for the target is replaced with a second labeled peptide specific for the target. In certain embodiments, the target comprises a BH3 domain binding region, such as for example, a hydrophobic pocket formed by the BH1, BH2, BR3 and BH4 domains of the anti-apoptotic Bcl-2 family of proteins.

In another aspect, the invention provides a method for treating particular types of hematopoietic cancers using a compound selected from the group consisting of pharmaceutical compositions comprising one or more compounds of Formula Ia', Ib', Ic', or II'. One or more of these compounds may inhibit the activity of the Bcl-2 family protein Mel-1.

In one embodiment, the compounds of Formula Ia', Ib', Ic', or II' are used in a method for treating particular types of hematopoietic cancers, such as B-cell lymphoma, to preferentially inhibit the binding of a peptide comprised of the BH3 domain of Bak to the Bcl-2 family protein Mcl-1. This activity is unique among all of the reported BH3 mimics and directs the use of this compound in treating certain hematological malignancies that are affected principally by the Bcl-2 family proteins and among those proteins, mostly by Mcl-1. Based on the unique ability of compound A, or B or derivative, to inhibit BH3 binding to Mcl-1, this compound maybe effective in. blocking the unwanted cell survival activity of Mcl-1 in tumorogenic lymphoid and myeloid cells, and therefore may be particularly effective as a therapy for treating Multiple Myeloma (MM), diffuse large B-cell lymphoma (DLBCL), chronic lymphocytic leukemia (CLL), acute myelogenous leukemia (AML), all of which are effected by elevated Mcl-1.

In another aspect, the invention provides a method for treating particular types of hematopoietic cancers using a combination of one or more compounds selected from the group consisting of Formula Ia, Ib, Ic, or II, in combination with other therapies, for example, a class of therapeutics known as 26S proteosome inhibitors, such as, for example, Bortezomib (Velcade®).

In another aspect, the invention provides methods for identifying specific activity of BH3 mimic compounds. For example, these compounds can have varying potencies in inhibiting BH3-mediated binding of particular Bcl-2 family proteins, and the difference in potency can be identified by systematically ordering combinations of protein-protein interactions and comparing the blocking activity of BH3 mimic compounds to that of competing BH3 domain containing peptides. By matching the activity of the compound to a particular BH3 domain peptide, a biological activity can be assigned to that compound that correlates to the activity of the BN3 domain containing protein. This information can be used to predict the utility of a BH3 mimic compounds in treating, a particular disease.

In one aspect, the invention provides an agent, which modulates apoptosis by binding to the Bcl-2 family proteins including Mcl-1 and preferentially blocks BH3 domain binding.

In another aspect, the invention provides a method for using pharmaceutical compositions comprising one or more compounds of Formula Ia', Ib', Ic', or II' as preferential inhibitors of Mcl-1.

In another aspect, the invention provides a method for blocking binding of the BH3-only Bcl-2 family proteins or parts thereof, for example Puma, Noxa, Bim, Bid and Bak, to Mcl-1.

In another aspect, the invention provides a method for using pharmaceutical compositions comprising one or more compounds of Formula Ia', Ib', Ic', or II' as preferential inhibitors of Mcl-1 to induce apoptosis in cells overexpressing Mcl-1.

In another aspect, the invention provides a method for blocking binding of the BH3-only proteins or parts thereof, for example Puma, Noxa, Bim, Bid and Bak, to Mcl-.

In another aspect, the invention provides a method for using specific BH3 mimic compounds of Formula Ia', Ib', Ic', or II' for inhibiting the activity of the Bcl-2 family protein Mcl-1 for the purpose of treating lymphoid malignancies either alone or in combination with, other anti-tumor agents.

In another aspect, the invention provides a method for using specific BH3 mimic compounds or Formula Ia, Ib, Ic, or II for inhibiting the activity of the Bcl-2 family protein Mcl-1 for the purpose of treating myeloid cancer either alone or in combination with other anti-tumor agents.

In another aspect, the invention provides a method for using specific BH3 mimic compounds of Formula Ia', Ib', Ic', or II' for inhibiting the activity of the Bcl-2 family protein Mcl-1 for the purpose of treating prostate cancer cither alone or In combination with other anti-tumor agents.

In another aspect, the invention provides a method for using specific BH3 mimic compounds of Formula Ia', Ib', Ic', or II' for inhibiting the activity of the Bcl-2 family protein Mcl-1 for the purpose of treating non-Hodgkins lymphoma patients who are resistant to Rituxan either alone or in combination with other anti-tumor agents.

In another aspect, the invention provides a method, for using specific BH3 mimic compounds of Formula Ia', Ib', Ic', or II' for inhibiting the activity of the Bcl-2 family protein Mcl-1 for the purpose of treating Chronic Lymphocytic Leukemia patients who are resistant to Rituxan either alone or in combination with, other anti-tumor agents.

In another aspect, the invention provides a method for using specific BH3 mimic compounds of Formula Ia', Ib', Ic', or II' for inhibiting the activity of the Bcl-2 family protein Mcl-1 for the purpose of treating breast cancer either alone or in combination with other anti-tumor agents.

In another aspect, the invention provides a method for using specific BH3 mimic compounds of Formula Ia', Ib', Ic', or II' for inhibiting the activity of the Bcl-2 family protein Mcl-1 for the purpose of treating liver cancer either alone or in combination with other anti-tumor agents.

In another aspect, the invention provides a method for using specific BH3 mimic compounds of Formula Ia', Ib', Ic', or II' for inhibiting the activity of the Bcl-2 family protein. Mcl-1 for the purpose of treating ovarian, cancer either alone or in combination with other anti-tumor agents.

In another aspect, the invention provides a method for treating myelogenous leukemia patients with pharmaceutical compositions comprising one or more compounds of Formula Ia', Ib', Ic', or II' in combination with Bortezomib or other proteosome inhibitors.

In another aspect, the invention provides a method for treating chronic lymphocytic leukemia patients with pharmaceutical compositions comprising one or more compounds of Formula Ia', Ib', Ic', or II' in combination with Bortezomib.

In another aspect, the invention provides a method for treating Non-Hodgkin's lymphoma patients with pharmaceutical, compositions comprising one or more compounds of Formula Ia', Ib', Ic', or II' in combination with Bortezomib.

In another aspect, the invention provides a method, for treating breast, cancer patients with pharmaceutical compositions comprising one or more compounds of Formula Ia', Ib', Ic', or II' in combination with Bortezomib.

In another aspect, the invention provides a method for treating prostate cancer patients with, pharmaceutical compositions comprising one or more compounds of Formula Ia', Ib', Ic', or II' in combination with Bortezomib.

In another aspect, the invention provides a method for treating colon cancer patients with pharmaceutical compositions comprising one or more compounds of Formula Ia', Ib', Ic', or II' in combination with Bortezomib.

In another aspect, the invention provides a method for treating pancreatic cancer patients with pharmaceutical compositions comprising one or more compounds of Formula Ia', Ib', Ic', or II' in combination with Bortezomib.

In another aspect, the invention, provides a method for treating liver cancer patients with pharmaceutical compositions comprising, one or more compounds of Formula Ia', Ib', Ic', or II' in combination with Bortezomib.

In another aspect, the invention provides a method for identifying compounds of the BH3 mimic class of small molecules that are active against a subset of the BH3 domain containing proteins arid therefore have predicted efficacy against particular tumor types.

In another aspect, the invention provides a method of treating a mammal suffering from migrating transformed B-Cell tumors (non-Hodgkins) comprising the steps of administering pharmaceutical composition comprising a compound of Formula Ia', Ib', Ic', or II' and monitoring said mammal to determine state of said cancer; wherein said cancer is a cancer sensitive to said chemical targeted to Bcl-2 family; optionally wherein the amount administered is a quantity sufficient to constitute effective treatment, or wherein, said cancer is chosen from, a group of cancers consisting of lymphoma, breast cancer; leukemia, lung cancer, bone cancer, prostate cancer gastric cancer, colon cancer, metal cancer, liver cancer, cervical cancer, renal cancer, bladder cancer, nasopharyngeal cancer, esophagus cancer, pituitary gland tumor; thyroid cancer melanoma and pancreatic cancer.

In another aspect, the invention provides a method of preventing cancer comprising the step of administering a chemical to persons having a high risk of cancer.

In another aspect the invention provides a method for selecting specific activity of a BH3 mimic compound based on similar activity to a peptide comprised of a particular BH3 domain.

In various embodiments of the invention, a mammal is a human; cancer is Multiple Myeloma.

In various embodiments of the invention, a mammal is a human; cancer is Non-Hodgkin's Lymphoma; cancer is any other B-cell lymphomas; cancer is Small lymphocytic, consistent CLL; cancer is Follicular, predominantly small cleaved cell; cancer is Follicular, mixed small cleaved and large cell; cancer is Intermediate grade Follicular, large cell; cancer is Diffuse, small cleaved cell; cancer is Diffuse, mixed small cleaved and large cell; cancer is Diffuse, large cell (cleaved and non-cleaved; said cancer is High grade; cancer is Large cell, immunoblastic; cancer is Lymphoblastic; cancer is Small non-cleaved cell; cancer is Burkitt Non-Burkitt; cancer is Indolent NHL; cancer is B-cell CLL/small lymphocytic lymphoma; cancer is Marginal zone lymphoma; cancer is MALT; cancer is Splenic marginal 27, 27; cancer is zone lymphoma; cancer is Nodal marginal zone lymphoma; cancer is Lymphomplasmacytoid lymphoma/immunocytoma; cancer is Follicle center lymphoma, follicular type Grade I (0-5 centroblasts/hpf) or Grade II (6-15 centroblasts/hpf) or Grade III† (>15 centroblasts/hpf); cancer is Aggressive NHL; cancer is Diffuse, large cell lymphoma; cancer is Mediastinal large cell lymphoma; cancer is Primary effusion lymphoma; cancer is Mantle cell lymphoma†; cancer is Burkitt's lymphoma/high-grade Burkitt's-like; cancer is Precursor B-cell leukemia/lymphoma; cancer is Precursor T-cell leukemia/lymphoma; cancer is skin cancer; cancer is prostate cancer; cancer is gastric cancer; cancer is colon cancer; cancer is rectal cancer; cancer is liver cancer; cancer is cervical cancer; cancer is renal cancer; cancer is bladder cancer; cancer is nasopharyngeal cancer; cancer is esophagus cancer; cancer is pituitary gland tumor; cancer is thyroid cancer; cancer is melanoma; or cancer is pancreatic cancer.

In addition, in various embodiments of the invention, the chemical is administered by injecting it directly Into a tumor; the chemical is administered by injecting it into said mammal's blood stream; the chemical is administered orally; the chemical is administered through said mammal's skin; the chemical targeted to compounds of Formula Ia', Ib', Ic', or II' are administered in combination with prior art chemotherapy agents; or pharmaceutical composition comprising a compound of Formula Ia', Ib', Ic', or II' are administered in combination with radiation, therapy.

BRIEF DESCRIPTION OF THE DRAWINGS

The objects and features of the invention may be more fully understood by reference to the drawings as described, below in which.

Figure 1:
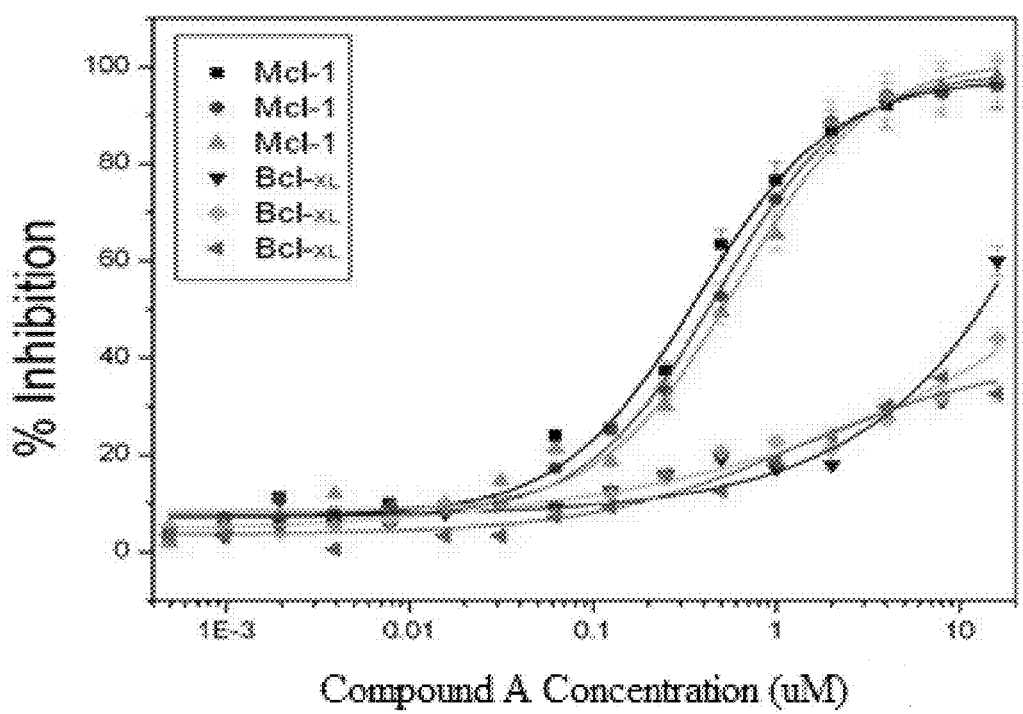
FIG. 1 is a graph showing preferential competition of Bim-BH3 peptide binding to Mcl-1 vs. Bim-BH3 peptide binding to Bcl-xL by the BH3 mimic compound A. Fluorescence Polarization (FP) was used to measure binding as described in Example 2.

The details of the invention are set forth in the accompanying description below. Although methods and materials similar or equivalent to those described herein can be used in the practice or testing of the present invention, iIllustrative methods and materials are now described. Other features, objects, and advantages of the invention will be apparent from, the description and from the claims, in the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE INVENTION

Definitions

The term "heteroaryl" as used herein refers to a monocyclic or bicyclic ring structure having 5 to 12 ring atoms wherein one or more of the ring atoms is a heteroatom, e.g. N, O or S and wherein one or more rings of the tricyclic ring structure is aromatic. Some examples of heteroaryl are pyridyl, furyl, pyrrolyl, thienyl, thiazolyl, oxazolyl, imidazolyl, indolyl, tetrazolyl, benzofuryl, xanthenes and dihydroindole. It is understood that any of the substitutable hydrogens on a heteroaryl can be substituted with halogen, $C_1$-$C_3$ alkyl, hydroxyl, alkoxy and cyano groups.

As used, herein "anti-apoptotic-protein" is a protein, which when expressed, in a cell, blocks programmed cell death in cancer cells, or other cells that are otherwise being directed to undergo apoptosis.

As used herein "hematological malignancies" refers to any cancer of the blood or bone marrow, sueh as leukemia or lymphoma. Examples include but not limited to; Myelomas (e.g. Multiple myeloma and Giant cell myeloma), Acute lymphoblastic leukemia (ALL), Acute myelogenous leukemia (AML), Acute myelogenous leukemia (AML), Chronic myelogenous leukemia (CML), Acute monocytic leukemia (AMOL), Hodgkin's lymphomas (all four subtypes), in addition. Non-Hodgkin's lymphomas such as Diffuse large B-cell lymphoma (DLBCL), Follicular lymphoma (FL), Mantle cell lymphoma (MCL), Marginal zone lymphoma (MZL), Burkitt's lymphoma (BL), Burkitt's lymphoma (BL), and other NK- or T-cell lymphomas are included.

As used herein, the term "Bcl-2" refers to the anti-apoptotic protein originally discovered as the causal "oncogene" in lymphomas and first discovered among the anti-apoptotic Bcl-2 family proteins.

As used, herein "pro-apoptotic protein" means a protein that when expressed in a cell causes the cell to undego apoptosis.

By "disrupts an interaction" is meant that a test compound decreases the ability of two polypeptides to interact with each other. In certain instances the disruption results in at least a 99% decrease in the ability of the polypeptides to interact with each other. These were identified using a combination of virtual screening for molecular structures, which fit the Ideal structure of BH3 pocket and competition binding studies using fluorescence polarization (FP).

By "fluorescence polarization assay" is meant an assay in which an interaction between two polypeptides is measured. In this assay, one polypeptide is labeled with a fluorescent tag, and this polypeptide emits non-polarized light when excited with polarized light. Upon an interaction of the tagged polypeptide with another polypeptide, the polarization of emitted light is increased, and this increased polarization of light can be detected. By "interacts" is meant a compound that recognizes and binds to an anti-apoptotic protein but which does not substantially recognize and bind to other molecules in a sample.

The present invention generally relates to compositions and methods for treating hematological malignancies. Such hematological malignancies include, for example, Multiple Myeloma, B-cell lymphoma, acute myelogenous leukemia, and chronic lymphocytic leukemia. Such treatment, results in, for example, tumor regression in a mammal, such as a mouse or a human. Tumor regression can include, for example, killing a cancer cell.

There is provided in accordance with one aspect of the invention, compounds of Formula Ia:

$$Ar_1\text{-}L_1\text{-}Ar_2\text{-}L_2\text{-}Ar_3\text{-}L_3\text{-}Ar_4 \qquad \text{Formula Ia}$$

and stereoisomers, tautomers, solvates, and pharmaceutically acceptable salts, thereof, wherein $Ar_1$, $Ar_2$, $Ar_3$, $Ar_4$, $L_1$, $L_2$ and $L_3$ are defined above for Formula Ia;

provided, that the compound of Formula la is not 2,2,-(3,3'-dimethoxybihenyl-4,4'-diyl)bis(azanediyl)dibenzoic acid or N4, N4'-bis(1-iminoisoindolin-5-yl)biphenyl-4,4'-diamine.

In some embodiments, $Ar_1$, $Ar_2$, $Ar_3$, and $Ar_4$ are each independently selected from null, indazolyl, indolyl, isoindolyl, imidazolyl, benzimidazolyl, isoxazolyl, oxazolyl, thiazolyl, benzothiazolyl, piperidinyl, pyrazolyl, pyrazolinyl, pyrrolyl, pyrrolinyl, pyridinyl, pyridazinyl, pyrimidinyl, quinolinyl, isoquinolinyl, tetrahydroquinolyl, dihydroquinolyl, phthalazinyl, dihydroindolyl, indolinyl, benzoisoxazolyl, dihydrobenzoisoxazolyl, dihydroisoindolyl, benzoisothiazolyl, benzoisothiazolyl dioxide, cyclopentyl, cyclohexyl, tetrahydropyranyl, each of which is optionally substituted with one or more substituents $R^s$.

In some embodiments, $Ar_1$, $Ar_2$, $Ar_3$, and $Ar_4$ are each $C_6$-$C_{10}$ aryl.

In some embodiments, $Ar_2$ and $Ar_3$ are each $C_6$-$C_{10}$ aryl.
In some embodiments, $Ar_2$ and $Ar_3$ are each $C_6$ aryl.
In some embodiments, $Ar_2$ and $Ar_4$ are each $C_6$ aryl.
In some embodiments, $Ar_1$ and $Ar_4$ are the same.
In some embodiments, $Ar_1$ and $Ar_4$ are not the same.
In some embodiments, $Ar_1$ and $Ar_4$ are each null.
In some embodiments, $Ar_1$ and $Ar_4$ are each $C_{5\text{-}10}$ membered heterocyclic.

In some embodiments, $Ar_1$ is pyridinyl and $Ar_4$ is phenyl.
In some embodiments, $Ar_1$ and $Ar_4$ are each pyrimidinyl.
In some embodiments, $Ar_1$ and $Ar_4$ are each pyrazolyl.
In some embodiments, $Ar_1$ and $Ar_4$ are each isoxazolyl.
In some embodiments, $Ar_1$ and $Ar_4$ are each a quinolinyl.
In some embodiments, L2 is a bond.
In some embodiments, L2 is other than a bond.
In some embodiments, L2 is —S(O)2-.
In some embodiments, L1 and L3 are the same.
In some embodiments, L1 and L3 are not the same.
In some embodiments, L1 and L3 are each —NR—.
In some embodiments, L1 and L3 are each —O—.
In some embodiments, $L_1$ is NR and $L_3$ is O.
In other illustrative embodiments, compounds of Formula Ia are set forth below:

2,2'-((Sulfonylbis(2-methoxy-4,1-phenylene))bis (azanediyl))dibenzoic acid (Ia-1);

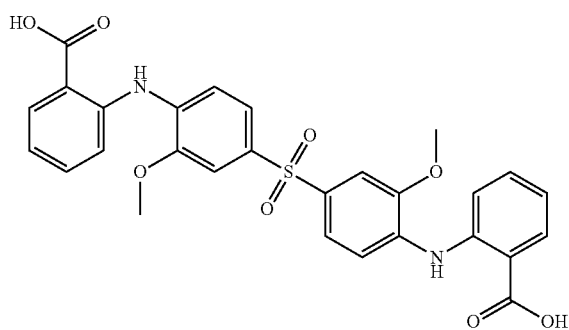 [SMILES: COc1cc(S(=O)(=O)c2ccc(Nc3ccccc3C(=O)O)c(OC)c2)ccc1Nc1ccccc1C(=O)O]

3,3'-((3,3'-Dimethoxy-[1,1'-biphenyl]-4,4'-diyl)bis (azanediyl))dipropanoic acid (Ia-2);

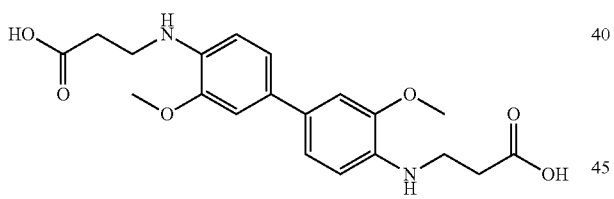

3,3'-((3,3'-Dimethoxy-[1,1'-biphenyl]-4,4'-diyl)bis (azanediyl))bis(3-phenylpropanoic acid) (Ia-3);

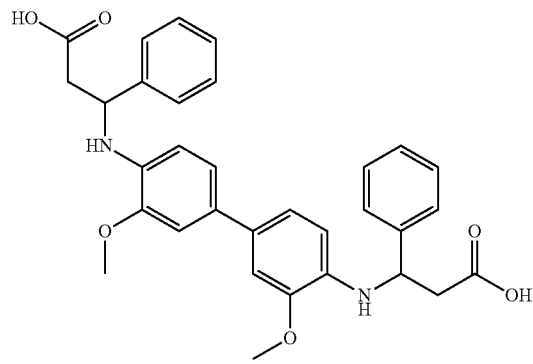 [SMILES: COc1cc(-c2ccc(NC(CC(=O)O)c3ccccc3)c(OC)c2)ccc1NC(CC(=O)O)c1ccccc1]

3,3'-((3,3'-Dimethoxy-[1,1'-biphenyl]-4,4'-diyl)bis (azanediyl))bis(2-phenylpropanoic acid) (Ia-4);

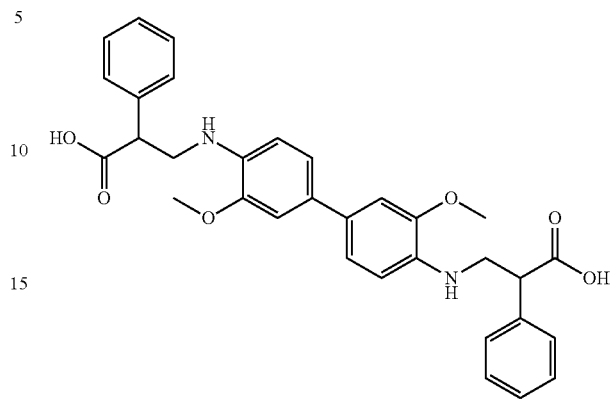

2,2'-((3,3'-Dimethoxy-[1,1'-biphenyl]-4,4'-diyl)bis (azanediyl))bis(2-phenylacetic acid) (Ia-5);

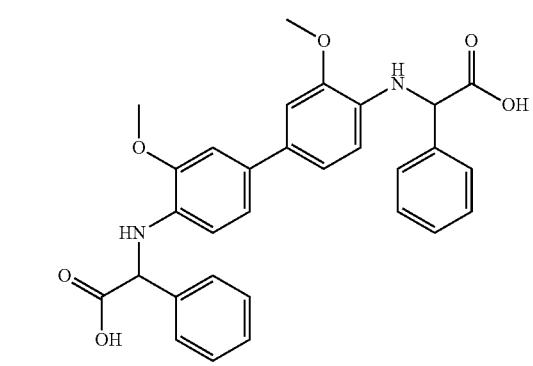 [SMILES: COc1cc(-c2ccc(NC(C(=O)O)c3ccccc3)c(OC)c2)ccc1NC(C(=O)O)c1ccccc1]

2,2'-(((3,3'-Dimethoxy-[1,1'-biphenyl]-4,4'-diyl)bis (azanediyl))bis(sulfonyl))dibenzoic acid (Ia-6);

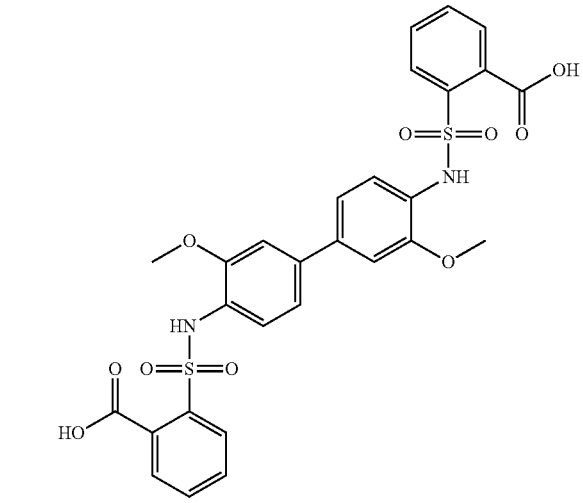 [SMILES: COc1cc(-c2ccc(NS(=O)(=O)c3ccccc3C(=O)O)c(OC)c2)ccc1NS(=O)(=O)c1ccccc1C(=O)O]

2-((4'-((2-Carboxyphenyl)sulfonyl)-3,3'-dimethoxy-[1,1'-biphenyl]-4-yl)sulfonyl)-6-methylbenzoic acid (Ia-7);

Methyl 2-oxo-1-(2,2',6,6'-tetrahydroxy-4'-((2-hydroxy-5-(methoxycarbonyl)phenyl)amino)-[1,1'-biphenyl]-4-yl)indoline-6-carboxylate (Ia-9);

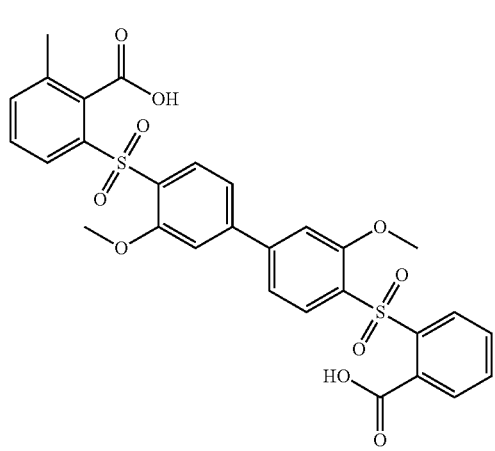 [SMILES: COc1cc(-c2ccc(S(=O)(=O)c3cccc(C)c3C(=O)O)c(OC)c2)ccc1S(=O)(=O)c1ccccc1C(=O)O]

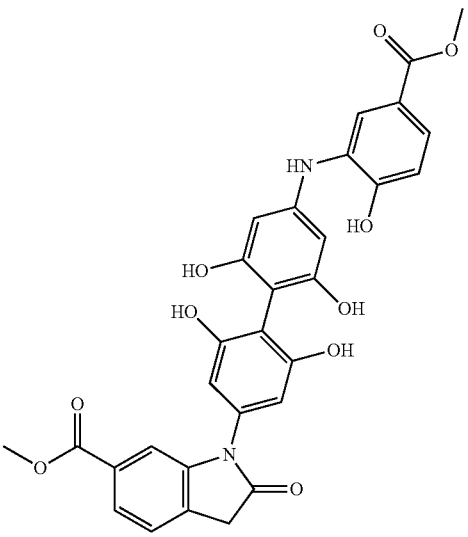

Methyl 1-(2,2',6,6'-tetrahydroxy-4'-((2-hydroxy-5-(methoxycarbonyl)phenyl)amino)-[1,1'-biphenyl]-4-yl)-1H-indole-6-carboxylate (Ia-8);

Methyl 2-oxo-3-(2,2',6,6'-tetrahydroxy-4'-((2-hydroxy-5-(methoxycarbonyl)phenyl)amino)-[1,1'-biphenyl]-4-yl)-2,3-dihydro-1H-benzo[d]imidazole-5-carboxylate (Ia-10);

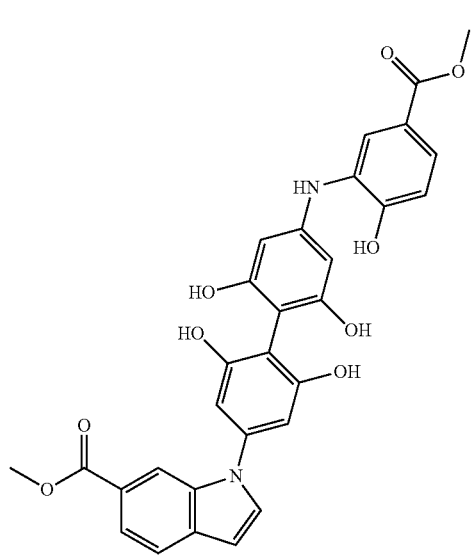

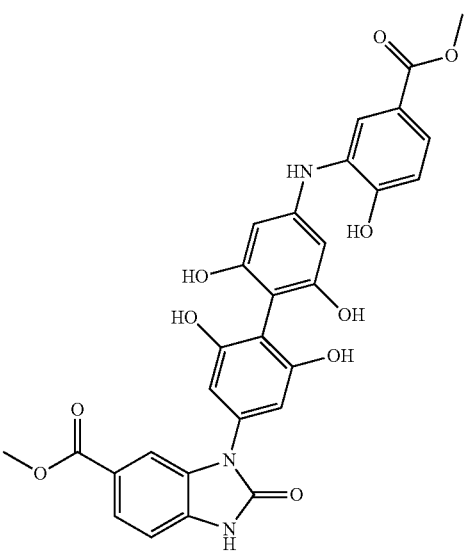

Methyl 2-oxo-1-(2,2',6,6'-tetrahydroxy-4'-((2-hydroxy-5-(methoxycarbonyl)phenyl)amino)-[1,1'-biphenyl]-4-yl)-1,2,3,4-tetrahydroquinoline-7-carboxylate (Ia-11);

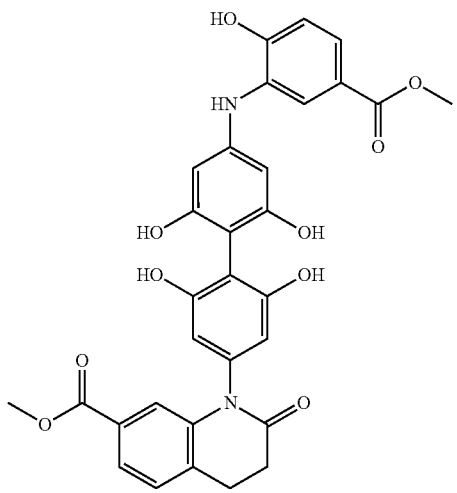

Methyl 1-(2,2',6,6'-tetrahydroxy-4'-((2-hydroxy-5-(methoxycarbonyl)phenyl)amino)-[1,1'-biphenyl]-4-yl)-1,2,3,4-tetrahydroquinoline-7-carboxylate (Ia-12);

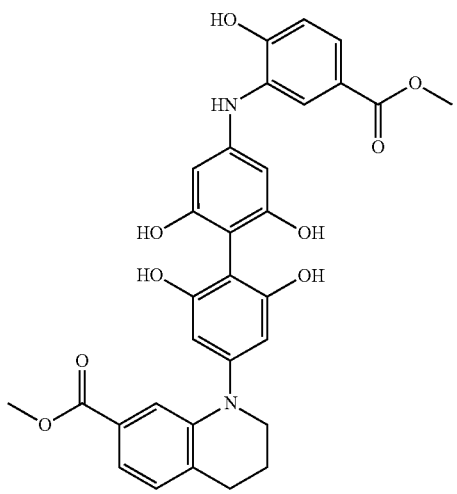

Methyl 2-oxo-1-(2,2',6,6'-tetrahydroxy-4'-((2-hydroxy-5-(methoxycarbonyl)phenyl)amino)-[1,1'-biphenyl]-4-yl)-1,2-dihydroquinoline-7-carboxylate (Ia-13);

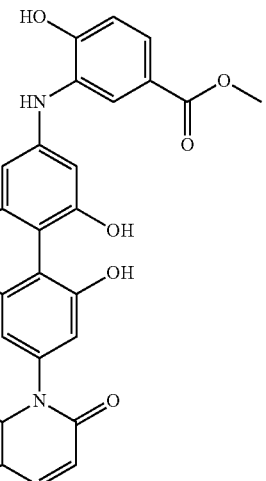

2-(2,2',6,6'-Tetrahydroxy-4'-(7-(methoxycarbonyl-2-oxo-3,4-dihydroquinolin-1(2H)-yl)-[1,1'-biphenyl]-4-yl)amino)benzoic acid (Ia-14);

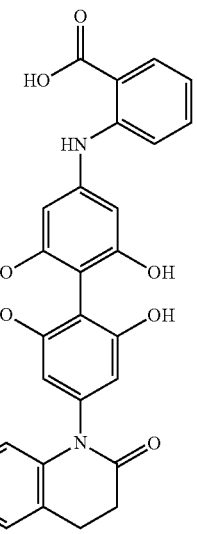

2-((4'-((2-carboxyphenyl)(methyl)amino)-3,3'-dimethoxy-[1,1'-biphenyl]-4-yl)amino)benzoic acid (Ia-15);

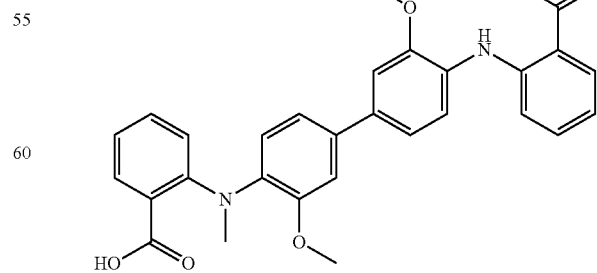

2,2'-((3,3'-dimethoxy-[1,1'-biphenyl]-4,4'-diyl)bis(methylazanediyl))dibenxoic acid (Ia-16);

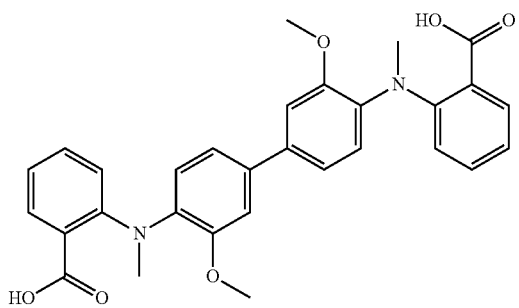 [SMILES: COc1cc(-c2ccc(N(C)c3ccccc3C(=O)O)c(OC)c2)ccc1N(C)c1ccccc1C(=O)O]

2-((4'-(2-carboxybenzyl)-3,3'-dimethoxy-[1,1'-biphenyl]-4-yl)amino)benzoic acid (Ia-17);

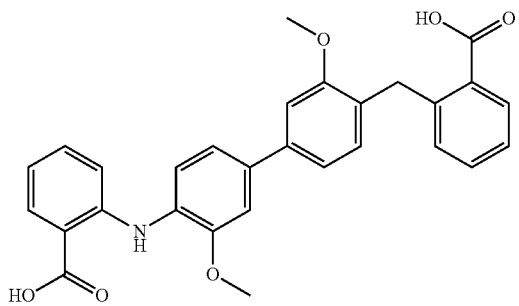 [SMILES: COc1cc(-c2ccc(Nc3ccccc3C(=O)O)c(OC)c2)ccc1Cc1ccccc1C(=O)O]

2,2'-((3,3'-dimethoxy-[1,1'-biphenyl]-4,4'-diyl)bis(methylene))dibenzoic acid (Ia-18);

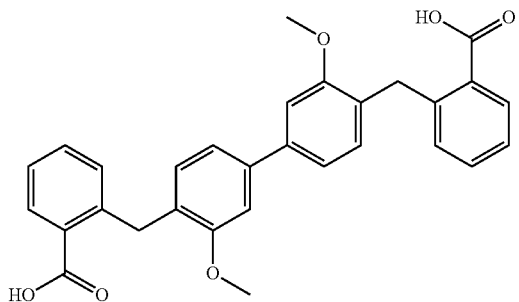 [SMILES: COc1cc(-c2ccc(Cc3ccccc3C(=O)O)c(OC)c2)ccc1Cc1ccccc1C(=O)O]

2,2'-((3,3'-dihydroxy-[1,1'-biphenyl]-4,4'-diyl)bis(oxy))dibenzoic acid (Ia-19);

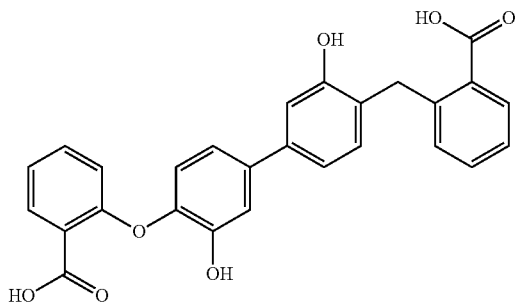 [SMILES: O=C(O)c1ccccc1Cc1ccc(-c2ccc(Oc3ccccc3C(=O)O)c(O)c2)cc1O]

dimethyl 2,2'-((3,3'-dimet6hoxy-[1,1'-biphenyl]-4,4'-diylo)bis(azanediyl))dibenzoate (Ia-20);

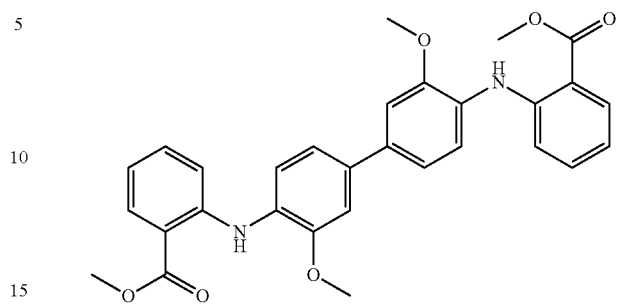

6,6'-((3,3'-dimethoxy-[1,1'-biphenyl]-4,4'-diyl)bis(3-methylbenzoic acid) (Ia-21).

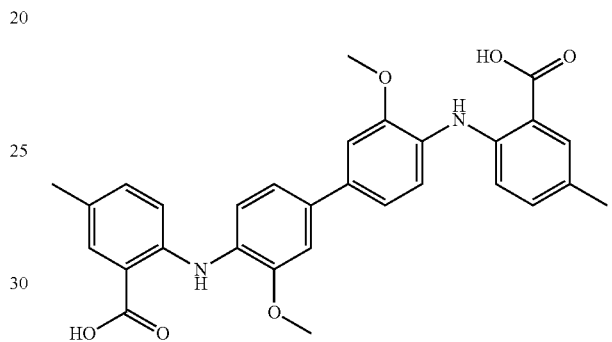

In another aspect, there is provided compounds of Formula Ib:

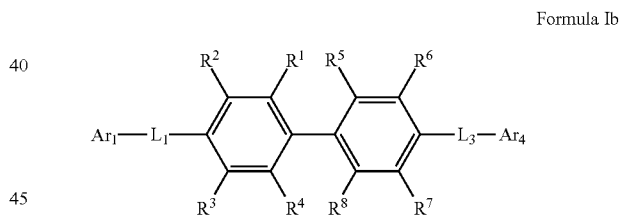

Formula Ib and stereoisomers, tautomers, solvates, and pharmaceutically acceptable salts, thereof, wherein $Ar_1, Ar_4, R^1, R^2, R^3, R^4, R^5, R^6, R^7$, and $R^8$, $L_1$ and $L_3$ are as defined above for Formula Ib, with the proviso that the compound of Formula Ib is not 2,2'-(3,3'-dimethoxybiphenyl-4,4'-diyl)bis(azanediyl)dibenzoic acid, and $Ar_1$ and $Ar_4$ are not simultaneously isoindolin-1-imine.

In some embodiments, $Ar_1$ and $Ar_4$ are each independently selected from null, indazolyl indolyl, isoindolyl, imidazolyl, benzimidazolyl, isoxazolyl, oxazolyl, thiazolyl, benzothiazolyl, piperidinyl, pyrazolyl, pyrazolinyl, pyrrolyl, pyrrolinyl, pyridinyl, pyridazinyl, pyrimidinyl, quinolinyl, isoquinoinyl, tetrahydroquinolyl, dihydroqinolyl, phthalazinyl, dihydroindolyl, indolinyl, benzoisothiazolyl, dihydrobenzoisoxazolyl, dihydroisoindolyl, benzoisothiazolyl, benzoisothiazolyl dioxide, each of which is optionally substituted with one or more substituents $R^s$.

In some embodiments, $Ar_1$ and $A_4$ are each independently selected from cyclopentanyl, cyclohexyl tetrahydropyranyl, and piperidinyl.

In some embodiments, Ar₁ and A₄ are each cyclopentanyl.
In some embodiments, Ar₁ and A₄ are each cyclohexyl.
In some embodiments, Ar₁ and A₄ are each piperidinyl.
In some embodiments, $L_1$ and $L_3$ are each NH.
In some embodiments, illustrative compounds of Formula Ib are described below:

2,2'-((3,3'-Dimethoxy-[1,1'-biphenyl]-4,4'-diyl)bis(azanediyl))dicyclopentanecarboxylic acid (Ib-1);

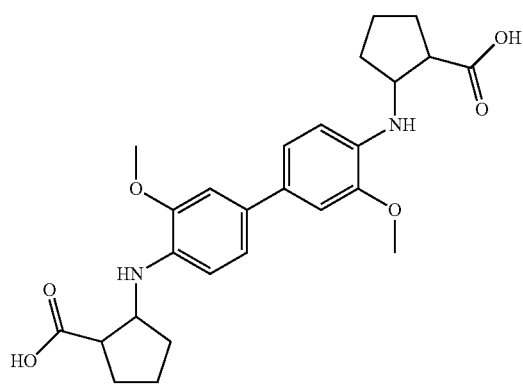 [SMILES: COc1cc(-c2ccc(NC3CCCC3C(=O)O)c(OC)c2)ccc1NC1CCCC1C(=O)O]

2,2'-((3,3'-Dimethoxy-[1,1'-biphenyl]-4,4'-diyl)bis(azanediyl))dicyclohexanecarboxylic acid (Ib-2);

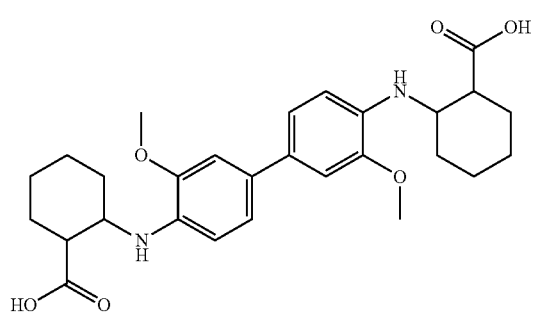 [SMILES: COc1cc(-c2ccc(NC3CCCCC3C(=O)O)c(OC)c2)ccc1NC1CCCCC1C(=O)O]

4,4'-((3,3'-Dimethoxy-[1,1'-biphenyl]-4,4'-diyl)bis(azanediyl))bis(tetrahydro-2H-pyran-3-carboxylic acid) (Ib-3); and

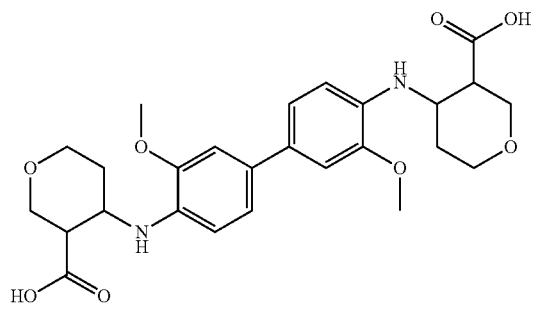 [SMILES: COc1cc(-c2ccc(NC3CCOCC3C(=O)O)c(OC)c2)ccc1NC1CCOCC1C(=O)O]

1,1'-(3,3'-Dimethoxy-[1,1'-biphenyl]-4,4'-diyl)bis(piperidine-2-carboxylic acid) (Ib-4).

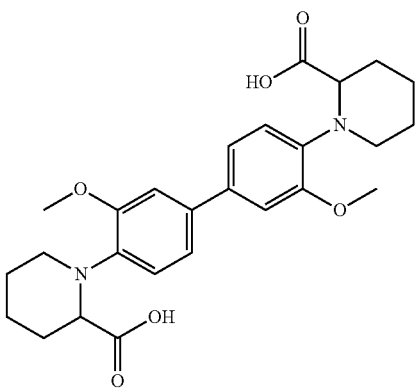 [SMILES: COc1cc(-c2ccc(N3CCCCC3C(=O)O)c(OC)c2)ccc1N1CCCCC1C(=O)O]

In another aspect, there is provided compounds of Formula Ic:

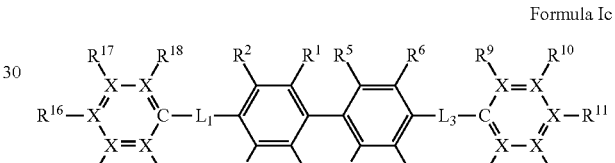

Formula Ic and stereoisomers, tautomers, solvates, and pharmaceutically acceptable salts, thereof, wherein Ar₁, and Ar₄ $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $L_1$ and $L_3$ are as defined above for Formula Ic, with the proviso that the compound of Formula Ia is not 2,2'-(3,3'-dimethoxybiphenyl-4,4'-diyl)bis(azanediyl)dibenzoic acid.

In other embodiment, illustrative compounds of Formula Ic are described below;

3,3'-((3,3'-dimethoxy-[1,1'-bipenyl]-4,4'-diyl)bis(azanediyl))dibenzoic acid (Ic-1);

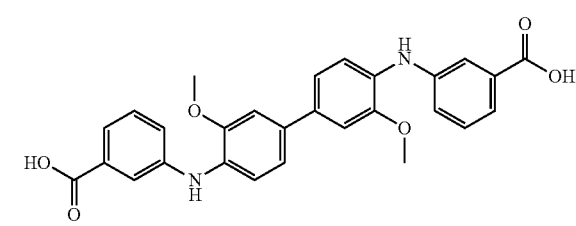 [SMILES: COc1cc(-c2ccc(Nc3cccc(C(=O)O)c3)c(OC)c2)ccc1Nc1cccc(C(=O)O)c1]

2,2'-((3,3'-dihydroxy-[1,1'-biphenyl]-4,4'-diyl)bis(azanediyl))dibenzoic acid (Ic6);

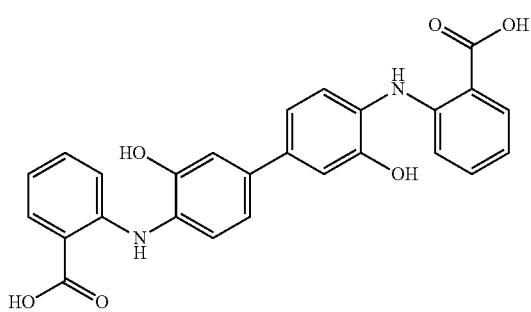 [SMILES: O=C(O)c1ccccc1Nc1ccc(-c2ccc(Nc3ccccc3C(=O)O)c(O)c2)cc1O]

2-((4'-((2-carboxyphenyl)amino)-3,3'-dimethoxy-[1,1'-biphenyl]-4-Yl)amino)-5-methylbenzoic acid (Ic-7);

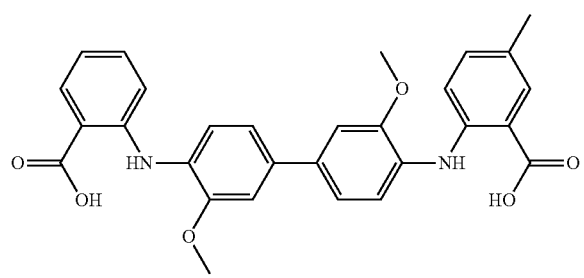 [SMILES: COc1cc(-c2ccc(Nc3ccc(C)cc3C(=O)O)c(OC)c2)ccc1Nc1ccccc1C(=O)O]

3-((4'-((2-carboxyphenyl)amino-3,3'-dimethoxy-[1,1'-biphenyl]-4-yl)amino)isonicotinic acid (Ic-8);

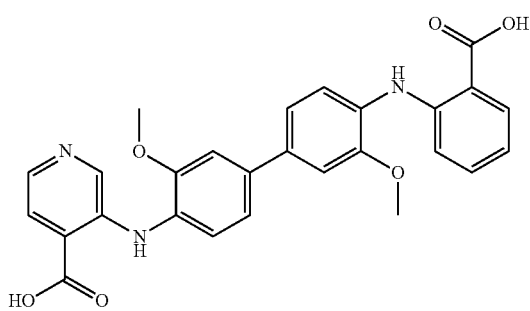 [SMILES: COc1cc(-c2ccc(Nc3cnccc3C(=O)O)c(OC)c2)ccc1Nc1ccccc1C(=O)O]

6,6'-((3,3'-dimethoxy-[1,1'-biphenyl]-4,4'-diyl)bis(azanediyl))bis(3-methylbenzoic acid) (Ic-17); and

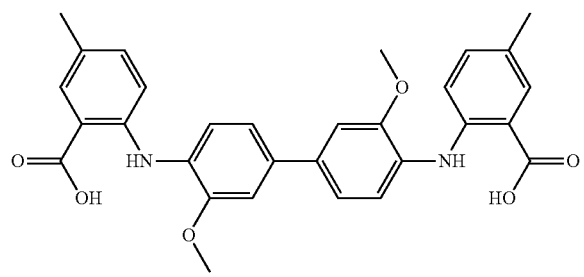 [SMILES: COc1cc(-c2ccc(Nc3ccc(C)cc3C(=O)O)c(OC)c2)ccc1Nc1ccc(C)cc1C(=O)O]

2,2'-((3,3'-dimethoxy-[1,1'-biphenyl]-4,4'-diyl)bis(azanediyl))bis(4-methoxybenzoic acid) (Ic-18);

2,2'-(((((3,3'-dimethoxy-[1,1'-biphenyl]-4,4'-diyl)bis(azanediyl))bis(2,1-phenylene))bis(oxy))diacetic acid (Ic-2);

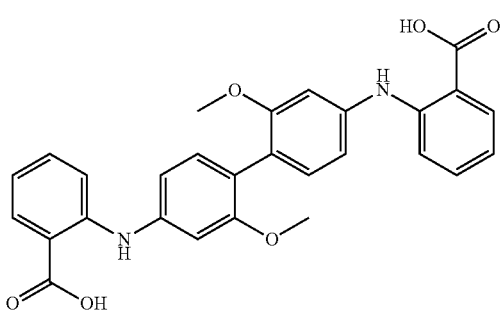 [SMILES: COc1cc(Nc2ccccc2C(=O)O)ccc1-c1ccc(Nc2ccccc2C(=O)O)cc1OC]

2,2'-((2,2'-dimethoxy-[1,1'-biphenyl]-4,4'-diyl)bis(azanediyl))dibenzoic acid (Ic-3);

2,2'-((2,3'-dimethoxy-[1,1'-biphenyl]-4,4'-diyl)bis(azanediyl))dibenzoic acid (Ic-4);

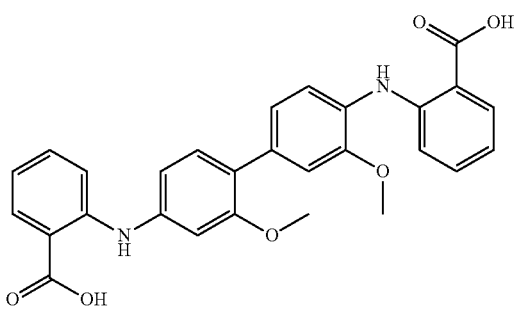 [SMILES: COc1cc(-c2ccc(Nc3ccccc3C(=O)O)cc2OC)ccc1Nc1ccccc1C(=O)O]

2-((4'-(2-carboxyphenoxy)-3,3'-dimethoxy-[1,1'-biphenyl]-4-yl)amino)benzoic acid (Ic-5);

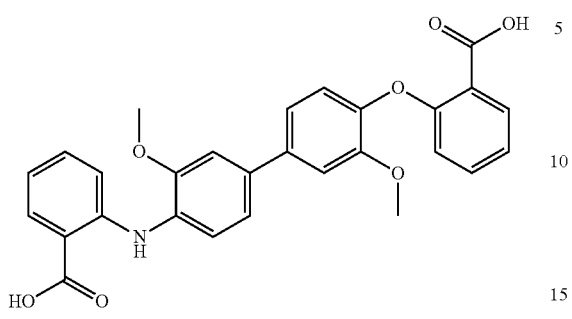

5,5'-((3,3'-dimethoxy-[1,1'-biphenyl]-4,4'-diyl)bis(azanediyl))bis(pyrimidine-4-carboxylic acid) (Ic-9);

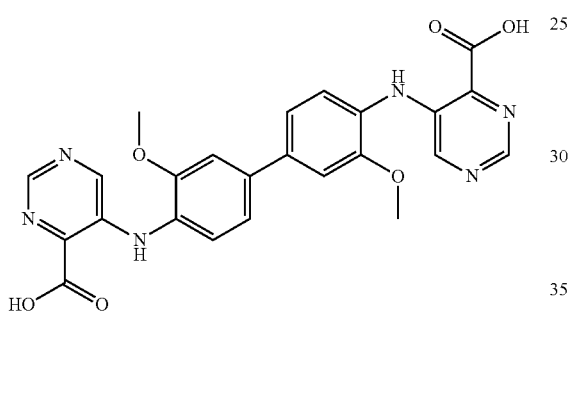

4-((4'-((4-carboxyl-1-methyl-1H-pyrazol-3-yl)amino)-3,3'-dimethoxy-[1,1'-biphenyl]-4-yl)amino)-1-methyl-1H-pyrazole-3-carboxylic acid (Ic-10);

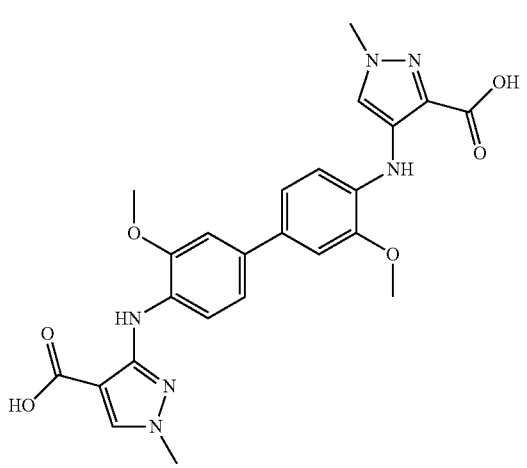 [SMILES: COc1cc(-c2ccc(Nc3nn(C)cc3C(=O)O)c(OC)c2)ccc1Nc1cn(C)nc1C(=O)O]

5-((4'-((5-carboxyisoxazol-4-yl)amino)-3,3'-dimethoxy-[1,1'-biphenyl]-4-yl)amino)isoxazole-4-carboxylic acid (Ic-11);

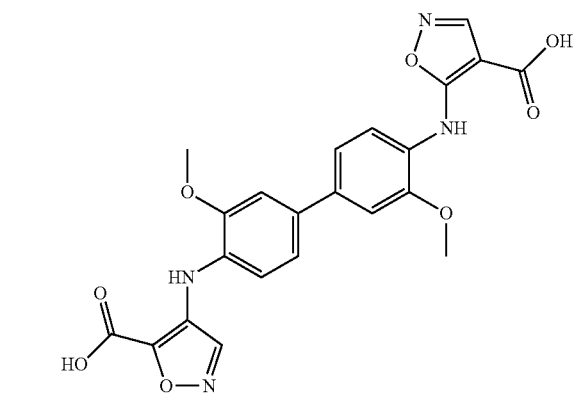 [SMILES: COc1cc(-c2ccc(Nc3oncc3C(=O)O)c(OC)c2)ccc1Nc1cnoc1C(=O)O]

5-((4'-((5-carboxy-2-methyloxazol-4-yl)amino)-3,3'-dimethoxy-[1,1'-biphenyl]-4-yl)amino)-2-methyloxazole-4-carboxylic acid (Ic12);

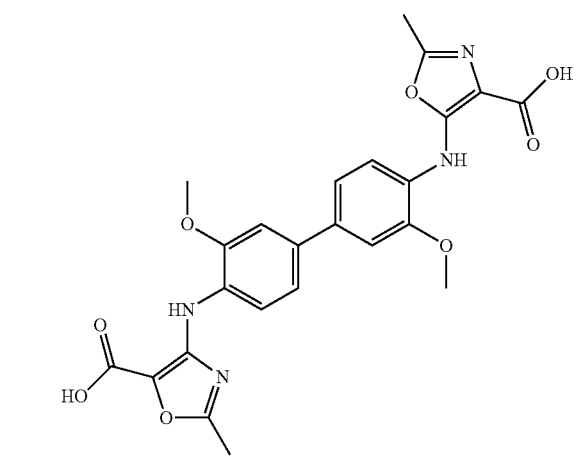 [SMILES: COc1cc(-c2ccc(Nc3oc(C)nc3C(=O)O)c(OC)c2)ccc1Nc1nc(C)oc1C(=O)O]

3,3'-((3,3'-dimethoxy-[1,1'-biphenyl]-4,4'-diyl)bis(azanediyl))diisonicotinic acid (Ic-13);

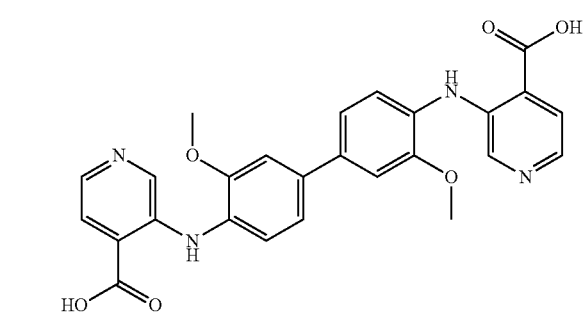 [SMILES: COc1cc(-c2ccc(Nc3cnccc3C(=O)O)c(OC)c2)ccc1Nc1cnccc1C(=O)O]

dimethyl 3,3'-((2-isopropoxy-2'-methoxy-[1,1'-biphenyl]-4,4'-diyl)bis(azanediyl))bis(4-hydroxybenzoate)(Ic-14);

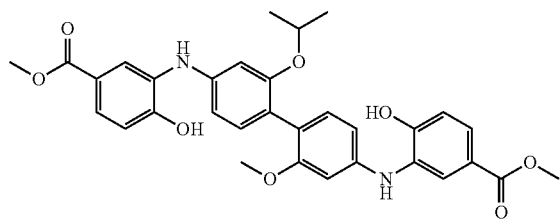

dimethyl 3,3'-((2,2',6,6'-tetrahydroxy-[1,1'-biphenyl]-4,4'-diyl)bis(azanediyl))bis(4-hydroxybenzoate)(Ic-15);

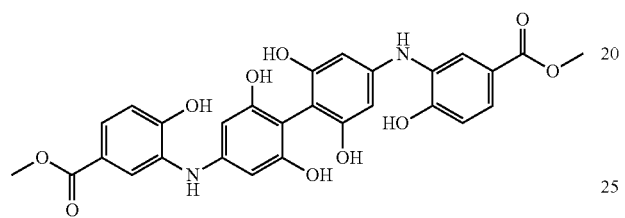

dimethyl 3,3'-((2,2'-dihydroxy-[1,1'-biphenyl]-4,4'-diyl)bis(azanediyl))bis(4-hydroxybenzoate)(Ic-16);

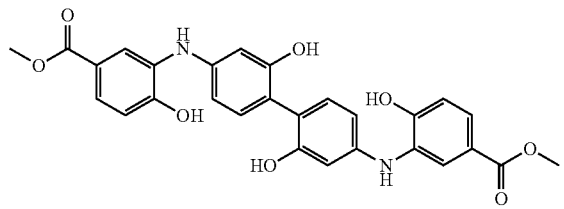

2-((2,2',6,6'-tetrahydroxy-4'-((2-hydroxy-5-(methoxycarbonyl)phenyl)amino)-[1,1'-biphenyl]-4-yl)amino)benzoic acid (Ic-19);

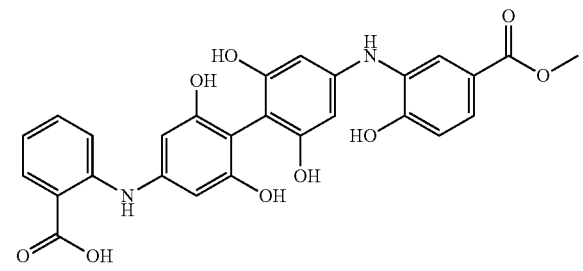 [SMILES: COC(=O)c1ccc(O)c(Nc2cc(O)c(-c3c(O)cc(Nc4ccccc4C(=O)O)cc3O)c(O)c2)c1]

2,2'-((2,2'-dimethoxy-[1,1'-biphenyl]-4,4'-diyl)bis(azanediyl))dibenzoic acid (Ic-20).

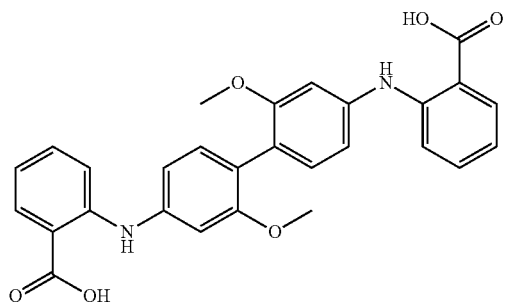 [SMILES: COc1cc(Nc2ccccc2C(=O)O)ccc1-c1ccc(Nc2ccccc2C(=O)O)cc1OC]

Also described herein are compounds of Formula II:

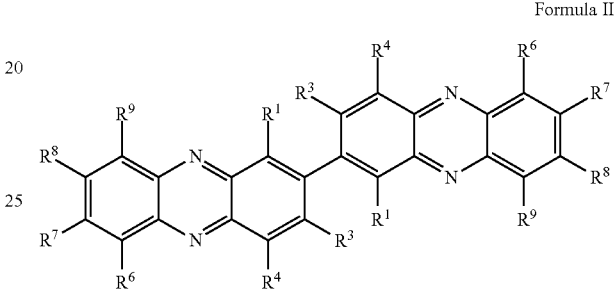

Formula II and stereoisomers, tautomers, solvates, and pharmaceutically acceptable salts, thereof, wherein.

$R^1$, $R^3$, $R^4$, $R^6$, $R^7$, $R^8$, and $R^9$ are as defined above for Formula II.

In some embodiments, two of $R^1$, $R^3$, $R^4$, $R^6$, $R^7$, $R^8$, and $R^9$ are each C(O)R.

In some embodiments, two of $R^1$, $R^3$, $R^4$, $R^6$, $R^7$, $R^8$, and $R^9$ are each C(O)methyl.

In some embodiments, four of $R^1$, $R^3$, $R^4$, $R^6$, $R^7$, $R^8$, and $R^9$ are each —OH.

In some embodiments, each $R^9$ is C(O)R.
In some embodiments, each R9 is C(O)methyl.
In some embodiments, each R1 and R6 is each OH.
In some embodiments, each R4 is C(O)R.
In some embodiments, each R4 is C(O)H.
In some embodiments, each R4 is CH2OH.

In other embodiments, illustrative compounds of Formula II are described below:

dimethyl 4,4'-diformyl-1,1',3,3',6,6'-hexahydroxy-[2,2'-biphenazine]-9,9'-dicarboxylate (II-19); and

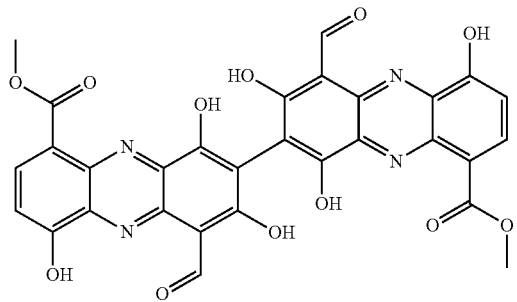 [SMILES: COC(=O)c1ccc(O)c2nc3c(C=O)c(O)c(-c4c(O)c(C=O)c5nc6c(O)ccc(C(=O)OC)c6nc5c4O)c(O)c3nc12]

dimethyl 1,1',3,3',6,6'-hexahydroxy-4,4'-bis(hydroxymethyl)-[2,2'-biphenazine]-9,9'-dicarboxylate (II-20).

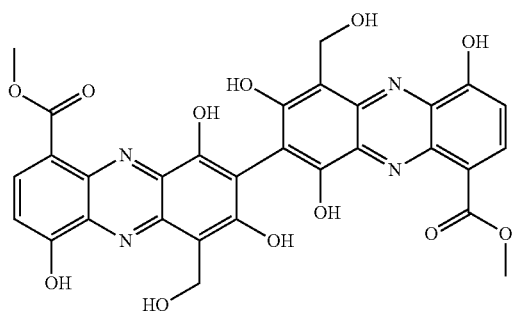 [SMILES: COC(=O)c1ccc(O)c2nc3c(CO)c(O)c(-c4c(O)c(CO)c5nc6c(O)ccc(C(=O)OC)c6nc5c4O)c(O)c3nc12]

dimethyl 1,1',3,3',6,6'-hexahydroxy-[2,2'-biphenazine]-9,9'-dicarboxylate (II-1);

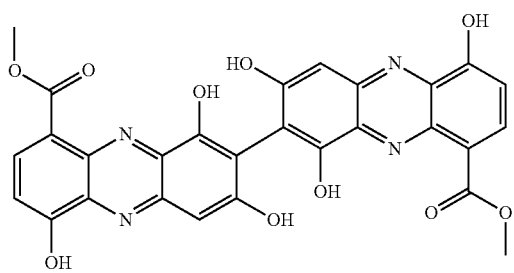 [SMILES: COC(=O)c1ccc(O)c2nc3cc(O)c(-c4c(O)cc5nc6c(O)ccc(C(=O)OC)c6nc5c4O)c(O)c3nc12]

1,1',3,3',6,6'-hexahydroxy-[2,2'-biphenazine]-9,9'-dicarboxylic acid (II-2);

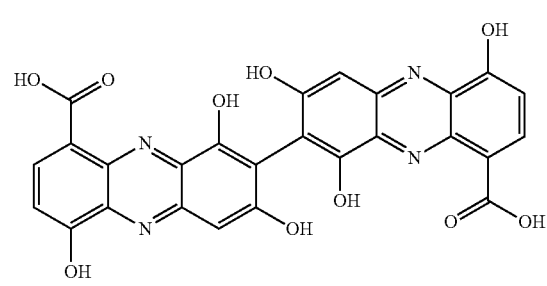 [SMILES: O=C(O)c1ccc(O)c2nc3cc(O)c(-c4c(O)cc5nc6c(O)ccc(C(=O)O)c6nc5c4O)c(O)c3nc12]

1,1'-(1,1',3,3',66'-hexahydroxy-[2,2'-biphenazine]-9,9'-diyl)diethanone (II-3);

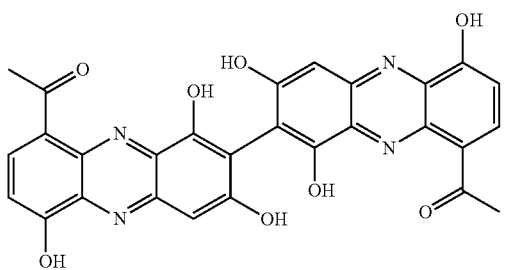 [SMILES: CC(=O)c1ccc(O)c2nc3cc(O)c(-c4c(O)cc5nc6c(O)ccc(C(C)=O)c6nc5c4O)c(O)c3nc12]

9,9'-bis(1-hydroxyethyl)-[2,2'-biphenazine]-1,1',3,3',6,6'-hexaol (II-4);

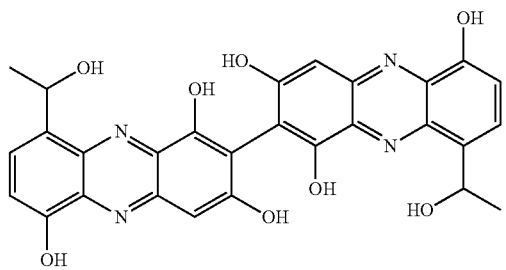 [SMILES: CC(O)c1ccc(O)c2nc3cc(O)c(-c4c(O)cc5nc6c(O)ccc(C(C)O)c6nc5c4O)c(O)c3nc12]

9,9'-bis(2-hydroxypropan-2-yl)-[2,2'-biphenazine]-1,1',3,3',6,6'-hexaol (II-5);

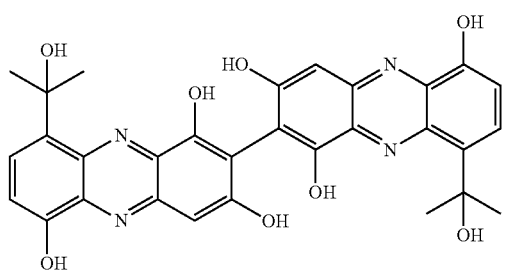 [SMILES: CC(C)(O)c1ccc(O)c2nc3cc(O)c(-c4c(O)cc5nc6c(O)ccc(C(C)(C)O)c6nc5c4O)c(O)c3nc12]

9,9'-diisopropyl-[2,2'-biphenazine]-1,1',3,3',6,6'-hexaol (II-6);

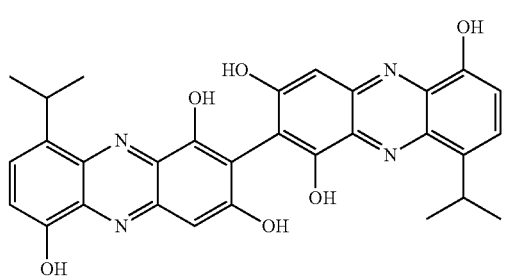 [SMILES: CC(C)c1ccc(O)c2nc3cc(O)c(-c4c(O)cc5nc6c(O)ccc(C(C)C)c6nc5c4O)c(O)c3nc12]

[2,2'-biphenazine]-1,1',3,3',6,6'-hexaol (II-7);

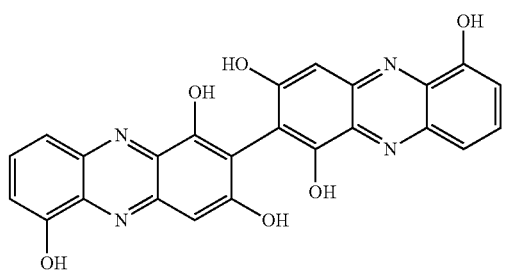 [SMILES: Oc1cc2nc3c(O)cccc3nc2c(O)c1-c1c(O)cc2nc3c(O)cccc3nc2c1O]

dimethyl 4,4'-bis((dimethylamino)methyl)-1,1',3,3',6,6'-hexahydroxy-[2,2'-biphenazine]-9,9'-dicarboxylate (II-8);

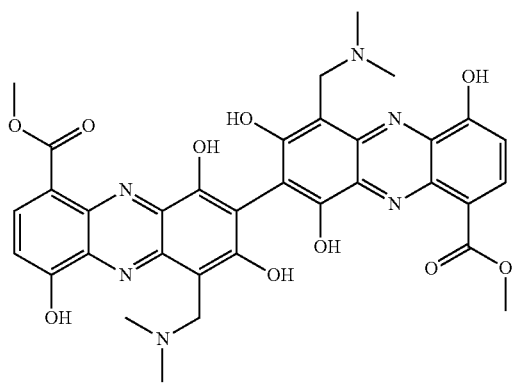 [SMILES: COC(=O)c1ccc(O)c2nc3c(CN(C)C)c(O)c(-c4c(O)c(CN(C)C)c5nc6c(O)ccc(C(=O)OC)c6nc5c4O)c(O)c3nc12]

dimethyl 4,4'-bis((benzylamino)methyl)-1,1',3,3',6,6'hexahydroxy-[2,2'-biphenazine]-9,9'-dicarboxylate (II-9);

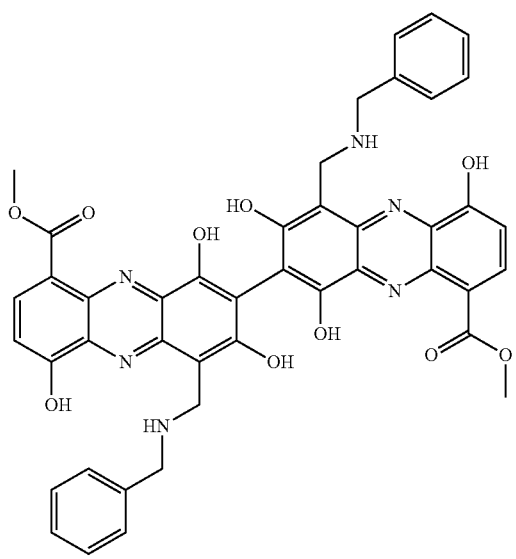 [SMILES: COC(=O)c1ccc(O)c2nc3c(CNCc4ccccc4)c(O)c(-c4c(O)c(CNCc5ccccc5)c5nc6c(O)ccc(C(=O)OC)c6nc5c4O)c(O)c3nc12]

dimethyl 1,1',3,3',6,6'-hexahydroxy-4,4'-bis((methylamino)methyl)-[2,2'-biphenazine]-9,9'-dicarboxylate (II-10);

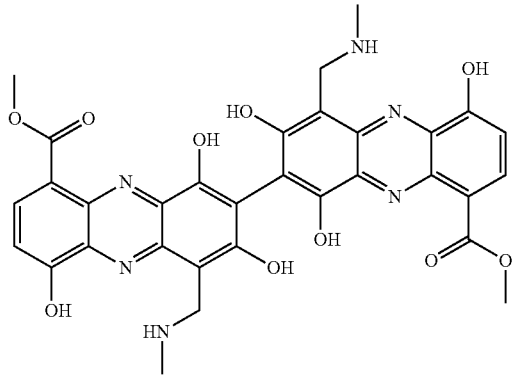 [SMILES: CNCc1c(O)c(-c2c(O)c(CNC)c3nc4c(O)ccc(C(=O)OC)c4nc3c2O)c(O)c2nc3c(C(=O)OC)ccc(O)c3nc12]

dimethyl 1,1',3,3',6,6'-hexahydroxy-4,4'-bis((isopropylamino)methyl)-[2,2'-biphenazine]-9,9'-dicarboxylate (II-11);

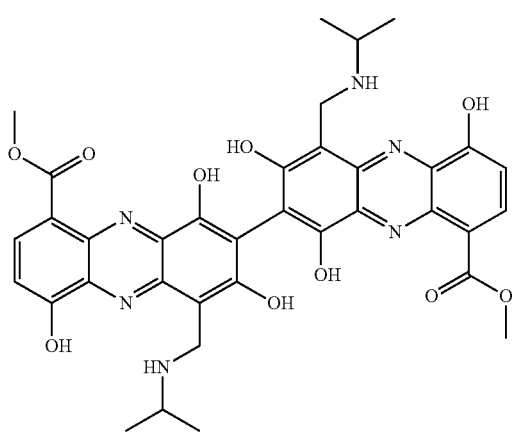 [SMILES: COC(=O)c1ccc(O)c2nc3c(CNC(C)C)c(O)c(-c4c(O)c(CNC(C)C)c5nc6c(O)ccc(C(=O)OC)c6nc5c4O)c(O)c3nc12]

dimethyl 1,1',3,3',6,6'-hexahydroxy-4,4'-bis((phenylamino)methyl)-[2,2'-biphenazine]-9,9'-dicarboxylate (II-12);

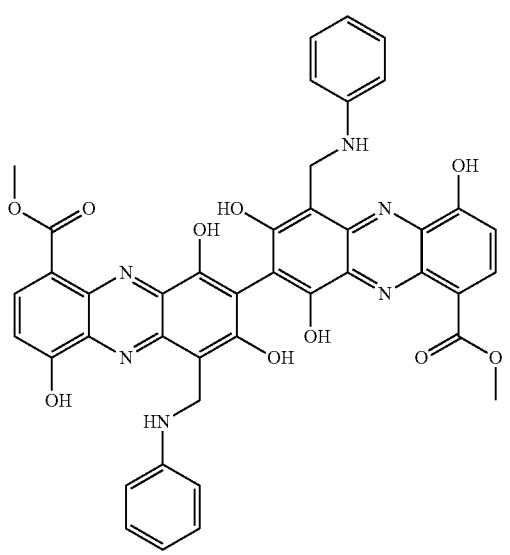 [SMILES: COC(=O)c1ccc(O)c2nc3c(CNc4ccccc4)c(O)c(-c4c(O)c(CNc5ccccc5)c5nc6c(O)ccc(C(=O)OC)c6nc5c4O)c(O)c3nc12]

dimethyl 1,1',3,3'6,6'-hexahydroxy-4,4'-bis(pyrrolidin-1-ylmethyl)-[2,2'-biphenazine]-9,9'-dicarboxylate (II-13);

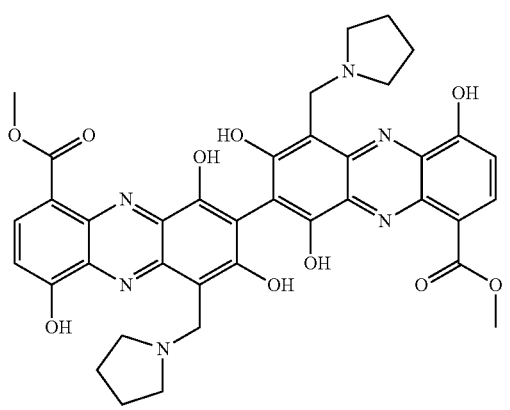 [SMILES: COC(=O)c1ccc(O)c2nc3c(CN4CCCC4)c(O)c(-c4c(O)c(CN5CCCC5)c5nc6c(O)ccc(C(=O)OC)c6nc5c4O)c(O)c3nc12]

dimethyl 4,4'-bis(((cyclopropylmethyl)-1,1',3,3',6,6'-hexahydroxy-[2,2'-biphenazine]-9,9'-dicarboxylate (II-14);

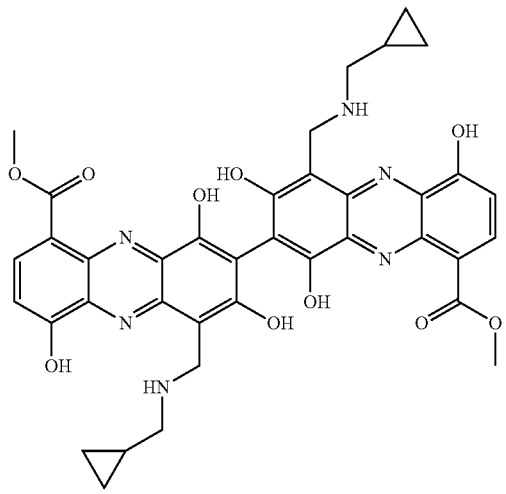 [SMILES: COC(=O)c1ccc(O)c2nc3c(CNCC4CC4)c(O)c(-c4c(O)c(CNCC5CC5)c5nc6c(O)ccc(C(=O)OC)c6nc5c4O)c(O)c3nc12]

dimethyl 1,1',3,3',6,6'-hexahydroxy-[2,2'-biphenazine]-9,9'-dicarboxylate (II-15);

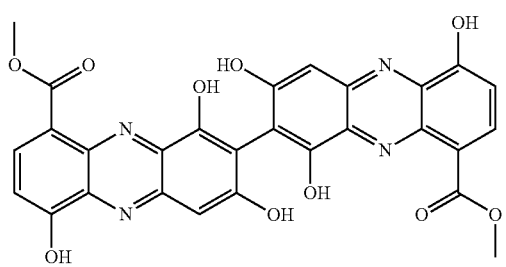 [SMILES: COC(=O)c1ccc(O)c2nc3cc(O)c(-c4c(O)cc5nc6c(O)ccc(C(=O)OC)c6nc5c4O)c(O)c3nc12]

dimethyl 4,4'-bis(aminomethyl)-1,1',3,3',6,6'-hexahydroxy-[2,2'-biphenazine]-9,9'-dicarboxylate (II-16);

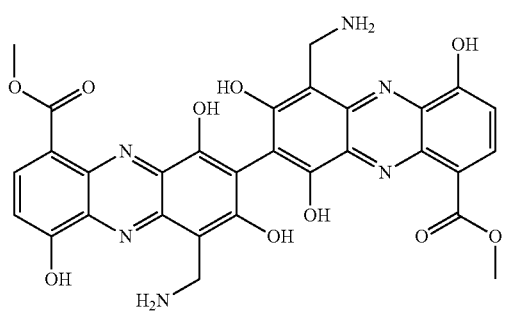 [SMILES: COC(=O)c1ccc(O)c2nc3c(CN)c(O)c(-c4c(O)c(CN)c5nc6c(O)ccc(C(=O)OC)c6nc5c4O)c(O)c3nc12]

dimethyl 4,4'-bis(acetamidomethyl)-1,1',3,3',6,6'-hexahydroxy-[2,2'-biphenazine]-9,9'-dicarboxylate (II-17);

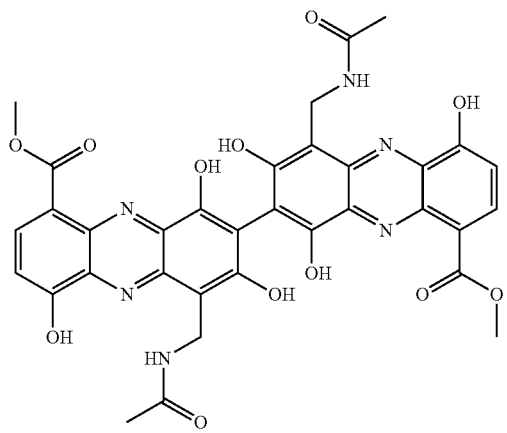 [SMILES: COC(=O)c1ccc(O)c2nc3c(CNC(C)=O)c(O)c(-c4c(O)c(CNC(C)=O)c5nc6c(O)ccc(C(=O)OC)c6nc5c4O)c(O)c3nc12]

dimethyl 4,4'-bis(benzamidomethyl)-1,1',3,3',6,6'-hexahydroxy-[2,2'-biphenazine]-9,9'-dicarboxylate (II-18);

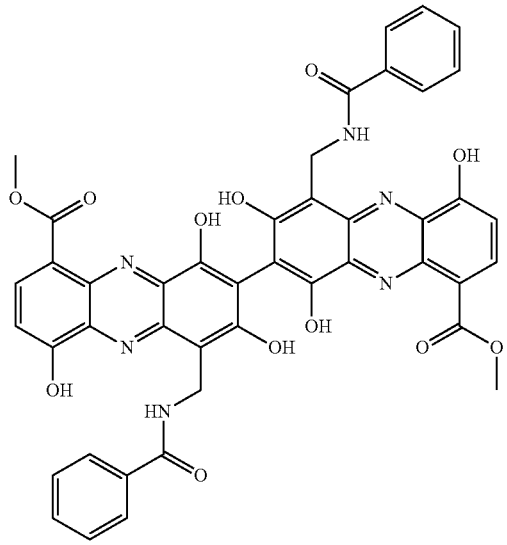 [SMILES: COC(=O)c1ccc(O)c2nc3c(CNC(=O)c4ccccc4)c(O)c(-c4c(O)c(CNC(=O)c5ccccc5)c5nc6c(O)ccc(C(=O)OC)c6nc5c4O)c(O)c3nc12]

N9,N9'-dibenzyl-1,1',3,3',6,6'-hexahydroxy-4,4'-bis(hydroxymethyl)-[2,2'-biphenazine]-9,9'-dicarboxamide (II-21);

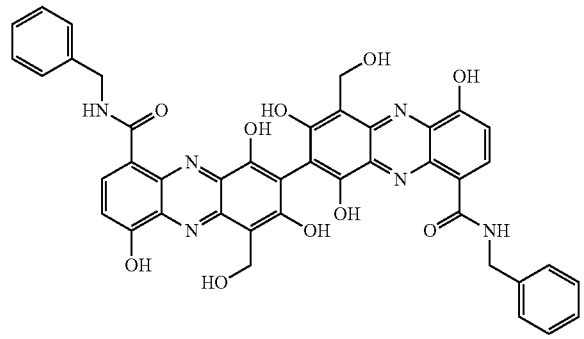 [SMILES: O=C(NCc1ccccc1)c1ccc(O)c2nc3c(CO)c(O)c(-c4c(O)c(CO)c5nc6c(O)ccc(C(=O)NCc7ccccc7)c6nc5c4O)c(O)c3nc12]

1,1',3,3',6,6'-hexahydroxy-4,4'-bis(hydroxymethyl)-N9,N9'-bis(2-phenylpropyl)-[2,2'-biphenazine]-9,9'-dicarboxamide (II-22);

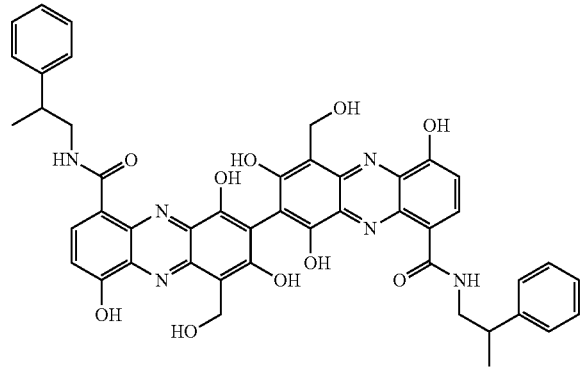 [SMILES: CC(CNC(=O)c1ccc(O)c2nc3c(CO)c(O)c(-c4c(O)c(CO)c5nc6c(O)ccc(C(=O)NCC(C)c7ccccc7)c6nc5c4O)c(O)c3nc12)c1ccccc1]

1,1',3,3',6,6'-hexahydroxy-4,4'-bis(hydroxymethyl)-N9,N9'-diisobutyl-[2,2'-biphenazine]-9,9'-dicarboxamide (II-23);

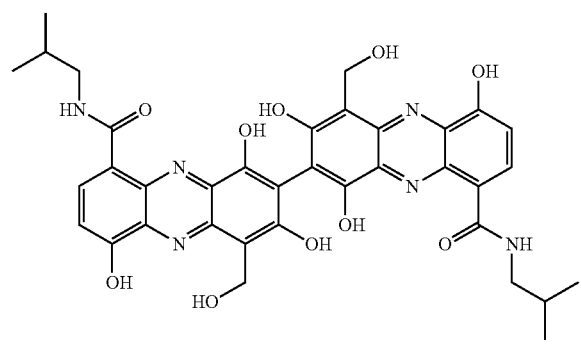 [SMILES: CC(C)CNC(=O)c1ccc(O)c2nc3c(CO)c(O)c(-c4c(O)c(CO)c5nc6c(O)ccc(C(=O)NCC(C)C)c6nc5c4O)c(O)c3nc12]

1,1',3,3',6,6'-hexahydroxy-4,4'-bis(hydroxymethyl)-N9,N9'-diisopropyl-[2,2'-biphenazine]-9,9'-dicarboxamide (II-24); and

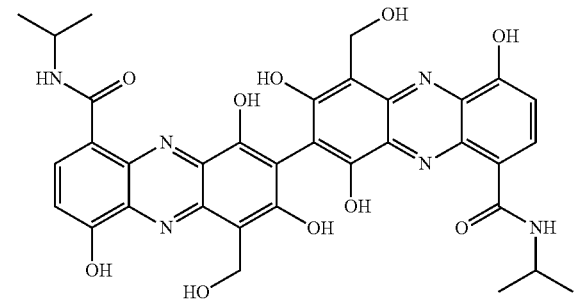 [SMILES: CC(C)NC(=O)c1ccc(O)c2nc3c(CO)c(O)c(-c4c(O)c(CO)c5nc6c(O)ccc(C(=O)NC(C)C)c6nc5c4O)c(O)c3nc12]

1,1',3,3',6,6'-hexahydroxy-4,4'-bis(hydroxymethyl)-N9,N9'-dimethyl-[2,2'-biphenazine]-9,9'-dicarboxamide (II-25).

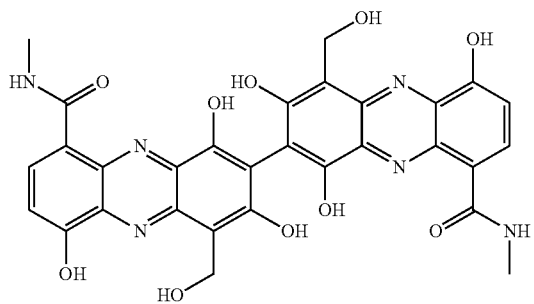 [SMILES: CNC(=O)c1ccc(O)c2nc3c(CO)c(O)c(-c4c(O)c(CO)c5nc6c(O)ccc(C(=O)NC)c6nc5c4O)c(O)c3nc12]

Methods of Making

Examples of synthetic pathways useful for making compounds described herein are set forth in the Examples below and in Schemes I-VII.

Scheme I

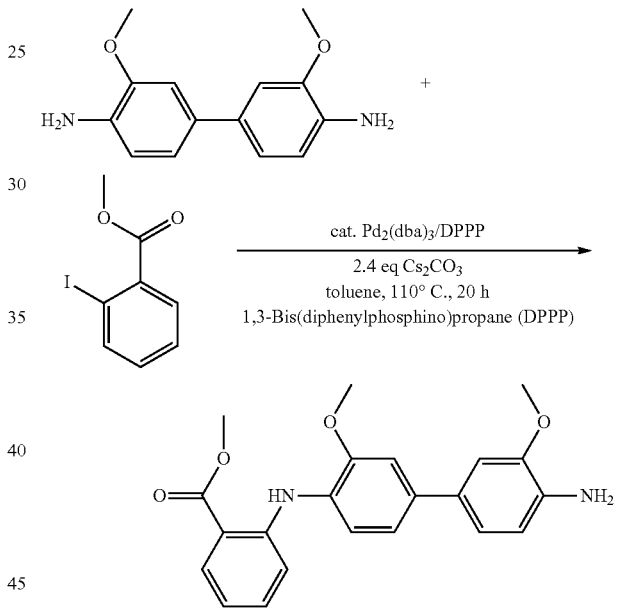

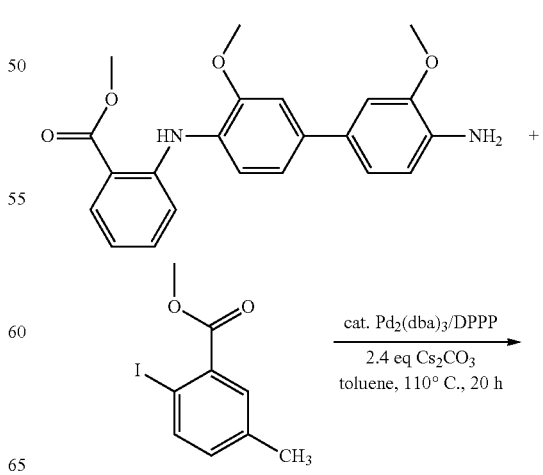

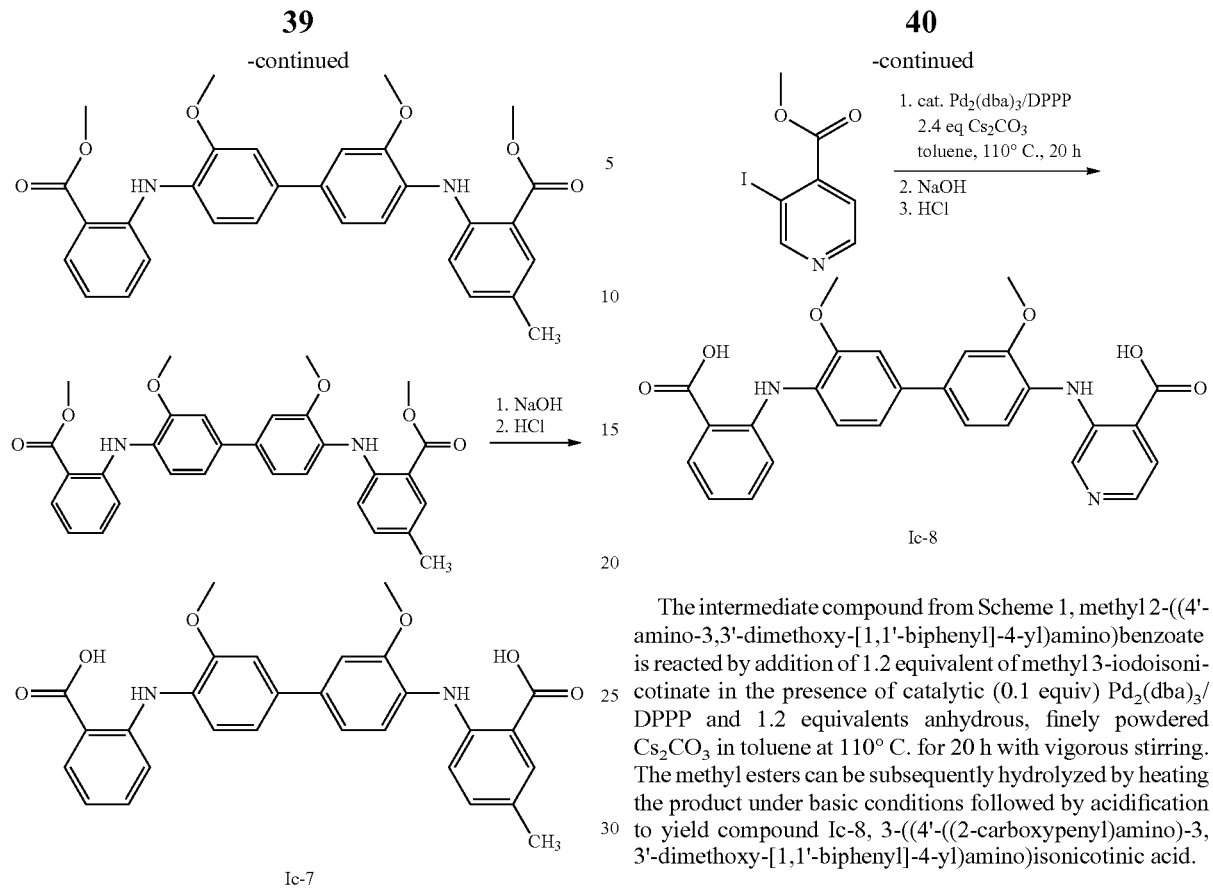

The intermediate compound from Scheme 1, methyl 2-((4'-amino-3,3'-dimethoxy-[1,1'-biphenyl]-4-yl)amino)benzoate is reacted by addition of 1.2 equivalent of methyl 3-iodoisonicotinate in the presence of catalytic (0.1 equiv) Pd$_2$(dba)$_3$/DPPP and 1.2 equivalents anhydrous, finely powdered Cs$_2$CO$_3$ in toluene at 110° C. for 20 h with vigorous stirring. The methyl esters can be subsequently hydrolyzed by heating the product under basic conditions followed by acidification to yield compound Ic-8, 3-((4'-((2-carboxypenyl)amino)-3,3'-dimethoxy-[1,1'-biphenyl]-4-yl)amino)isonicotinic acid.

Compound Ic-7 can be synthesixed by reacting commercially available 3,3'-dimethoxy-[1,1'-biphenyl]4,4'-diamine (1 equivalent) with 1.2 equivalents of the commercially available methyl ester of iodobenzoic acid in the presence of Pd$_2$(dba)$_3$/DPPP (0.1-0.5 equiv) and 1.2 equivalents Cs$_2$CO$_3$ in toluene at 110° C. for 20 h with vigorous stirring. The intermediate compound methyl 2-((4'-amino-3,3'-dimethoxy-[1,1'-biphenyl]-4-yl)amino)benzoate is isolated by flash chromatography on a C18 column. The product is then reacted by addition of 1.2 equivalent of methyl 2-iodo-5-methylbenzoate in the presence of catalytic (0.1-0.5 equiv) Pd$_2$(dba)$_3$/DPPP and 1.2 equivalents anhydrous, finely powdered Cs$_2$CO$_3$ in toluene at 110° C. for 20 h to yield methyl 2-((3,3'-dimethoxy-4'-((2-(methoxycarbonyl)phenyl)amino)-[1,1'-biphenyl]-4-yl)amino)-5-methylbenzoate. The methyl esters can then be hydrolyzed under basic conditions followed by acidification to yield compound Ic-7, 2-((4'-((2-carboxyphenyl)amino)-3,3'-dimethoxy-[1,1'-biphenyl]-4-yl)amino)-5-methylbenzoic acid.

Scheme II

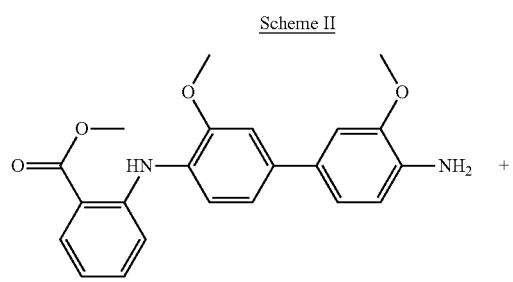

Scheme III

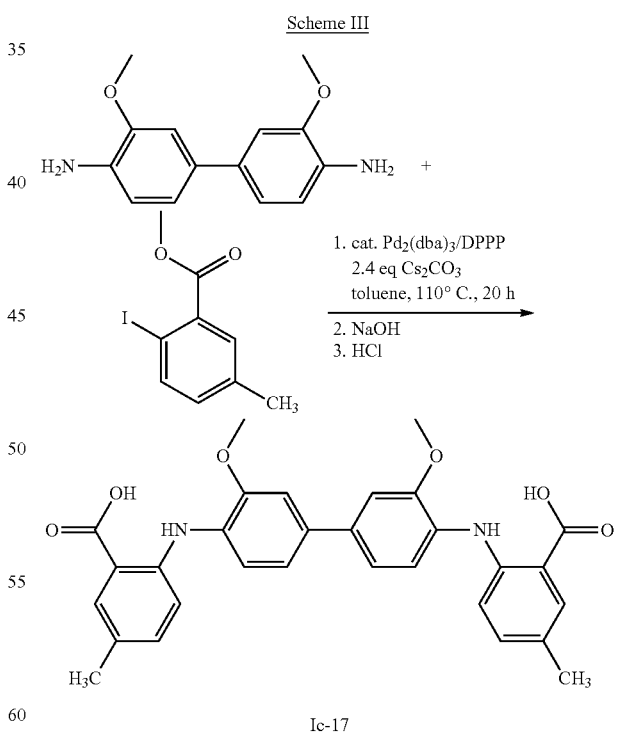

The compound Ic-17 can be synthesized by reacting commercially available 3,3'-dimethoxy-[1,1'-biphenyl]-4,4'-diamine (1 equivalent) with 2.4 equivalents of the commercially available methyl 2-iodo-5-methylbenzoate in the presence of Pd$_2$(dba)$_3$/DPPP (0.1-0.5 equiv) and 2.4 equivalents anhydrous, finely powdered $Cs_2CO_3$ in toluene at 110° C. for 20 h with vigorous stirring. The methyl esters can be subsequently hydrolyzed by heating the product under basic conditions followed by acidification to yield compound Ic-17.

Scheme IV

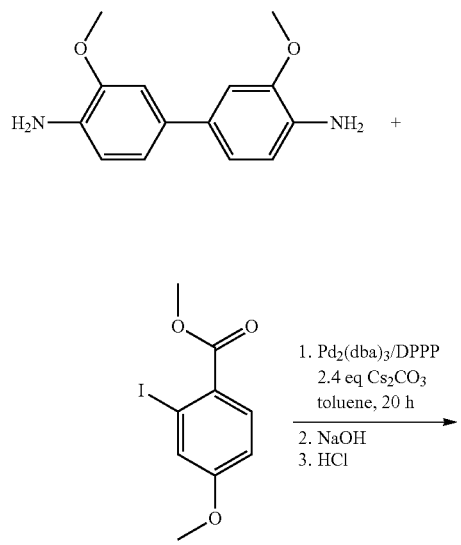

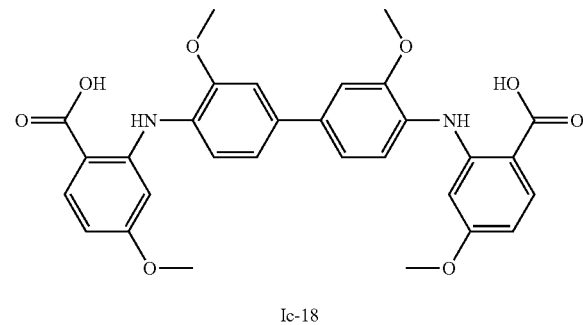

Ic-18

The compound Ic-18 can be synthesized by reacting commercially available 3,3'-dimethoxy-[1,1'-biphenyl]-diamine (1 equivalent) with 2.4 equivalents of the commercially available methyl 2-iodo-4-methoxybenzoate in the presence of $Pd_2(dba)_3$/DPPP (0.1-0.5 equiv) and 2.4 equivalents anhydrous, finely powdered $Cs_2CO_3$ in toluene at 110° C. for 20 h with vigorous stirring. The methyl esters can be subsequently hydrolyzed by heating the product under basic conditions followed by acidification to yield compound Ic-18.

Scheme V

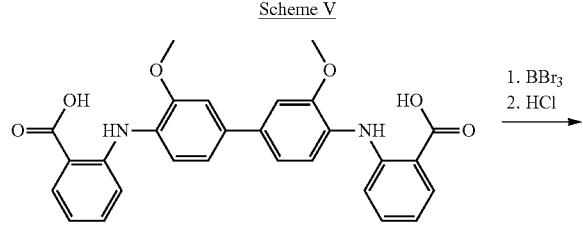

-continued

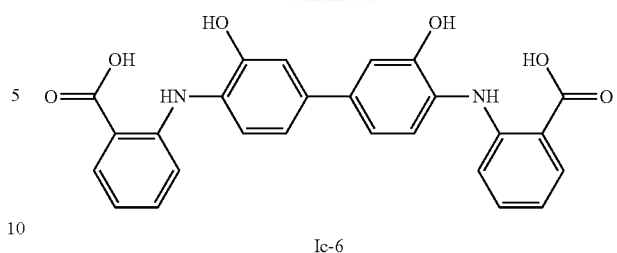

Ic-6

Compound Ic-6 can be prepared by treating 0.2 mmol of the commercially available starting material 2,2'-((3,3'-dimethoxy-[1,1'-biphenyl]-4,4'-diyl)bis(azanediyl))dibenzoic acid in a stirred solution of anhydrous $CH_2Cl_2$ (10 mL) at −78° C. with a 20-fold excess of $BBr_3$ (4 mmol), added dropwise, for 1 h. The solution is then warmed to room temperature for 1 h. The reaction is quenched by slowly adding 10 mL of an ice cold solution of 6 M HCl to the mixture and stirring at room temperature for 1 h. The aqueous layer is extracted with $CH_2Cl_2$ (3×50 mL), and the combined organic layers are dried over $MgSO_4$. The solvent is concentrated in vacuo and the residue is purified on a C18 column eluted with a linear gradient from 5% acetonitrile 0.1% TFA to 100% acetonitrile/0.1% TFA.

Scheme VI

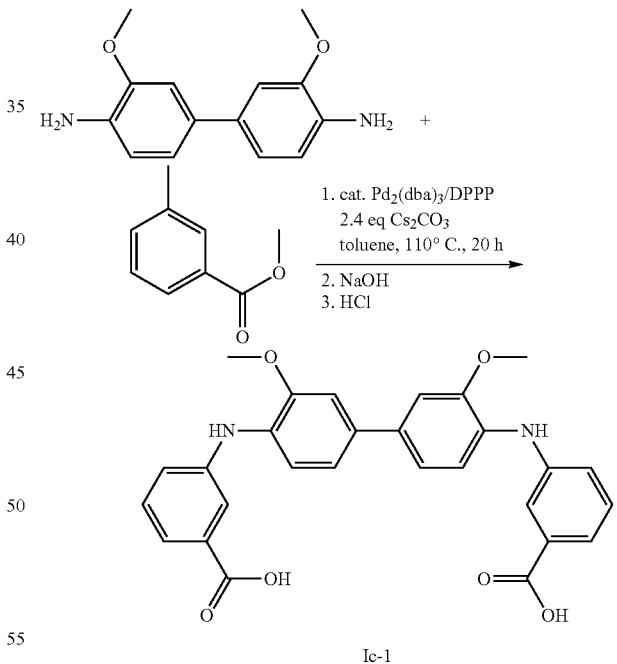

Ic-1

The compound Ic-1 can be synthesized by reacting commercially available 3,3'-dimethoxy-[1,1'-biphenyl]-4,4'-diamine (1 equivalent) with 2.4 equivalents of the commercially available methyl 2-iodo-5-methylbenzoate in the presence of $Pd_2(dba)_3$/DPPP (0.1-0.5 equiv) and 2.4 equivalents anhydrous, finely powdered $Cs_2CO_3$ in toluene at 110° C. for 20 h with vigorous stirring. The methyl esters can be subsequently hydrolyzed by heating the product under basic conditions followed by acidification to yield compound Ic-1.

Scheme VII

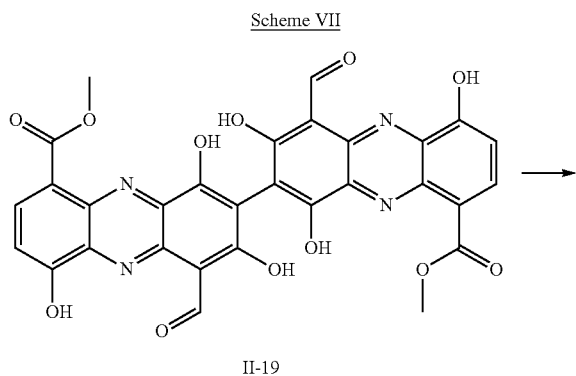

II-19

↓

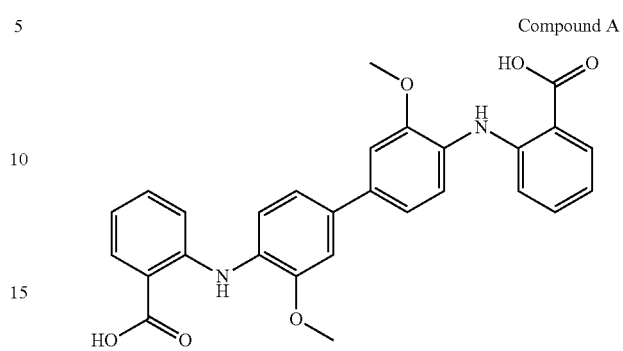

II-20

The compound II-19 (prepared as described in Example 1) is converted to the alcohol form II-20 by dissolving the starting material in DMSO and treating the compound with 10 equivalents of NaCNBH$_3$ for 24 h at room temperature. The product is purified by reverse phase chromatography on a C18 column eluted with a linear gradient from 5% acetonitrile 0.1% TFA to 100% acetonitrile/0.1% TFA.

Methods of Using

The invention relates to treating hematological malignancies with pharmaceutical compositions comprising one or more compounds of Formula Ia', Ib', Ic', or II', and/or BH3 mimic compounds that inhibit a broad range of the Bcl-2 family of proteins, most notably Mcl-1. It is contemplated that the activity against the protein Mcl-1 of the compounds A or II-19 (FIGS. 1-7) as well as derivative compounds will enable therapeutic utility of these compounds as anti-tumor agents in treating cancer, including blood cancers.

The invention, for example, provides a method for treating particular types of hematopoietic cancers, using pharmaceutical compositions comprising BH3 mimic compounds of Formula Ia', Ib', Ic', or II'. The use of these compounds for particular types of hematopoietic cancers may have unexpected results in terms of efficacy and/or ability to inhibit particular anti-apoptotic (pro-survival) members of the Bcl-2 family or to mimic particular members of the pro-apoptotic Bcl-2 family proteins. Accordingly, hematological tumor cells that are hyper-dependent on a particular member of the Bcl-2 family of proteins will be most affected by that BH3 mimic which targets that protein.

Compound A is also known as redoxal which has the following structure:

Compound A

Compound A may be particularly useful in a method of treating hematopoietic cancers, by preferentially inhibiting the binding of the activator BH3 only proteins of the Bcl-2 family to protein Mcl-1. This level of activity (<500 nM) is among the most potent of all reported BH3 mimics and directs the use of this compound in treating certain hematological malignancies that are affected principally by the Bcl-2 family proteins and among those proteins, mostly by Mcl-1. Based, on the unique ability of compound A to inhibit BIO binding to Mcl-1, this compound may be particularly effective in blocking the unwanted cell survival activity of Mcl-1 in tumorogenic lymphoid and myeloid cells. This feature of compound A will direct its use as a potential therapeutic agent for treating Multiple Myeloma (MM), diffuse large B-cell lymphoma (DLBCL), chronic lymphocytic leukemia (CLL), acute myelogenous leukemia (AML), all of which are effected by elevated Mcl-1. Compound II-19 exhibits surprisingly high affinity against Mcl-1 (IC$_{50}$=7 nM) aud Bcl-xL. (IC$_{50}$=15 nM) and this level of activity makes it the most potent of small, molecule (non-peptide) BH3 mimetics reported to date. This potent activity directs its use in treating certain hematological malignancies that are affected by Bcl-2 family proteins that include Mcl-1, Bcl-xL, or the closely protein related Bcl-2, Similarly, activity in derivatives of compound A, compounds of Formula Ia, Ib, Ic, as well as compounds of Formula II, may direct the use of those compounds in treating lymphoid and myeloid malignancies.

Methods of treatment of hematopoietic cancers in patients using pharmaceutical compositions comprising compounds of Formula Ia', Ib', Ic', or II' are provided. These compounds have broad activity against all Bcl-2 family proteins, most notably including Bcl-2 protein family member Mcl-1, which is not expected. Accordingly, one aspect of this invention is directed to a method for treating hematopoietic cancers, such as Multiple Myeloma, by preferentially targeting Bcl-2 protein family member Mcl-1 with a member of the group consisting of pharmaceutical compositions comprising compounds of Formula Ia', Ib', Ic', or II'.

Methods for tumor regression and enhancing survival, in B-cell lymphomas in patients by administering pharmaceutical compositions comprising a compound of Formula Ia', Ib', Ic', or II' are provided. Accordingly, in one embodiment, this invention describes a method for using compounds of Formula Ia, Ib, and Ic for the treatment of non-Hodgkin's B-cell lymphoma, including CLL, Burkett's, Indolent and Aggressive non-Hodgkin's lymphomas, Multiple Myelomas, or other cancers that are affected by Bcl-2 family of proteins, and in particular the protein Mcl-1.

These treatments may be accomplished utilizing pharmaceutical compositions comprising a compound of Formula Ia', Ib', Ic', or II' alone or in combination with other chemotherapy agents or with radiation therapy. Accordingly, the invention provides a method for treating particular types of hematopoietic cancers using a combination of one or more compounds selected from the group consisting of pharmaceutical compositions comprising a compound of Formula Ia', Ib', Ic', or II', in combination with other therapies, for example, a class of therapeutics known as 26S proteosome inhibitors, such as, for example, Bortezomib (Velcade®).

In addition, this invention relates to methods for determining selectivity of compounds of Formula Ia', Ib', Ic', or II' and BH3 mimic compounds to predict efficacy in treating hematological and other malignancies involving Bcl-2 family proteins. For example, these compounds can have varying potencies in inhibiting BH3 mediated-binding of particular Bcl-2 family proteins, and the difference in potency can be identified by systematically ordering combinations of protein-protein interactions and comparing the blocking activity of BH3 mimic compounds to that of competing BH3 domain-containing peptides. By matching the activity of the compound to a particular BH3 domain peptide, a biological activity can be assigned to that compound that correlates to the activity of the BH3 domain-containing protein. This information can be used to predict the utility of a BH3 mimic compounds in treating a particular disease.

This invention also relates to cancer treatments and especially to Multiple Myeloma treatments directed to Bcl-2 and Bcl-xL and Mcl-1 and Bcl-2A1 and Bcl-w (referred as a group as an anti-apoptotle Bcl-2 family) activity.

A. Treatment with Compounds of Formula Ia', Ib', Ic', or II' to inhibit Bcl-2 protein.

The present invention describes anti-tumor efficacy and enhanced survivability in mouse models for hematological malignancies by treatment with pharmaceutical compositions comprising one or more compounds of Formula Ia', Ib', Ic', or II'. Efficacy in certain animal models may be transferable to humans afflicted with B-cell lymphoma or other hematological or non-hematological cancers affected, by Bcl-2 family proteins.

This treatment could be administered as a stand-alone therapy or with prior art chemotherapy agents or with radiation therapy. In one embodiment, the pharmaceutical compositions comprising compounds of Formula Ia', Ib', Ic', or II', are used for the treatment of B-cell lymphoma or Multiple Myeloma by inducing cancer cell death and preventing cancer cell, migration, to spleen or lymph nodes.

Because Mcl-1 has emerged as a key member of the Bcl-2 family of proteins for initiating and maintaining certain. Myeloid as well as B-cell and T-cell malignancies, it is an important target for treatment of many hematological diseases. This Invention, demonstrates the effectiveness-of the compound A in inhibiting BH3 binding to Mcl-1. It is taught that this feature of compound A is useful, for treating Multiple Myeloma, B-cell lymphoma or other hematological cancers or other disease that are affected by Mcl-1 activity including prostate, liver, and ovarian cancers.

Compounds of Formula Ia', Ib', Ic', or II' have activity against Mcl-1. Accordingly, compounds of Formula Ia', Ib', Ic', or II' and pharmaceutical compositions comprising a compound of Formula Ia', Ib', Ic', or II' are useful therapeutic compounds in treating MM, NHL, CLL, AML, prostate, liver and ovarian, cancers, and melanomas.

This activity will also direct the use of these compounds for treatment of certain autoimmune diseases that are affected by excess B or T cell proliferation.

Data described in the examples below indicate that compound A has unique capability to preferentially disrupt binding of Bim BH3 peptides to purified Mcl-1 in comparison to Bcl-xL protein in an in vitro assay. An experiment reported below used Fluorescence polarization (FP) to assess the concentration of compound A or compound II-19 that causes 50% inhibition ($IC_{50}$) of Bim BH3 binding to Mcl-1 (Example 1). Binding of peptides consisting of the BH3 binding domain of the pro-apoptotic protein Bak to purified Human Bcl-xL or Human Mcl-1 was carried out in the presence of titrated compound A, or compound II-19. (Degterev et al. (2002) Nat. Cell Biol. 3; 173-82). These compounds were effective at blocking Bim binding to Bcl-xL. However, each is more effective at binding of Mcl-1 and demonstrated lower $IC_{50}$. This preferred sensitivity of Mcl-1 for compounds A, or compound II-19, indicates that these compounds have novel characteristics that make them uniquely valuable as anti-tumor therapeutics. This activity of compounds of Formula Ia', Ib', Ic', or II' in inhibiting BH3 mediated binding to Mcl-1 has not been, reported in the literature.

The present invention relates to the use of pharmaceutical compositions comprising a compound of Formula Ia', Ib', Ic', or II' as compositions in inhibiting the activity of Bcl-2 pro-survival proteins, most particularly Mcl-1, in tumor cells and thereby killing those cells. The ability of these compounds to inhibit Mcl-1 function in cells makes these compounds effective anti-B-cell, T-cell, and Myeloma cell, cancer therapeutics for treating non-Hodgkin's lymphoma, CLL, MM and AML as well as prostate, colon, ovarian, and liver cancer and melanoma.

Compounds of Formula Ia', Ib', Ic', or II', cause tumor regression, for example by killing a cancer cell, and increased survival in several, mouse tumor models, including, for example models for diffuse large B-cell lymphoma (DLBCL) (Cattoreiti et al. (2005) Cancer Cell 7: 445-55), small B cell lymphoma/CLL (Zapata et al. (2004) Proc. Natl. Acad. Sci USA 101.(47); 16600-5) and migrating B-cell lymphomas (Refaeli et al. (2005) Proc. Natl, Acad. Sci, USA-102(11): 4097-102), as well, as an AML mouse tumor model (Lopes de Menezes et al (2005) Clin. Canc. Res. 11(14): 5281.-91). All of the tumors from these cell models are characterized as having elevated pro-survival Bcl-2 family proteins, including Bcl-2, Bcl-xL, and Mcl-1.

Accordingly, the present invention relates to the use of pharmaceutical compositions comprising a compound of Formula Ia', Ib', Ic', or II' in affecting tumor regression in human lymphoid and myeloid cancers. These compounds are effective in inducing apoptosis selectively in hematological cancers due to the hyper-dependence of lymphoid and myeoid-derived tumor cells on the activity of the Bcl-2 family anti-apoptotic proteins.

The Bcl-2 protein is a member of an entire family, the Bcl-2 family of proteins, that have structurally similar genes and that share sequence homology and participate in the control of programmed cell death or "apoptosis" (Corey et al. (2002) Nat. Rev. Cancer 2: 647-656). Some members of this family (anti-apoptotic Bcl-2 family proteins), such, as Bcl-2 Bcl-xL, BcL-w, Bfl-1(A1) and Mcl-1, protect cells from apoptosis. These proteins share sequence homology in 4-helical regions called the Bcl-2 homology (BH)-domains 1-4 (BH1-BH4). Another class of this family (pro-apoptotic Bcl-2 proteins), such as Bax and Bak, promote apoptosis and share three of these domains, BH1-BH3. A third class of Bcl-2 family proteins, such as Bim, Bad, Hrk, Bid, Puma, Noxa, and Bmf, share only one region, the BH3 domain, and are referred to as "BH3-only proteins". The BH3-only proteins are pro-apoptotic, and like Bax and Bak, the BH3-only proteins require an intact BH3 domain to promote apoptosis (Adams et al. (1998) Science 281; 1322-26).

A complex interplay of the pro-apoptotic and anti-apoptotic proteins affects the integrity of the outer membrane of the mitochondria (Green et al. (2004) Science 305; 626-29) either causing or preventing the release of certain molecules that activate the cysteine aspartyl proteases (caspases). The caspases are the eventual effectors of apoptosis (Salvesen (2002) Cell Death and Differentiation 9: 3-5). Bax and Bak are essential for release of these apoptosis promoting molecules from, the mitochondria (Wei et al. (2001) Science 292: 727-30). The BBS-only proteins stimulate the activity of Bax and Bak while the anti-apoptotic proteins oppose their activity. Essentially all of these interactions occur by BH3 domain mediated binding (Chrittenden et al. (1995) EMBO J. 14;5589-96).

Anti-apoptotic family members Bcl-2, Bcl-xL and Mcl-1 are over-expressed in many types of careers, including lymphomas, melanomas, myelomas, and cancer in prostate and colon (Kitada et al. (2002) Oncogene 21; 3459-74; Paul-Samojedny et al. (2005) Biochem Biophys, Acta, 1741(1-2); 25-9; Pollack et al. (2003) Cancer 97(7); 1630-8; Tas et al. (2004) Melanoma Res. 14(6); 543-6). Animal model studies established that the continuous presence of anti-apoptotic family members is required for tumor survival and growth. Additionally, the pro-survival Bcl-2 proteins are Important for the development of resistance of tumor cells to chemotherapies such as DNA damaging agents. The ratio of pro-apoptotic to anti-apoptotic family members has been, shown. In many cases to hold significant prognostic value for patient outcome. Over-expression of anti-apoptotic Bcl-2 family proteins has been reported in many of the hematopoietic malignancies. For example, increased expression of Bcl-2 protein that results from a translocation (t14; 18) of the BCL2 gene occurs in 80% to 90% of low-grade follicular non-Hodgkin lymphomas (NHLs) (Kitada et al. (2002) supra).

Three different strategies for countering the tumorigenic effects of anti-apoptotic Bcl-2 family proteins in NHL, CLL, MM, and other types of cancer include: (1) inhibiting gene transcription; (2) using ants sense oligonucleotides to cause mRNA degradation; and (3) directly inhibiting the proteins with small-molecule drugs (reviewed in Reed et al. (2005) Blood 106; 408-418).

One of the desired characteristics of anti-tumor drugs is the ability to induce apoptosis in tumor cells and not in healthy cells. The conventional chemotherapy is mostly based, on the evidence that proliferating cells are more sensitive to anticancer agents than non-dividing cells (Marchini et al. (2004) Curr. Med. Chem. Anticancer Agents 4(3): 247-6). For instance, generally tumor cells are more sensitive to apoptosis induction by microtubule poisons such as taxol and DNA damaging drugs such as doxorubicin than healthy cells (Abal et al. (2003) Curr. Cancer Drug Targets 3(3); 193-203).

However, in many types of cancer, certain of the anti-apoptotic Bcl-2 family proteins are elevated which causes cells to be less responsive to such drugs. This is especially true in B-cell lymphomas and other hematological malignancies. In these cancers elevated levels of anti-apoptotic Bcl-2 family proteins correlate highly with the onset, maintenance of the disease state, and chemoresistance (Kitada et al. (2002) supra).

However, it was reported that cells over-expressing Bcl-xL exhibited increased sensitivity to an antimycin-A derivative compound that binds to and inhibits Bcl-2 and Bcl-xL (Manion et al. (2004) J. Biol. Chem. 279(3): 2159-65; Kim et at (2001) Biochemistry 40: 4911-22). This finding has implications for the use of certain BH3 mimics as anti-tumor therapeutic compounds given that over-expression of Bcl-xL or Bcl-2 results in a general decrease in responsiveness to apoptotic cues and. has been implicated in multi-drug resistance in cancer cells and carcinogenesis.

An understanding of the mechanisms for this observed change in response to Bcl-2 or Bcl-xL targeted compounds has been described (Letai (2005) J. Clin. Invest. 115: 2648-55). In that report it was argued that the cell context in which elevated anti-apoptotic Bcl-2 proteins are found determines the occurrence or the degree of "sensitization" to apoptotic cues. Most notably, it is the presence of BH3-only proteins bound to these anti-apoptotic proteins that cause sensitization to apoptotic cues. For Instance, the presence of the BH3-only protein Bad (Bcl-2 associated death promoter) bound to Bcl-2 or Bcl-xL sensitizes rather than kills cells, as is the case when the BH3-only protein Bim (Bcl-2-like 11) binds (Letai et al. (2002) Cancer Cell 2(3): 183-92). Other arguments have been put forth that describe "hyper-dependence" on certain elevated anti-apoptotic Bcl-2 proteins in certain, tumor cells (Kim et al. (2001) Biochemistry 40: 4911-22).

The functions that the individual Bcl-2 family proteins have during hematopoicsis have been demarcated genetically using transgenic mice. For example, mice deficient in Bcl-2 have no overt problems during lymphocyte differentiation but do have excess apoptosis in peripheral lymphocytes after antigenic stimuli (Veis et al. (1993) Cell 75: 229). Bcl-xL deficient mice are also viable but do show late maturation of erythroid cells (Wagner et al. (2000) Development 127: 4949-58).

Mcl-1 deficiency has a pronounced, perhaps principal role, in lymphocyte survival. Conditional knockouts have been used, to determine the role of Mcl-1 in hematopoicsis and lymphocyte survival. It was determined that conditional deficiency of Mcl-1 results in apoptosis of differentiating lymphocytes and stops development of pre-B-cell and double negative T-cells as well as apoptosis in mature B and T lymphocytes (Rinkenberger et al (2000) Genes Dev. 14: 23). These findings demonstrate a role for the anti-apoptotic form of Mcl-1 in the development and survival of B and T lymphocytes. These findings also indicate that Mcl-1 may be an ideal, target for treating excess growth of lymphoid cells.

The clinical implication is underscored by the observation that elevated Mcl-1 expressed in its active anti-apoptotic full length form positively correlates with increasing grade of B-cell lymphomas and plasma cell myelomas (Cho-Vega et al., (2004) Hum. Pathol. 35 (9): 1095-100) as well, as chronic lymphocytic leukemia (Petlickovski et al. (2005) Blood 105: 4820-28).

Targeted gene knockouts for different pro-apoptotic BH3-only members of the Bcl-2 family members have been assessed for disease correlation. Transgenic mice deficient in Bim have extensive myeloid proliferation and autoreactive T and B cells that have lost responsiveness to apoptosis inducing drugs (Bouillet et al. (1999) Science 286: 1735-38), while mice deficient in Bad display high incidence of diffuse large cell lymphoma (Ranger et al. (2003) Proc. Natl. Acad. Sci. USA 100: 9324-29). Mice deficient in the pro-apoptotic BH3-only protein Bid demonstrated Hepatocarcinoma and a failure to respond to the death inducing cytokine fas (Yin et al. (1999) Nature 400: 886-891). Both of the pro-apoptotic BH3-only proteins Puma and Noxa were shown to be required for all p53-mediated apoptosis (Villunger et al. (2003) Science 302; 1036-1040).

Notably, conditional knockouts of the Mcl-1 gene caused profound reduction in B and T lymphocytes (Opferman et al (2003) Nature 426(6967): 671-6), which is the opposite of a deficiency in the BH3-only protein Bim and in keeping with the understanding that Mcl-1 selectively inhibits the pro-apoptotic protein Bim.

B. Combination Therapy

Embodiments of the present invention also include the combination of one or more compounds selected from the group consisting of compounds of Formula Ia', Ib', Ic', or II' with other anti-tumor agents, such as proteosome inhibitors, to yield combination, therapies. In some instances, these combination therapies may yield synergistic results as compared to the additive results of the component therapies when used alone. For example, these compounds may be particularly effective when used in combination with a class of therapeutics known as 26S proteosome inhibitors.

Compounds that have activity as 26S proteosome inhibitors have been, suggested for use as anti-tumor therapeutics based on their ability to inhibit Nf-Kb signaling (Li et al. (1995) Biophys. Biochem. Res. Com. 215: 292-301). One such compound, the FDA approved drug Bortezomib (Velcade®), has been shown to cause elevated Mcl-1 in lymphocytes (Nencioni et al. (2005) Blood 105(8): 3255-62). Elevated Mcl-1 has been shown to be causal in the establishment and maintenance of lymphoid and myeloid tumors. The unwanted side effect of elevated Mcl-1 can be rectified by inhibiting Mcl-1 using the compounds of Formula Ia', Ib', Ic', or II' will have utility in potentiating the effect of Bortezomib or other 26S proteosome inhibitors as anti-tumor therapeutics.

These observations suggest that elevated Mcl-1 may counteract Bortezomib (Velcade®) in CLL, AML, and certain NHL cells. Consistent with this, the cytotoxic effects of proteosome inhibitors are enhanced when Mcl-1 levels are contained at normal levels or reduced in a cell culture (Nencioni A et al. (2905) supra). This finding demonstrated that Mcl-1 accumulation is an unwanted molecular consequence of exposure to proteosome inhibitors.

C. Screening Methods

The present invention teaches a method tor selecting appropriate BH3 mimic compounds in treating particular tumors. This selection is based on an understanding of the unique activity of compounds of Formula Ia', Ib', Ic', or II' in mimicking particular BH3 domains. It is taught that compounds from this group that have unique activity against either all of the anti-apoptotic Bcl-2 family proteins or a particular member of this family of proteins will be the basis for use against particular tumors. Expression levels of particular Bcl-2 family proteins cart be assessed using standard assays, western blot, or immunohistoiogical staining of biopsied turner tissue. Following this assessment, compounds with activity against the elevated proteins in the tumor sample will be selected as appropriate therapeutics for treating that tumor.

It is of particular interest to establish the correlation of Mcl-1 expression levels to the occurrence of tumors. Based on the discovery that compounds A or II-19 inhibit Mcl-1 binding (see Example 2 and Example 3 below), it may be that cells that are hyper-dependent on Mcl-1, as a consequence of elevated Mcl-1, or elevated levels of Mcl-1 completed with Bim Bid or Noxa, in the disease state, will be sensitized to compounds of Formula Ia', Ib', Ic', or II' other BH3 mimic compounds that arc shown to inhibit Mcl-1.

D. Administration and Dosage i. Routes of Administration

The pharmaceutical compositions comprising a compound of Formula Ia', Ib', Ic', or II' can be administered by any known administration method known to a person skilled in the art. Examples of routes of administration include but are not limited to oral, parenteral, intraperitoneal, intravenous, intraarterial, transdermal, topical, sublingual, intramuscular, rectal, transbuccal, intranasal, liposomal, via inhalation, vaginal, intraoccular, via local delivery by catheter or stent, subcutaneous, intraadiposal, intraarticular, intrathecal, or in a controlled or extended release dosage form. The pharmaceutical compositions comprising a compound of Formula Ia', Ib', Ic', or II' can be administered in accordance with any dose and dosing schedule that achieves a dose effective to treat disease.

The route of administration of pharmaceutical compositions comprising a compound of Formula Ia', Ib', Ic', or II' can be independent of the route of administration of any additional anti-cancer agents that are used. Thus, at least one of the compounds of Formula Ia', Ib', Ic', or II' can be administered, for example, orally or by intravenous delivery while another compound or other agent (anti-cancer agent) can be administered, for example, orally, parenterally, intraperitoneally, intravenously, intraarterially, transdermally, sublingually, intramuscularly, rectally, transbucally, intranasally, liposomally, via inhalation, vaginally, intraoccularly, via local delivery by catheter or stent, subcutaneoasly, intraadiposally, intraarticularly, intrathecally, or in a controlled or extended release dosage form.

As examples, the compounds of the invention can be administered in oral forms, for example, as tablets, capsules (each of which includes sustained release or timed release formulations), pills, powders, granules, elixirs, tinctures, suspensions, syrups, and emulsions. Likewise, the compounds can be administered by intravenous (e.g., bolus or infusion), intraperitoneal, subcutaneous. Intramuscular, or other mutes using forms well known to those of ordinary skill in the pharmaceutical arts. Particularly useful routes of administration of the compounds are oral administration and intravenous delivery.

The compounds can also be administered in the form of a depot injection or implant preparation, which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example. Silastic, silicone rubber or other polymers manufactured by the Dow-Corning Corporation.

The compounds can also be delivered by the use of monoclonal antibodies as individual carriers to which the compound molecules are coupled.

The compounds can also be prepared with soluble polymers as targetable drug carriers. Such, polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds can be prepared with biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthioesters, polyacetals, polydihydropyrans, polycyanoacrylates and cross linked or araphipathic block copolymers of by hydrogels.

In a specific embodiment, the compounds can be administered orally in a gelatin capsule, which can comprise excipients such as microcrystalline cellulose, crosearmellose sodium and magnesium stearate. For example, an embodiment can include 200 mg of solid compound with 89.5 mg of macrocrystalline cellulose, 9 mg of sodium croscarmellose, and 1.5 mg of magnesium, stearate contained in a gelatin capsule.

ii. Dosages and Dosage Schedules

The dosage regimen utilizing the compounds of Formula Ia', Ib', Ic', or II' can be selected in accordance with a variety of factors including type, species, age, weight, and sex of the patient; the type of disease being treated; the severity (i.e., stage) of the disease to be treated; the route of administration; the renal and hepatic function of the patient; and the particular compound or salt thereof employed. A dosage regimen can be used, for example, to prevent, inhibit (fully or partially), or arrest the progress of the disease.

In accordance with the invention, pharmaceutical compositions comprising a compound of Formula Ia', Ib', Ic', or II' can be administered by continuous or intermittent dosages. For example, intermittent administration of pharmaceutical compositions comprising a compound of Formula Ia', Ib', Ic', or II' may be administered one to six days per week or it may be administered in cycles with rest periods in between the cycles (e.g., daily administration for two to eight consecutive weeks, then a rest period with no administration for up to one week between treatments) or it may be administered on alternate days.

For example, the compounds of Formula Ia', Ib', Ic', or II' can be administered in a total daily dose of up to 800 mg. The compounds of Formula Ia', Ib', Ic', or II' can be administered once daily (QD), or divided into multiple daily doses such ax twice daily (BID), and three times daily (TID). The compounds of Formula Ia', Ib', Ic', or II', can be administered at a total daily dosage of up to 800 mg, for example, about 200 mg, 300 mg, 400 mg, 600 mg, or 800 mg, which can be administered in one daily dose or can be divided into multiple dally doses as described above. In specific aspects, the administration is oral or by intravenous delivery.

to one embodiment, the compound is administered once daily at a dose of about 200-600 mg. In another embodiment, the compound is administered twice daily at a dose of about 200-400 mg. In another embodiment, the compound is administered twice daily at a dose of about 200-400 mg intermittently, for example three, four or five days per week. In one embodiment, the daily dose is about 200 mg which can be -administered once-daily, twice-daily, or three-times daily. In one embodiment, the daily dose is about 300 mg which can be administered once-daily, twice-daily, or three-times daily. In one embodiment, the daily dose is about 400 mg which can be administered once-daily, twice-daily, or three-times daily.

Compounds of Formula Ia', Ib', Ic', or II' can be administered in accordance with any dose and dosing schedule that achieves a dose effective to treat cancer. Each compound can be administered in a total daily dose that may vary from patient to patient, and may be administered at varying dosage schedules. For example, a compound of the invention can be administered to the patient at a total daily dosage of between 25-4000 mg/m$^2$. In particular, compounds of Formula Ia', Ib', Ic', or II' can be administered in a total daily dose of up to 800 mg, especially by oral or intravenous administration, once, twice, or three times daily, continuously (every day) or Intermittently (e.g., 3-5 days a week).

In addition, the compounds of Formula Ia', Ib', Ic', or II' may be administered according to any of the schedules described above, consecutively for a few weeks, followed by a rest period.

In one embodiment, the patient can receive intravenously or subcutaneously the compounds of Formula Ia', Ib', Ic', or II' in quantities sufficient to deliver between about 3-1500 mg/m$^2$ per day, for example, about 3, 30, 60, 90, 180, 300, 600, 900, 1200 or 1500 mg/m$^2$ per day. Such, quantities may be administered in a number of suitable ways, e.g. large volumes of low concentrations of the compounds or Formula Ia', Ib', Ic', or II' can be used during one extended period of time or several times a day. The quantities can be administered for one or more consecutive days. Intermittent days, or a combination thereof per week (7 day period). Alternatively, low volumes of high concentrations of the compounds of Formula Ia', Ib', Ic', or II' can be used during a short period of time, e.g. once a day for one or more days either consecutively, intermittently or a combination thereof per week (7 day period). For example, a dose of 300 mg/m$^2$ per day can be administered for 5 consecutive days for a total of about 1500 mg/m$^2$ per treatment. In another dosing regimen, the number of consecutive days Can also be 5, with treatment lasting for 2 or 3 consecutive weeks for a total of about 3000 mg/m$^2$ or about 4500 mg/m$^2$ total treatment.

Typically, an intravenous formulation may be prepared which contains a concentration of compounds of Formula Ia', Ib', Ic', or II' of between about 1.0 mg/mL to about 10 mg/mL, e.g. about 2.0 mg/mL, 3.0 mg/mL, 4.0 mg/mL, 5.0 mg/mL, 6.0 mg/mL, 7.0 mg/mL, 8.0 mg/mL, 9.0 mg/mL and 1.0 mg/mL and administered in amounts to achieve the doses described above, in one examples a sufficient volume of intravenous formulation can be administered to a patient in a day such that the total dose for the day is between about 300 and about 1500 mg/m$^2$.

Subcutaneous formulations can be prepared according to procedures well known, in the art at a pH in the range between about 5 and about 12, which include suitable buffers and are tonicity agents, as described below. They can be formulated to deliver a daily dose of any of compounds of Formula Ia', Ib', Ic', or II' in one or more daily subcutaneous administrations, for example, one, two or three times each day.

It is apparent to a person skilled in the art that any one or more of the specific dosages and dosage schedules of the compounds of Formula Ia', Ib', Ic', or II' are also applicable to any one or more of the anti-cancer agents to be used in a combination treatment. Moreover, the specific dosage and dosage schedule of the compounds of Formula Ia', Ib', Ic', or II' can further vary, and the optimal dose, dosing schedule, and route of administration can be determined based upon the specific drug combination that is being used. Further, the various modes of administration, dosages, and dosing schedules described herein merely set forth specific embodiments and should not be construed as limiting the broad scope of the invention. Any permutations, variations, and combinations of the dosages and dosing schedules are included within the scope of the present invention.

iii. Formulation

An "effective amount" of compounds of Formula Ia', Ib', Ic', or II' is the quantity which, when, administered to a subject having a disease or disorder, results in regression of the disease or disorder in the subject. Thus, an effective amount of a compound of the disclosed invention is the quantity which, when administered to a subject having a cell proliferation disorder, results in, for example, regression of cell growth or cell death in a subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used, herein, the term "effective amount" refers to an amount of a compound, or a combination of compounds, of the present invention effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as for example, anti-cancer activity or anti-cancer activity or anti-neoplastic activity. The combination of compounds optionally is a synergistic combination. Synergy, as described, for example, by Chou and Talalay (1984) Adv. Enzyme Regul. 22; 27-55, occurs when the effect of the compounds when administered In combination is greater than the additive effect of the compounds when, administered alone as a single agent. In general, a synergistic effect is most clearly demonstrated at suboptimal concentrations of the compounds. Synergy cars be in terms of lower cytotoxicity, or increased anti-proliferative effect, or some other beneficial effect of the combination compared with the individual components.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the present invention can be used to coat or impregnate a medical device, e.g., a stent.

The term "prophylactically effective amount" means an effective amount of a compound or compounds, of the present invention that is administered to prevent or reduce the risk of unwanted cellular proliferation.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

A "pharmaceutical composition" is a formulation containing the compounds of Formula Ia', Ib', Ic', or II' in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, metal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration, of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

As used, herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of Formula Ia', Ib', Ic', or II' are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such, as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic,
mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, eyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2,2,2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined, herein, of the same salt.

The pharmaceutically acceptable salts of the compounds of Formula Ia', Ib', Ic', or II' can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxyl amine-containing and imine-containing, compounds of the present invention.

The compounds of Formula Ia', Ib', Ic', or II' can also be prepared as esters, for example pharmaceutically acceptable esters. For example a carboxylic acid functional group in a compound can be converted to its corresponding ester, e.g., a methyl, ethyl, or other ester. Also, an alcohol group in a compound can be converted to its corresponding ester, e.g., an acetate, propionate, or other ester.

The compounds of Formula Ia', Ib', Ic', or II' can also be prepared as prodrugs, for example pharmaceutically acceptable prodrugs. The terms "pro-drug" and "prodrug" are used interchangeably herein and refer to any compound that releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when, such prodrug is administered to a subject. Prodrugs of the present invention are prepared by modifying functional groups present in the compound in such a way that the modifications are cleaved, either in routine manipulation or in vivo to the parent compound. Prodrugs include compounds of the present invention wherein a hydroxyl, amino, sulfhydryl, carboxyl, or earbonyl group is bonded to any group that may be cleaved in vivo to form a tree hydroxyl, free amino, free sulfhydryl free carboxyl or free carbonyl group, respectively.

Examples of prodrugs include, but are not limited, to, esters (e.g., acetate, dialkylaminoacetates, formates, phosphates, sulfates, and benzoate derivatives) and carbamates (e.g., N,N-dimethylaminocarbonyl) of hydroxyl functional groups, ester groups (e.g. ethyl, esters, morpholinoethanol esters) of carboxyl functional groups, N-acyl derivatives (e.g. N-acetyl), N-Mannich bases, Schiff bases and enaminones of amino functional groups, oximes, acetals, ketals and enol esters of ketone and aldehyde functional groups in compounds of the invention including compounds A, or B or derivatives, and the like, (see, Bundegaard, H. "Design of Prodrugs" p1-92, Elesevier, New York-Oxford (1985)).

All percentages and ratios used herein, unless otherwise indicated, are by weight.

"Combination therapy" (or "co-therapy") includes the administration of compounds of Formula Ia', Ib', Ic', or II' and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described in having, including, or comprising specific components, it is contemplated that compositions also consist essentially of, or consist of the recited components. Similarly, where processes are described as having, including, or comprising specific process steps, the processes also consist essentially of or consist of the recited processing steps. Further, it should be understood that the order of steps or order for performing certain actions are immaterial so long as the invention remains operable. Moreover, two or more steps or actions may be conducted simultaneously.

The compounds of Formula Ia', Ib', Ic', or II', or pharmaceutically acceptable salts thereof, can be administered orally, nasally, transdermally, pulmonary, inhalationally, buccally, sublingually, intraperintoneally, subcutaneously, intramuscularly, intravenously, rectally, intrapleurally, intrathecally and parenterally. In certain embodiments, the compound is administered orally. One skilled in the art will recognize the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition. Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, compounds of Formula Ia', Ib', Ic', or II' are prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as fatty oil.

In some embodiments, various other materials are present as coatings or to modify the physical form of the dosage unit. For instance, in some embodiments, tablets are coated with shellac, sugar or both. In some embodiments, a syrup or elixir contains in addition to the active ingredient, sucrose as a sweetening agent, methyl and propylparabens; as preservatives, a dye and a flavoring such as cherry or orange flavor, and the like.

For some embodiments relating to parental administration, the compounds of Formula Ia', Ib', Ic', or II' or salts, solvates, tautomers or polymorphs thereof, can be combined with sterile aqueous or organic media to form injectable solutions or suspensions. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

In some embodiments, the compounds of Formula Ia', Ib', Ic', or II' are formulated to deliver the active agent by pulmonary administration, e.g., administration of an aerosol formulation containing the active agent irony for example, a manual pump spray, nebulizer or pressurised metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the basal passages. In some embodiments whom the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, for example, typically less than about five minutes, preferably less than about ninety seconds, more preferably in less than about thirty seconds and most preferably in less than about ten or fifteen seconds. Such formulations are suitable for administration to a subject via a variety of routes, for example by insertion into a body cavity or application to a moist body surface or open wound.

Typically, a "flash, dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see tor example, effervescent dosage forms and quick release coatings of insoluble microparticles in U.S. Pat. Nos. 5,378,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, tree-form fabrication in. U.S. Pat. No. 6,471,992; saccharidehaxed carrier matrix and a liquid binder in U.S. Pat. Nos. 5,587,172, 5,616,344, 6,277,406, and 5,622,719; and other forms known to the art.

The compounds of Formula Ia', Ib', Ic', or II' can also be also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition, over a prolonged period.

Also contemplated are formulations, for example, liquid formulations, including cyclic or acyclic encapsulating or solvating agents, for example, cyclodextrins, polyethers, or polysaccharides (e.g., methylcellulose), or polyanionic-cyclodextrin derivatives with a sodium sulfonate salt group separate from the lipophilic cavity by an alkyl ether spacer group or polysaccharides. In one embodiment, the agent can be polyanionic β-cyclodextrin derivative with a sodium sulfonate salt separated from the lipophilic cavity by a butyl ether spacer group, e.g., CAPTISOL® (CyDex, Overland, and KS). One skilled in the art can evaluate suitable agent/ disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Example 1

Synthesis of Compound 11-19.

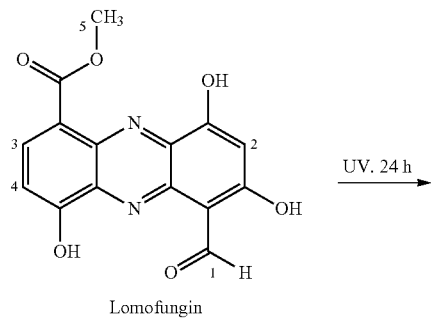

Lomofungin

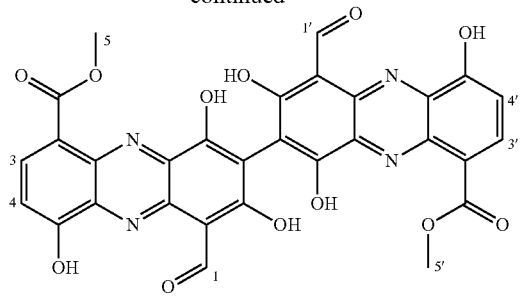

II-19

The starting compound (lomofungin) was dissolved in DMSO and irradiated with UV light for 24 hours. Dimerization was monitored by LC-MS on a C18 column eluted with a methanol gradient (0-90% methanol with 0.1% trifluoroacetic acid).

The starting material (lomofungin) was characterised by NMR and LC/MS. NMR (DMSO-$d_6$) gave peaks at 3.99 ppm (3H), 6.84 ppm (1H), 7.27 (1H); 8.17 (1H), 10.93 (1H), and 11.10 (1H). LC-MS peak exhibited peaks at 315 (MH$^+$) and 316 (MH$_2^+$).

Analysis of Compound II-19 Compound II-19 was characterized by NMR and LC/MS. NMR (DMSO-$d_6$) gave peaks at 3.99 ppm (3H), 7.34 (1H); 8.21 (1H), 11.07 (1H), and 11.21 (1H). LC-MS peak exhibited peaks at 627 (MH$^+$) and 628 (MH$^{2+}$).

Example 2

Preferential Inhibition of Mcl-1 by Compound A.

The expression level of Mcl-1 correlates directly to chemosensitivity and Survival of certain non-Hodgkin's lymphomas (Petlickovski et al. (2005) Blood 105(12): 4820-7) as well as prostate cancer (Royuela et al. (2001) Eur. Cytokine Netw. 12(4): 654-63), liver cancer (Fleischer et al. (2006) Int. J. Oncol. 28(1): 25-32) and other cancers. Mcl-1 is therefore an ideal target for treating these cancers. This example shows that the BH3 mimic compound A Inhibits the binding of the BH3 domain of the Bcl-2 family protein Bim Mcl-1 and, to a lesser extent, Bcl-xL. Accordingly, this example indicates that compound A may be particularly effective in treating certain hematological malignancies that are affected principally by the Bcl-2 family protein Mcl-1.

Materials and Methods

In this example, a Fluorescence Polarization (FP) assay was used to demonstrate the activity of the BH3 mimic compounds A In inhibiting Mcl-1 as well as Bcl-xL binding to Bim BH3 as described in Degterev et al. (2001) Nature Cell Biology 3: 173-182.

A nineteen amino acid peptide, corresponding to the BH3 domain of Bim, with the sequence FITC-GGGIAQELRRIG-DEFNAY (SEQ ID NO: 1) was labeled with the tluorophore FITC according to the manufacturer's instructions (Molecular Probes, Eugene, Oreg.). This sequence was identified as being able to bind to purified Bcl-xL protein (Sattler et al. (1997) Science 275(5302): 983-86) and to have biological activity in cells (Holinger et al. J. Biol. Chem. 274; 13298-1330).

In addition, recombinant GST-Mcl-1 and GST-Bcl-xL fusion proteins were generated in *E.coli* and purified using glutathione-sepharose beads using conventional techniques known to those skilled in the fields of biochemistry and molecular biology, (methods for preparation are described in Strategies for Protein Purification and Characterization, Marshak, D, Kadonga, J, Burgess R, Knuth, M, Brennan, W, Sue-Hwa, L, CSH press, Cold Spring Harbor, N.Y.). Binding of the recombinant proteins to the fluorescent Bim BH3 domain was confirmed by titration of increasing concentrations of the recombinant proteins against a constant amount of labeled Bim peptide (16.65 nM). Quantitation of binding was accomplished by FP assay with mP measurements made on the Analyst-GT reader (Molecular Devices, Sunnyvale, Calif.).

Further, the ability of compound A to disrupt the interaction between the fluorescent Bim BH3 peptide and the two fusion proteins was assessed using a fluorescence polarization assay. The Bim peptide (in solution at 4 nano-Molar) and either GST-Mcl-1 (in solution at 12.5 nM) or GST-Bcl-xL (in solution at 11.8 nM) were first combined together in phosphate buttered saline buffer, and then the compound solution in DMSO was added to final concentrations ranging from 10 µM to 0.1 nM). Normally the unbound Bim polypeptide results in polarization of 5 mP units. Upon binding of the GST-Bcl-xL and GST-Mcl-1 fusion protein, polarization increased to 100 mP units.

Results

Data from Fluorescence polarization studies comparing binding of the Bim-BH3-FITC peptide to soluble Mcl-1-1-GST and Bcl-xL-GST proteins exposed to compound A in concentrations ranging from 10 µM to 1 nM is shown in FIG. 1. Y axis represents % shift in polarization (mp units). Compound A was effective at inhibiting the Bim-BH3 peptide from the Bcl-xL with a drug concentration that provokes a response halfway between baseline and maximum ($IC_{50}$) of 480 nM for Mcl-1. Also, the compound was able to inhibit the binding of the Bim BH3 peptide from the Bcl-xL protein with an $IC_{50}$ of >16,000 nM (FIG. 1). As seen in FIG. 1, Bim BH3/Mcl-1 inhibition was significantly more pronounced than Bim/Bcl-xL. This indicates a highly preferential activity of the compound A which has important implications for the therapeutic value of this compound.

Example 3

Inhibition of Mcl-1 by Compound and II-19

The compound II-19 is assessed for ability to inhibit binding of the BH3 peptide of Bim to Mcl-1 and Bcl-xL. The activity for blocking Bim BH3 binding to both Bcl-xL and Mcl-1 fusion proteins are compared as in Example 2.

Material and Methods

Experiments are performed using the fluorescence polarization assay as described in Example 2. Either Bcl-xL or Mcl-1 fusion proteins were titrated and maximum mp shift indicate binding concentrations for drug titration studies, as described in Example 2. Compound II-19, was titrated from 10 µM to 0.1 nM in 2 fold serial dilution into the peptide/protein solution. The $IC_{50}$ for blocking each BH3 peptide from Mcl-1 are assessed using FP, as described in Example 2.

Results

Figure 2:
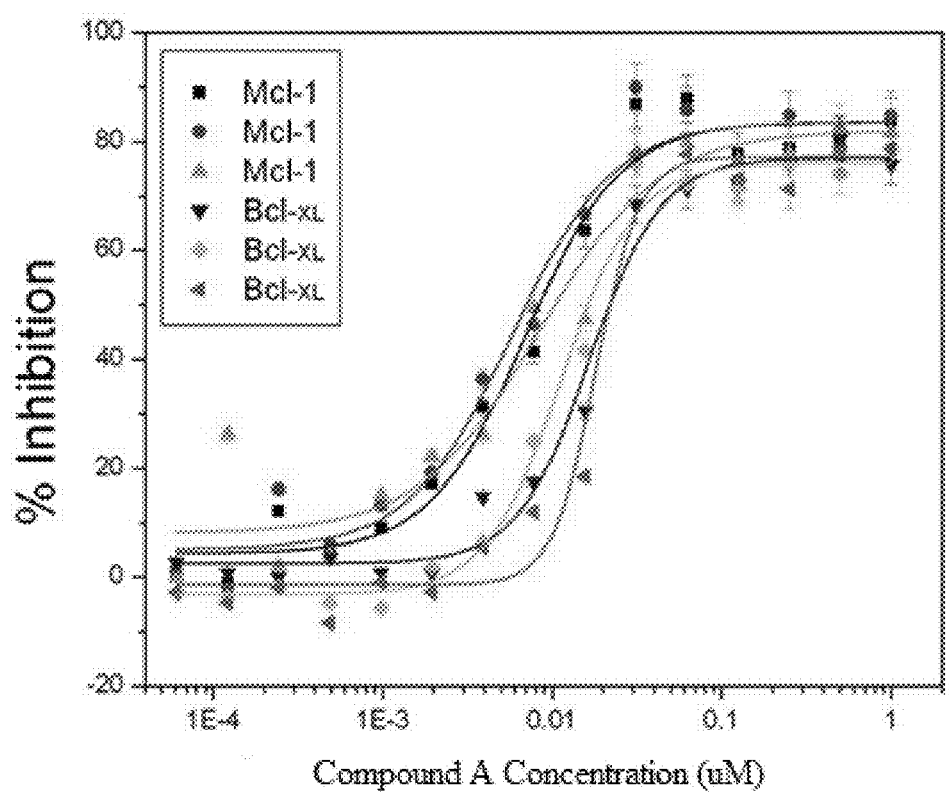
FIG. 2 is a graph showing preferential competition of Bim-BH3 peptide binding to Mcl-1 vs. Bim-BH3 peptide binding to Bcl-xL by the BH3 mimic compound II-19. Fluorescence Polarization (FP) was used to measure binding as described in Example 2.

Data from Fluorescence polarization studies comparing binding of the Bim-BH3-FITC peptide to soluble Mcl-1-1-GSTand Bcl-xL-GST proteins exposed to compound II-19 in concentrations ranging from 10 µM to 1 nM is shown in FIG. 2. Y axis represents % shift in polarization (mp units). Compound II-19 with a drug concentration that provokes a response halfway between baseline and maximum ($IC_{50}$) of 7 nM for Mcl-1 and 15 nM for Bcl-xL (FIG. 2). Also compound II-19 has a 2-fold preference for inhibition of Mcl-1 vs. Bcl-xL as seen in FIG. 2. The compound II-19 is more active against Mcl-1 than any other reported compound. This improved binding is an advantage for treating cancers therapeutically.

Example 4

Activity of Compounds A, II-19, and Obatoclax in Killing Human Tumor Cell Lines

This example anticipates the activity of the compounds A, and II-19, and derivatives, in killing certain human tumor-derived cell lines grown in culture. Leukemia and myeloid cells were used to assess cell tumor killing activity of the compounds A, and II-19, and certain derivatives.

Materials and Methods

Cell Culture

The lymphoid derived cell lines DHL-6 and DHL-10 were obtained from Anthony Letai of the Dana Father Cancer Research Institute, Boston, Mass. The myeloid derived cell line NCP-H929 was obtained irons, the NIH/NCI cell repository. AML-3 cells were obtained from Dr. Michael Andreef (MD Anderson Cancer Center, Houston, Tex.). Cells were grown in RPMI 1640 medium (GIBCO-BRL) supplemented with Pen-strep-glutamine (Gibco 10378) and 5% fetal bovine serum.

$EC_{50}$Assays

Cells were expanded in tissue culture in appropriate media and then subcultured into 96-well plates at a seeding density of 20,000-40,000 cells per well, and cells were treated with one or more compounds that were titrated info appropriate medium with FCS. Cell lines were treated with compound A at concentrations ranging from 25 µM to 25 nM. The BH3-mimetic obatoclax (Nguyen M et al. (2007), Proc. Natl. Acad. Sci. USA 104:19512-19517) was also tested against the SUDHL-6, SUDHL-10, and NCI-H929 cell lines. Cells were treated for 48 hours and scored for viability using the MTS assay (Promega). Growth inhibition was indicated as a percentage of control cell growth. Growth was determined by measuring the $A_{570}$ (control cells)—$A_{570}$ (treated cells)/$A_{570}$ (control cells). $EC_{50}$ values were calculated using Graphpad Prizm software.

Results

Figure 3:
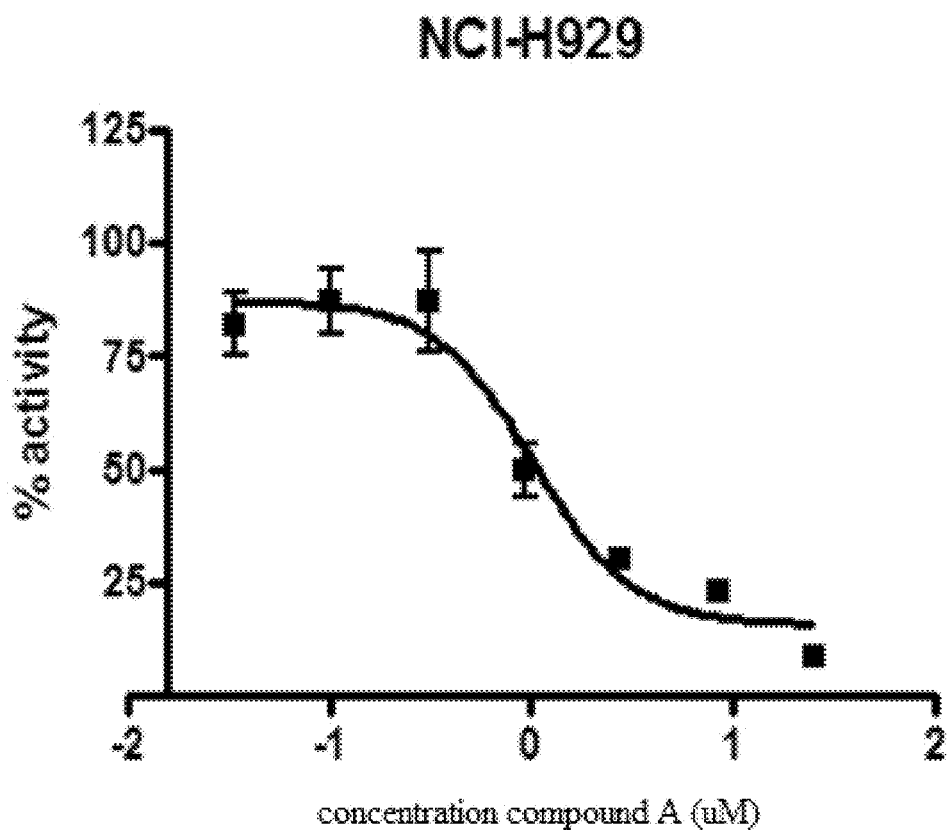
FIG. 3 is a graph showing the efficacy of compound A, in killing multiple myeloma-derived cells.
Figures 4, 4A:
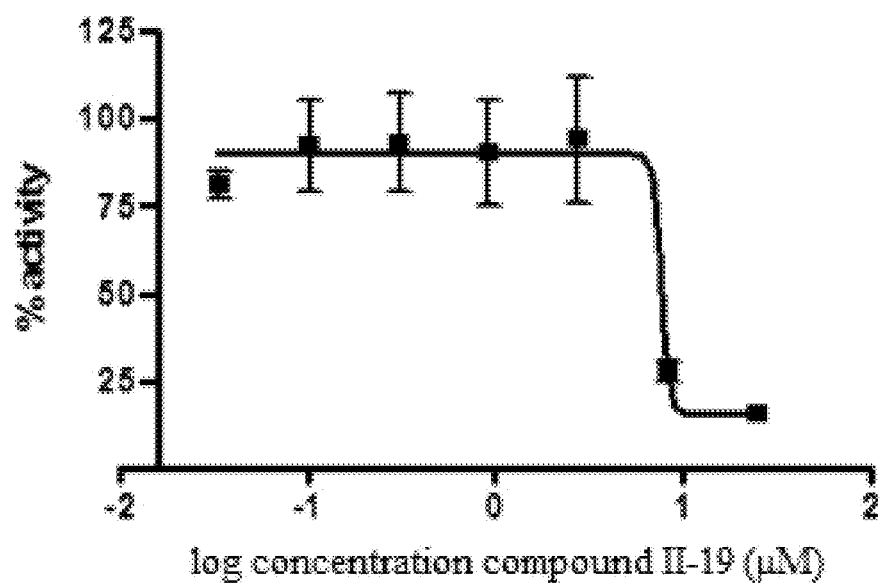
FIG. 4 is a set of graphs showing the efficacy of compound II-19, in killing multiple myeloma derived cells (NCI-H929, FIG. 4a), acute myelogenousleukemia cells (AML-3, FIG. 4b) and lymphoid derived cells (SUDHL-6, FIG. 4c). On-target activity is indicated by the absence of activity against the Bax/Bak deficient cell line SUDHL-10 (FIG. 4d).
Figure 4B:
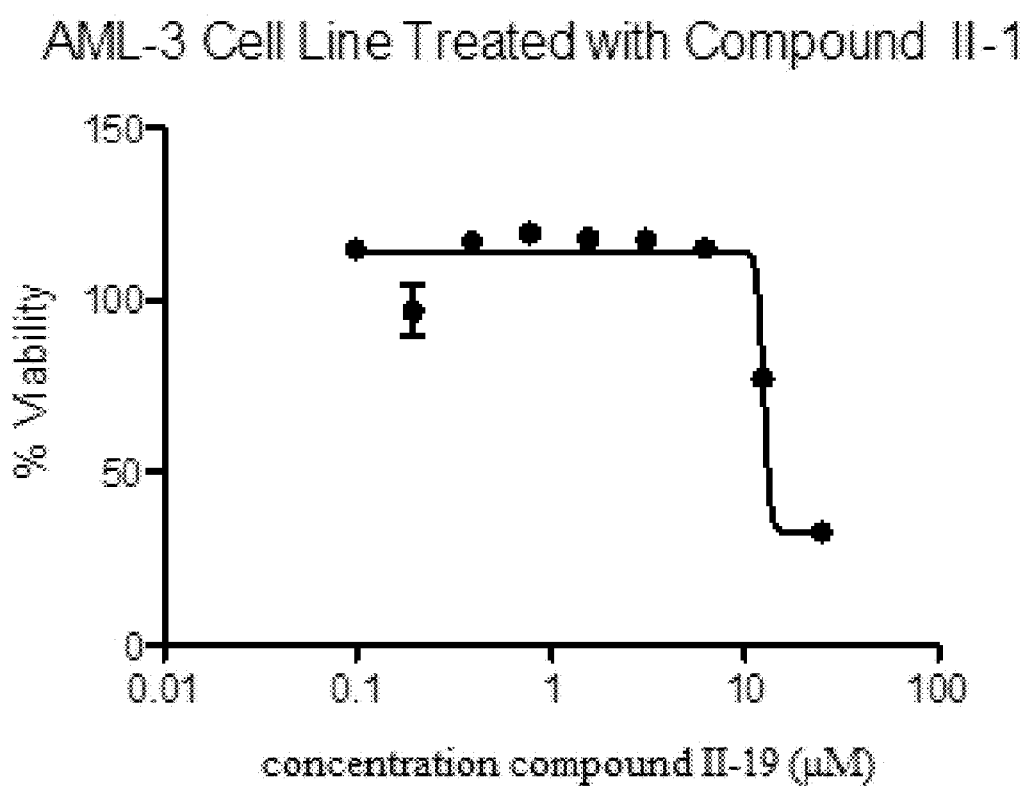
FIG. 4e is a graph showing the efficacy of obatoclax in killing multiple myeloma derivated cells (NCI-H929) and a Bax-Bak deficient lymphoid derived cell, line (SUDHL-10).
Figure 4C:
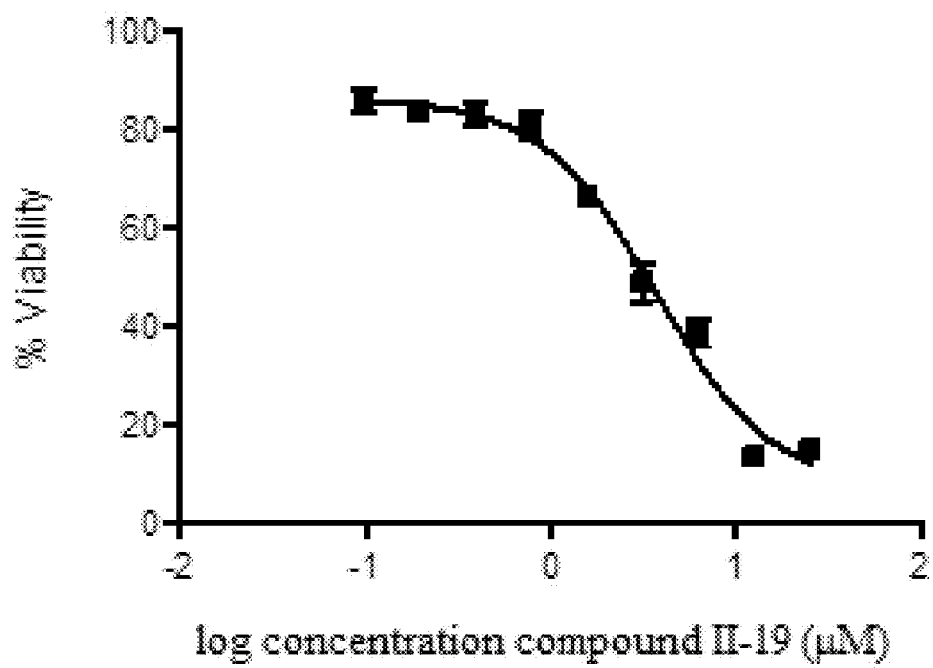
Figure 4D:
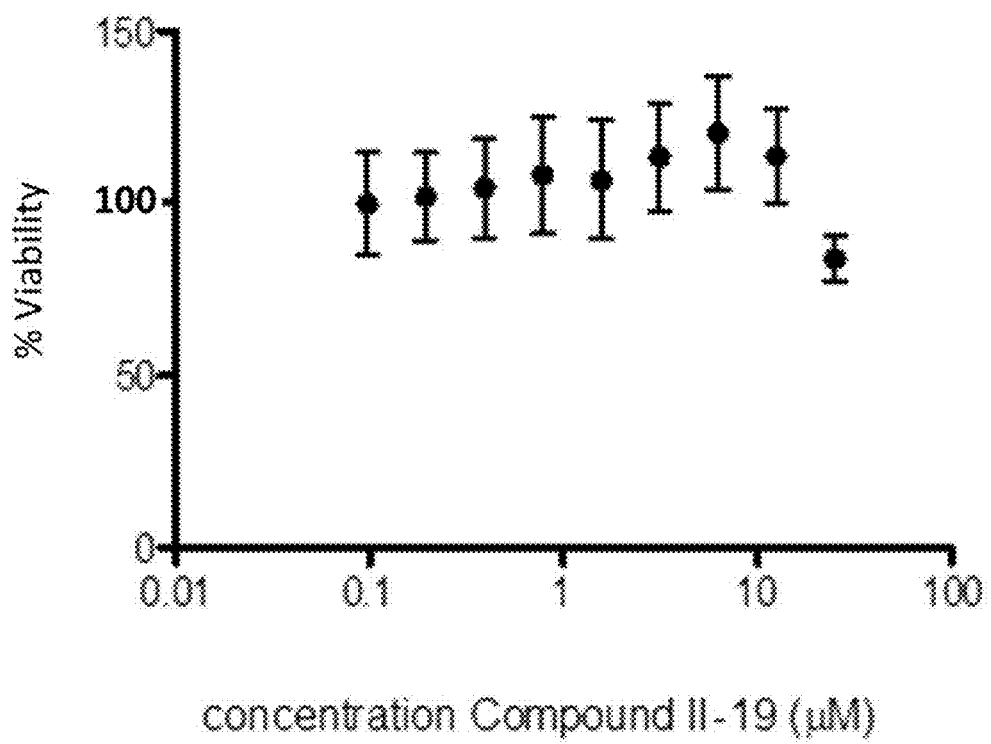
Figure 4E:
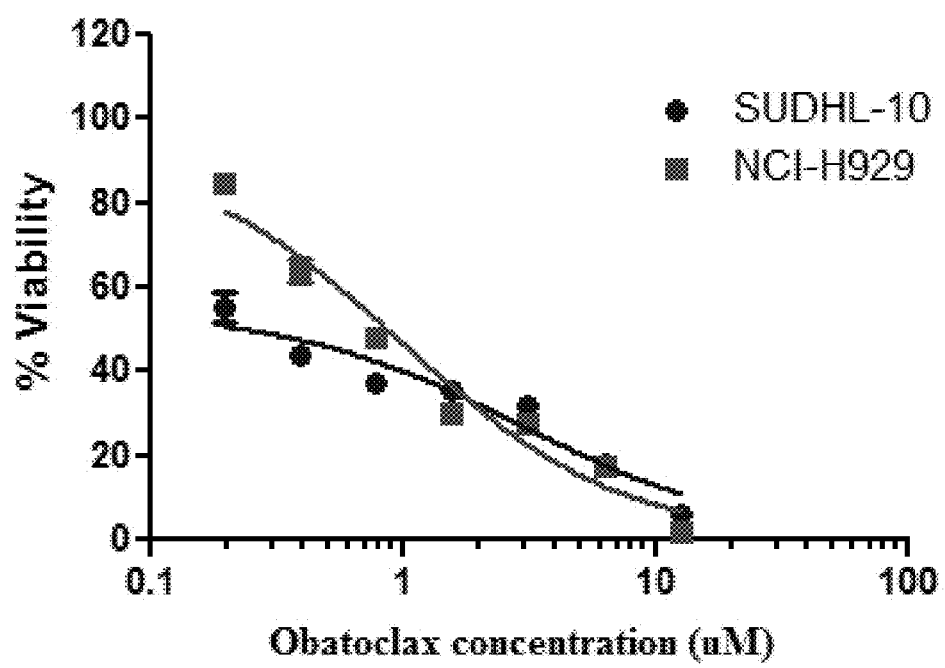

Cell killing by compound A is shown in FIG. 3. After 48 hours cells were assessed for viability using the MTS assay as described above. Y axis represents survival as % untreated control. The X-axis represents the concentration of the compound in log scale. Data represents mean of 3 separate wells for each condition. In the multiple myeloma cell line NCI-H929 the $EC_{50}$ for compound A was 1 µM for compound A (FIG. 3) and 8 µM for compound II-19 (FIG. 4a). Compound II-19 also showed activity against the lymphoid cell line SUDHL-6 ($EC_{50}$=3 µM, FIG. 4c) and the acute myelogenous leukemia cell line AML-3 ($EC_{50}$=10 µM, FIG. 4b). No activity was observed in the cell line SUDHL-10 ($EC_{50}$=>20 µM, FIG. 4d). This cell line is devoid of Bax and Bak activity, and is therefore not responsive to Bcl-2 family inhibition. The lack of observable activity in this assay for compound II-19 is consistent with Mcl-1 specific inhibition and suggests that this compound is not acting off-target (e.g. killing via necrotic pathways or inhibiting cell proliferation). The BH3-mimetic obatoclax (Nguyen M et al. (2007), Proc. Natl. Acad. Sci. USA 104:19512-19517) was also tested against the SUDHL-6, SUDHL-10, and NCI-H929 cell lines and showed $EC_{50}$ values of 2.5 nM, 0.8 uM, and 1.8 uM, respectively (see FIG. 4e for data in SUDHL-10 and NCI-H929 cell, lines). The activity in the BAX/BAK deficient cell line SUDHL-10 indicates the compound kills cells at least in part by off-target activity not involving the BCL2 pathway—similar studies have been previously reported (Vogler, M. et al. (2009), Cell Death and Differentiation 16:1030-1039). This is in contrast to the cell killing profile of compound II-19 which is disclosed herein.

These data indicate that both compounds are effective at killing tumor cells in culture and are anti-lymphoid and anti-myeloid tumor compounds.

CONCLUSIONS

Lymphoid and myeloid cells that have elevated expression of Mcl-1 tend to be resistant to certain chemotherapies. This includes multiple myeloma (MM) (Zhang B et al. (2002), Blood 99: 1885-1893), non-Hodgkin's lymphomas (Cho-Vega J H et al. (2004) Hum. Pathol. 35(9): 1095-100) and chronic lymphocytic leukemia (CLL) (Michels J, et al. (2004), Oncogene 23:4818-4827) cells. As shown in Example 2 above, compound A and compound II-19 target Mcl-1. This example sets out to show that elevated Mcl-1 would cause hypersensitivity to compound A and II-19 under certain conditions. It is more likely that hypersensitivity will occur when the BH3-only protein, Bim, Puma or Noxa are also elevated. Both of these proteins have BH3-mediated binding to Mcl-1. Therefore these cells will be more sensitive to whichever of the BH3 mimic compound A or II-19 that have activity in disrupting Bim, Puma or Noxa BH3 mediated binding to Mcl-1.

Compounds described herein, are effective in killing tumor cells that have elevated Mcl-1, and those that have elevated Mcl-1 and elevated BH3-only protein Noxa and/or Puma. The BH3 mimic compounds described herein are effective at treating chemo-resistant MM, CLL, NBL, AML, and ALL cells that display elevated Mcl-1. Compounds described herein are also effective as second line therapy in patients treated with proteosome inhibitors such as Bortexomib (Velcade®) who display elevated Mcl-1 with or without elevated Bim, Puma, or elevated Noxa.

Example 5

In situ Mitochondrial Assay for Compound A

The on-target activity of compound A was validated. Changes in mitochondrial membrane potential were observed utilizing the potentiometric dye JC-1 (Invitrogen, Carlsbad, Calif.) a mitochondrial dye that loses its 590 emission signal when the outer membrane of the mitochondria losses its membrane potential. (Deng et al. (2007) Cancer Cell. 12(2): 171-85).

Figure 5:
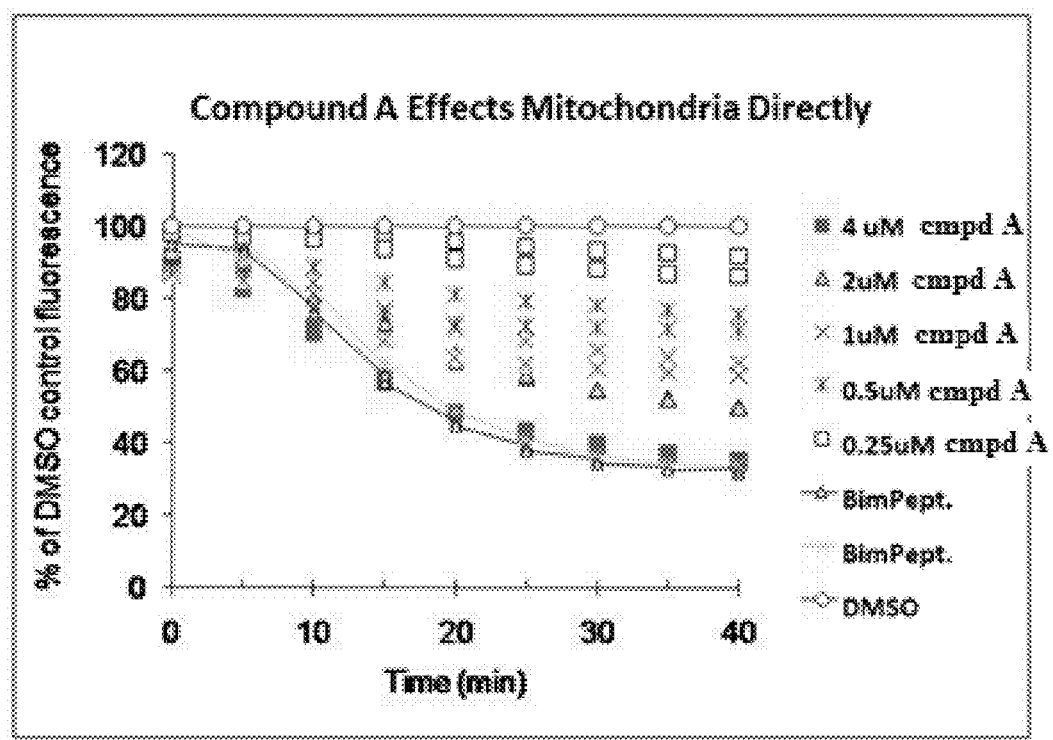
FIG. 5 is a chart showing the ability of compound A to induce mitochondrial membrane permeabilization.
Figure 6:
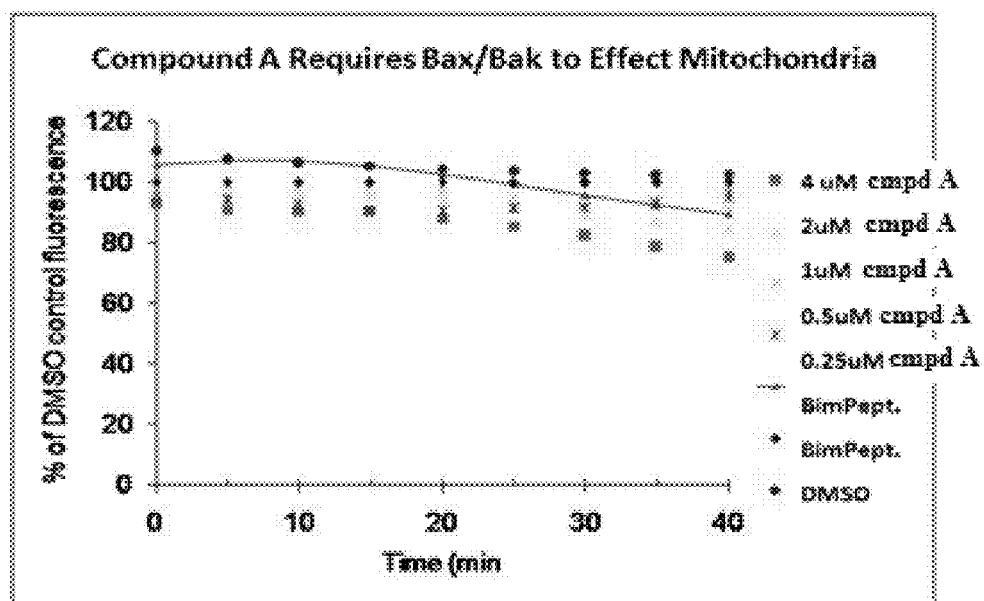
FIG. 6 is a chart demonstrating the selective activity of compound A in inducing mitochondrial membrane permeabilization in a manner that is dependent on Bax and Bak.

The selective response of mitochondria in semi-permeabilized cell lines to the compounds was observed. The assay was performed as described in (Deng et al. (2007) Cancer Cell. 12(2):171-85).
Materials and Methods Suspension cells were grown in RPMI and re-suspended to a 4X assay concentration of $2 \times 10^4$/ml in assay buffer. Assay buffer; 300 mM Trehalose, 10 mM HEPES-KOH pH 7.7, 80 mM KCl, 1 mM EGTA, 1 mM EDTA, 0.1% BSA, 5 mM Succinate. Cells are mixed with JC1 and allowed to label for 10 minutes at 37° C. and then test compounds or control peptides are added in a final reaction. Final assay conditions are $2.5 \times 10^4$ to $1 \times 10^5$ cells/well, 0.005% digitonin, 5 mM BME, 40 µM control peptide (in control wells) or 4 to 0.25 µM test compound (in test wells), 30 µL total volume per well in Greiner 384 flat bottomed well white plates. Plates are read in Biotek, Fluorescence plate reader; 530 nm excitation; 590 nm emission. Loss of JC-1 signal emission wave length (590 nm) is represented as a percent of the non-treated (DMSO control).
Results Response of mitochondria in semi-permeablized lymphoid cell line SUDHL-6 to compound A is shown in FIG. 5. This cell line has functioning Bax and Bax pro-apoptotic protein and is expected to respond to BH3 mediated activation. Loss of JC-1 signal emission wave length (590 nm) is represented as a percent of the non-treated (DMSO control). Lack of response to compound A in mitochondria from Bax/Bak deficient cell line SUDHL-10 is shown in FIG. 6. This cell line does not have functioning Bax and Bax pro-apoptotic protein and is not expected to respond to BH3 mediated activation. These data indicate direct activity of the compound A (ranging from 4 µM to 0.25 µM) on Mcl-1 primed mitochondria (FIG. 5), and that the Bax/Bak activity is required for activity (FIG. 6). This is consistent with the compounds acting through the mitochondrial apoptosis pathway.

Example 6

In Situ Mitochondrial Assay for Compound II-19

The on-target activity of compound II-19 was validated. Changes in mitochondrial integrity were observed utilizing anti-cytochrome c conjugated to Alcxa488 (BD). When the mitochondria are intact, they retain cytochrome c and have bright, punctate staining with the antibody whereas cells with compromised mitochondrial integrity will lose cytochrome c and will not stain with the antibody. This can be observed by microscopy as well as measured by a shift in fluorescence on the FL1 channel of a flow cytometer.

Figure 7:
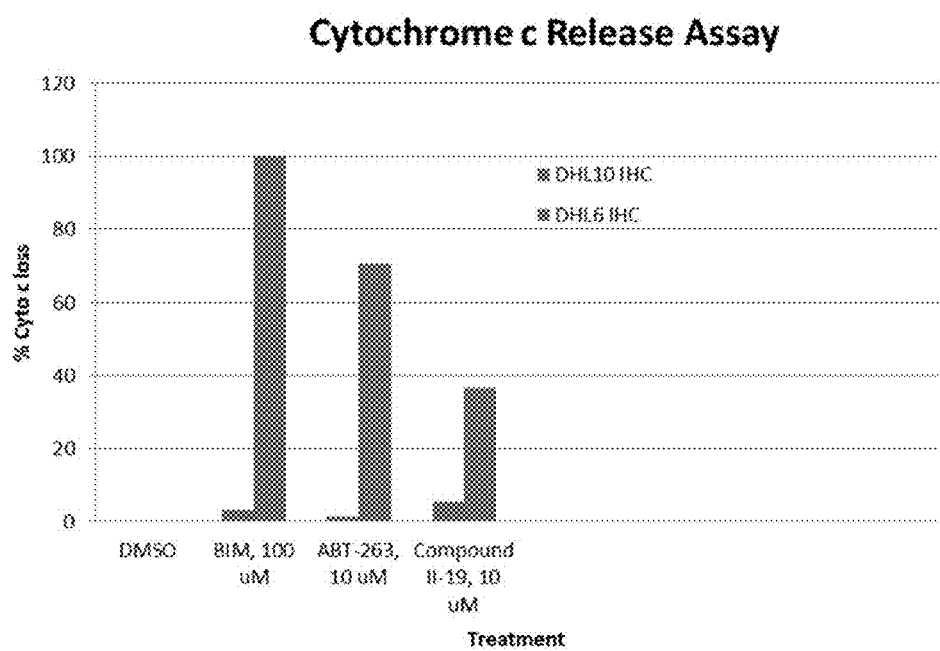
FIG. 7 is a chart showing the ability of compound II-19 to Induce mitochondrial membrane permeabilization in an assay measuring the release of cytochrome C. Response of mitochondria in semi-permeablized lymphoid cell lines SUDHL-6 (right bars in each condition) and SUDHL-10 (left bars in each condition) to compound II-19 demonstrating that compound II-19 causes release of cytochrome c in SUDHL-6 BAX/BAK-functional ceil line but not BAX/BAK-deficient SUDHL-10 cell line.

The selective response of mitochondria in semi-permeabilized cell lines to the compounds was observed. The assay was adapted from (Campos et al. (2006) Cytometry Part A. 69(A):515-523).
Materials and Methods Suspension cell lines SUDHL10 and SUDHL6 were grown in RPMI, washed once in 1xPBS and re-suspended at a concentration of 2e6/ml in assay buffer with 0.0025% Digitonin. Assay buffer; 300 mM Trehalose, 10 mM HEPES-KOH pH 7.7, 80 mM KCl, 1 mM EGTA, 1 mM EDTA, 0.1% BSA, 5 mM Succinate. Cells are incubated with test and control compounds at $10^6$ cells/treatment for 1 hour at room temperature. Samples are fixed with 4% formaldehyde In PBS for 20 minutes, washed once in PBS, and blocked with 2% FBS/0.5%TritonX-100 in PBS. Samples are re-suspended in blocking buffer with 1:250 anti-cytochrome c conjugated to Alexa488 (BD Cat#56028) for 1 hour at 4° C., washed once with blocking buffer and re-suspended in 200 ul PBS. Cytochrome c loss was measured by microscopy. At least 100 cells per treatment were counted and scored as positive for cytochrome c loss if they lacked staining. In both methods DMSO was calculated as 0% cytochrome c loss and the Bim response for DHL6 was used to determine 100% cytochrome c loss.
Results These data indicate direct activity of the compound II-19 at 10 uM on primed mitochondria, and that the Bax/Bak activity is required for activity (compare activity in Bax/Bak-functional cell line (DHL-6) to lack of activity in Bax/Bak-deficient cell line (DHL-10) (FIG. 7). This is consistent with the activity profile of these compounds in cell studies, and indicates that the compounds exert their biological effect through the mitochondrial apoptosis pathway.

Example 7

This example demonstrates the efficacy of compounds described herein in potentiating the tumor cell killing activity of Bortezomib (Veleade®).

Proteosome inhibitors such as Bortezomib induce apoptosis and have been recognized as a class of anti-tumor therapeutics (Adams (2004) Cancer Cell 5: 417-421). Bortezomib (Velcade®) has been approved to treat A-myeloid leukemias and is in phase 3 trials for treatment of solid tumors. Bortezomib is known to dysregulate proteosome-mediated maintenance of Mcl-1 levels in the cell. Accumulated Mcl-1 in Bortezomib-treated cells has been shown to reduce cell killing and promote tumorigenesis, while reduction of Mcl-1 in cells enhances the effectiveness of Bortezomib in inducing apoptosis (Nencioni et al. (2005) Blood 105: 3255-62). Further, Bortezomib has been shown to cause elevated expression of the BH3-only protein Noxa (Qin et al. (2005) Cancer Res. 65(14): 6282-93). The combination of elevated expression of Mcl-1 and Noxa is likely to lead to a cell state previously described as BH3 "sensitization" (Letai et al. (2002) Cancer Cell. 2(3); 183-92,) and make these cells particularly responsive to Mcl-1 specific inhibition.

Materials and Methods

The experiments are performed in Jurkat cells or in primary A-myeloid leukemia cells. Cells are treated with Bortezomib alone or in combination with compound A, or II-19, or derivatives and $GI_{50}$ values are determined using the MTS assay as described in Example 4.

Jurkat cells are obtained from the American Type Culture Collection (ATCC) Manassas, Va. Primary AML cells arc described (Milella et al. (2002) Blood 99(9): 3461-64) and can be obtained from Dr. Michael Andreeff, M.D. Anderson Cancer Center, Houston, Tex. Mcl-1 rabbit polyclonal anti-Human Mcl-1 IgG is available from Cell Signaling Technologies (Beverly Mass.), RPMI 1640 medium is available from GIBCO-BRL (Carlsbad, Calif.).

MTS cell viability reagents are available from Promega, (Madison, Wis.). Bortezomib (Velcade®, Millennium Pharmaceutical, Cambridge, Mass.) is available with prescription from any pharmacy.

Cells are to be planted in 90-well plates at $2\times10^4$ cells/well and incubated in 200 µl RPMI with 10% fetal calf serum with antibiotics for 48 hours. Bortezomib is titrated in a 2 fold serial dilution that ranges from 5 to 320 ng/ml (5, 10, 20, 40, 80, 160, 320 ng/ml). Treated cells are allowed to incubate for 48 hours. Treated cells are then assessed for viability using the MTS assay as described in Example 4. The $GI_{50}$ is determined.

Combination treatment of Bortezomib and compounds of Formula Ia', Ib', Ic', or II' is performed after the $GI_{50}$ of Bortezomib is established. Cells are treated with three concentrations of Bortezomib, the $GI_{50}$ and 2.5 and 5 fold lower concentrations. To these treated cells, the compounds of Formula Ia', Ib', Ic', or II' is added simultaneously in concentrations of 10, 5, 2.5, 1.25, 0.67, 0.34, 0.17, 0.08, 0.04 and 0.02 µM. Combination treated cells and cells treated with either Bortezomib alone or the BH3 mimic compounds of Formula Ia', Ib', Ic', or II', alone are assessed for viability following 24, 48, and 72 hours using the MTS assay protocol described in Example 4.

Further analysis of cell death is conducted using fluorescence-activated cell sorting (PACS) analysis ofannexin V positive staining with the vital dye propidlum iodide by standard methods and as described in Wilkins et al. (20(12) Cytometry 48(1): 14-9. Determination of enhanced killing with Bortezomib is correlated with expression levels of Mcl-1 as determined by western blotting of Bortezomib treated and non-treated cells, as well as combinations of treated cell lysates with anti-Mcl-1 antibodies (Cell Signaling Technologies, Beverly, Mass.).

Results

Treatment of cells with the Bortezomib (Velcade®) has been shown to cause elevated Mcl-1 as well as elevated Noxa in lymphoid cells (Perex-Galan et al. (Sep. 15, 2005) Blood 107:257-264: Qln et al. (2005) Cancer Res. 15: 65(14): 6282-93). This combination of elevated Mcl-1 with elevated Noxa leads to the condition described by Letai as "primed" to respond to an Mcl-1 inhibitor.

The compound or compounds among the compounds of Formula Ia', Ib', Ic', or II', that best inhibit Mcl-1 will be most effective in synergizing with Bortezomib and increasing its effective range.

Because the chemo therapeutic compounds taxol and doxorubicin mediate cell death through the activation of the tumor suppressor p53, and because Noxa is downstream of p53, it is anticipated that these treatments will also cause Mcl-1 over-expressing cells to become "primed" for Noxa mediated death when the Mcl-1/Noxa complex is disrupted, as would be the ease in treating with a Mcl-1 specific BH3 mimic compound. Therefore it is anticipated that the compound(s) of Formula Ia, Ib, Ic, or II that best inhibit Mcl-1 will be most effective in synergizing with taxol or doxorubicin and increasing the effective range of these compounds in killing tumor cells in vitro. It is anticipated that this efficacy will transfer to killing of tumor cell in vivo in animal models for hematological malignancies and to therapeutic value in treating hematological malignancies in humans.

Example 8

In vivo Activity of Compound A in a Mouse/Human Xenograft Model for Lymphoma

Compound A was tested in SCID mice at SRI International, Menlo Park, Calif. A dose escalation study determined that that the high dose of 60 mg/kg was well-tolerated and could be safely used for the xenograft study for all 3 test articles.

The T Lymphoblastic Leukemic Cell Line CCRF-CEM was purchased from American Type Culture Consortium (ATCC). These cells were maintained in RPMI-1640 medium supplemented with 10% of fetal bovine serum, 2 mM glutamine, and 1 mM sodium pyruvate. The cells were cultured at 37° C. in 95% air/5% $CO_2$ and 100% humidity. Medium in the culture was changed every 48 h and cells were passaged weekly.

For cell implantation to mice, cells were harvested by centrlfugation. Cell pellets were resuspended in PBS and counted using a hemacytometer and Trypan Blue dye to measure the number of viable cells in the suspension. The harvested cells were washed once with PBS and resuspended in serum-free medium at a density of $1\times10^7$ cells/100 µl.

Study Design

For this xenograft study, animals were divided into 4 groups of 10 mice each. Groups were treated with test compounds by IP Injection at 60 mg/kg with or vehicle control.

Experimental Design for the CCRF-CEM Xenograft Study

| Group | # of Mice | Treatment | Route | Regimen |
|---|---|---|---|---|
| 1 | 10 | Vehicle* control | I.P. | 5x/week |
| 2 | 10 | Compound A, 60 mg/kg | I.P. | 5x/week |

*Vehicle = DMSO/Cremophor/water (10:18:72)

Cell Implantation

Mice were inoculated with the CCRF-CEM cells (10,000,000 cells) were by tail vein injection. The cell suspensions had the tendency to form clumps. Therefore, during cell inoculation, the cell suspensions had to be mixed well before drawing into the syringe. Gauge 28 needles were used for the injection.

Assay Procedure

Test articles were dissolved in a mixture of DMSO/Cremophor/water (10:18:72) and administered to the animals in 100 µl aliquots 5× per week beginning 7 days after cells were transplanted into mice. Control dosage was performed under the same schedule.

Throughout the entire study, clinical observations were conducted daily for signs of leukemia development, including lethargy, ruffled fur, lack of responsiveness to stimuli, weight loss, and becoming moribund. On Day 21 after cell inoculation, blood samples were drawn from all groups. The white blood cells of all the blood samples were measured with a Nucleo Counter (ChemMetec, Denmark). The clinical observations were continued until animals either died spontaneously or sacrificed when they became moribund.

Compound Pharmacokinetics

Pharmacokinetic studies were conducted on compound A to assess plasma clearance and distribution in the mouse. Compound A was administered i.p. (as in the xenograft study) at 10 mg/kg. Compound A exhibited good stability in the mouse with plasma half-lives of 2.1 h Consistent with the excellent microsome stability, the compound exhibited low plasma clearance values 0.08 L/h/kg (compound A). These data indicate that drug levels in the xenograft studies were maintained above the $IC_{50}$ of the compound throughout the dosing regime.

White Blood Cell Counts in Treated and Untreated Mice

After 14 days of treatment, blood samples were taken from all the mice via orbital bleeding while mice were anesthetized using isoflurane inhalation. Approximately 100 µl of blood was taken from each mouse. The number of white blood cells was then counted by standard methods.

Results

Figure 8:
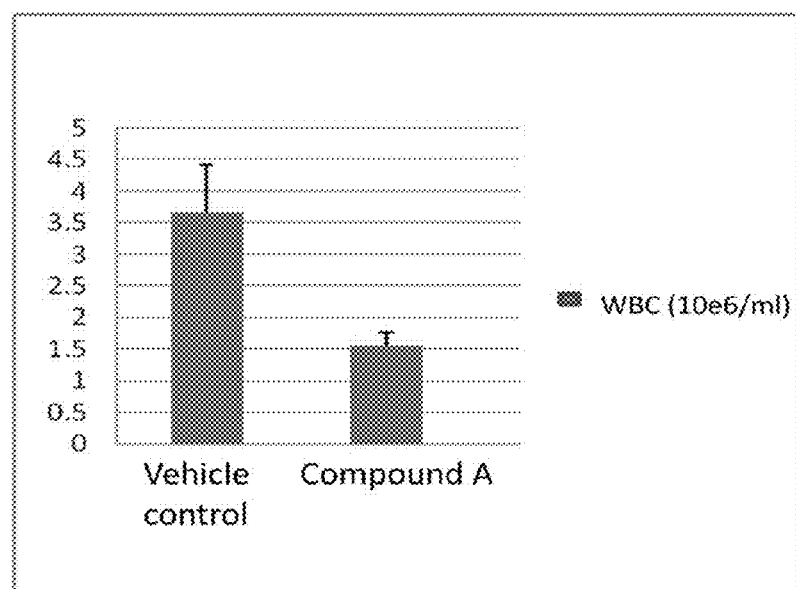
FIG. 8 is a graph summarizing the effect of compound A on white blood Cell count in a mouse human B cell leukemia mouse xenograft study.

As shown in FIG. 8, the white blood cells of mice in groups treated with compound A were significantly reduced when compared with the vehicle control group with P<0.02 (Students'"t" test).

Figure 9:
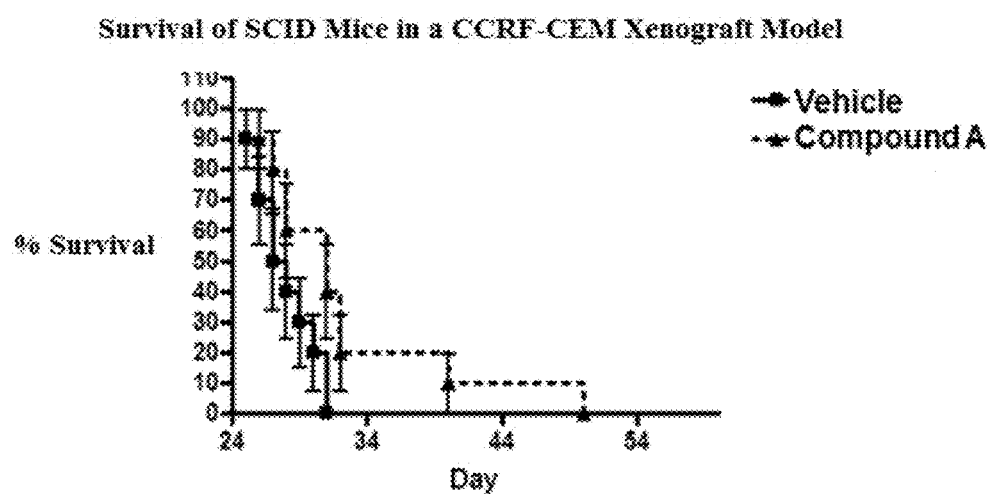
FIG. 9 is a graph summarizing the activities of compound A in a mouse human B cell leukemia (CCRF-CEM) mouse xenograft study.

During the first 20 days after the inoculation of 1×10⁷ CCRF-CEM cells via i.v. injection through the tail vein, none of the mice showed clinical signs of leukemia development. However, by day 22, 5 mice in the control group died. The survival outcome is shown in FIG. 9. Compound A was statistically significant in effecting survival outcome.

CONCLUSION

This study demonstrated that compound A has biological activity and lowered white blood cell counts and ultimately effected survival outcome significantly when compared with vehicle control as shown in FIG. 9. The reduction of white blood cells was statistically significant for test article Compound A with P<0.02 (Students'"t" test) (FIG. 8). The survival outcome of mice treated with compound A was significantly improved over the non-treated animals. On Day 21, 3 mice in the vehicle control began to develop ruffled fur and became less active. On Day 22, all 5 mice died. Beginning on Day 22, mice in each group began to show abnormal clinical signs. Animals either died spontaneously with time or became moribund. The moribund mice were sacrificed humanely in a timely manner. All mice in the vehicle control group died by Day 31, 60% of the mice in group treated with compound A were still alive on Day 31.

Pharmacokinetic studies were conducted on compound A to assess plasma clearance and distribution in the mouse. Compounds were administered i.p. (as in the xenograft study) at 19 mg/kg. Both compounds exhibit good stability in the mouse with plasma half-live of 2.1 h.). Consistent with the excellent microsome stability, compound A exhibited low plasma clearance values 0.08 L/h/kg. These data indicate that drug levels in the xenograft studies were maintained above the $IC_{50}$ of the compound throughout the dosing regime.

Oral formulations are made and tested using the Pharmatek Lab or Atories, Inc. (San Diego Calif.) Hot Rod Chemistry formulation screening kit. This kit is designed to find the correct formulation to solubilize compounds that normally have poor solubility characteristics. The kit contains eight formulations to test. Accordingly, the formulation, which imparts the best solubility, bioavailability, and stability for a lead compound is identified.

Example 9

Activity of Compound II-20 in the Fluorescence Polarization Assay Measuring Mcl-1 and Bcl-xL Inhibition The compound II-20 was assessed for ability to inhibit binding of the BH3 peptide of Bim to Mcl-1 and Bcl-xL. The activity for blocking Bim BH3 binding to both Bcl-xL and Mcl-I fusion proteins are measured and compared as in Example 2.

Materials and Methods

Experiments are performed using the fluorescence polarization assay as described in Example 2. Either GST-Bcl-xL or GST-Mcl-1 fusion proteins were titrated and maximum mp shift indicate binding concentrations for drug titration studies, as described in Example 2. Compound II-20, was titrated from 10 µM to 0.1 nM in 2-fold serial dilution into the peptide/protein solution. The $IC_{50}$ for blocking each BH3 peptide from Mcl-1 are assessed using FP, as described in Example 2.

Results

Figure 10:
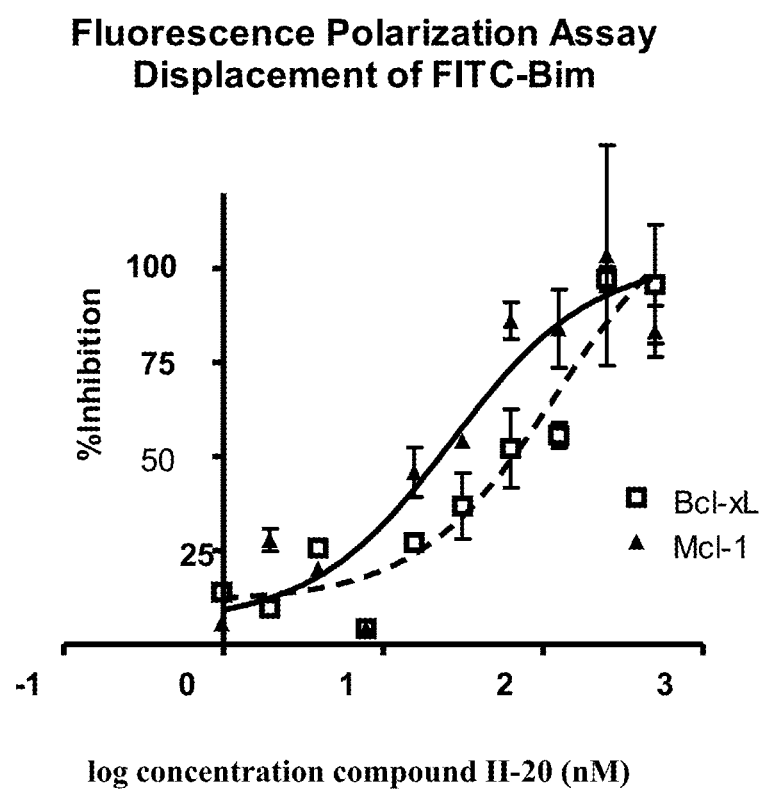
FIG. 10 is a graph, comparing the inhibition of Mcl-1 and Bcl-xL by compound II-20 in the fluorescence polarization assay described in Example 2.

Compound II-20 with a drug concentration that provokes a response halfway between baseline and maximum ($IC_{50}$) of 27 nM for Mcl-1 and 122 nM for Bcl-xL. Compound II-20 has approximately a 5-fold preference for inhibition of Mcl-1 vs. Bcl-xL as seen in FIG. 10.

Example 10

Activity of Compound II-20 in Cell Viability Assays

The ability of compound II-20 to reduce cell viability of cancer cell lines was tested in SUDHL-6 and SUDHL-10 accenting to Example 4, Compound II-20 showed activity against the SUDHL-6 cell line ($EC_{50}$=9.7 µM) but not the SUDHL-10 cell line ($EC_{50}$>25 µM), indicating that Bax and Bak are required for cell killing activity, a mode of action consistent with Mcl-1 specific inhibition.

Example 11

Pharmacokinetics of Compound II-19 Administered i.p. in Mice

Pharmacokinetic studies were conducted on compound II-19 to assess plasma clearance and distribution in male ICR mice. Compounds were administered i.p. (as in the xenograft study, Example 8) at 10 mg/kg. Blood samples were collected at various time points (pre-injection, 5 min, 15 min, 30 min, 1 h, 2 h, 4 h, 8 h and 24 h), and centrifuged to remove red blood cells. The plasma layer was recovered, and extracted with acetonitrile (equal volume) containing 1% formic acid. Plasma levels of drug were quantified by LC-MS (C18 column elided with linear gradient from 0% acetonitrile, 1% formic acid to 100% acetonitrile, 1% formic acid) against a set of standards prepared by diluting a known quantity of II-19 into mouse plasma.

Results

Figure 11:
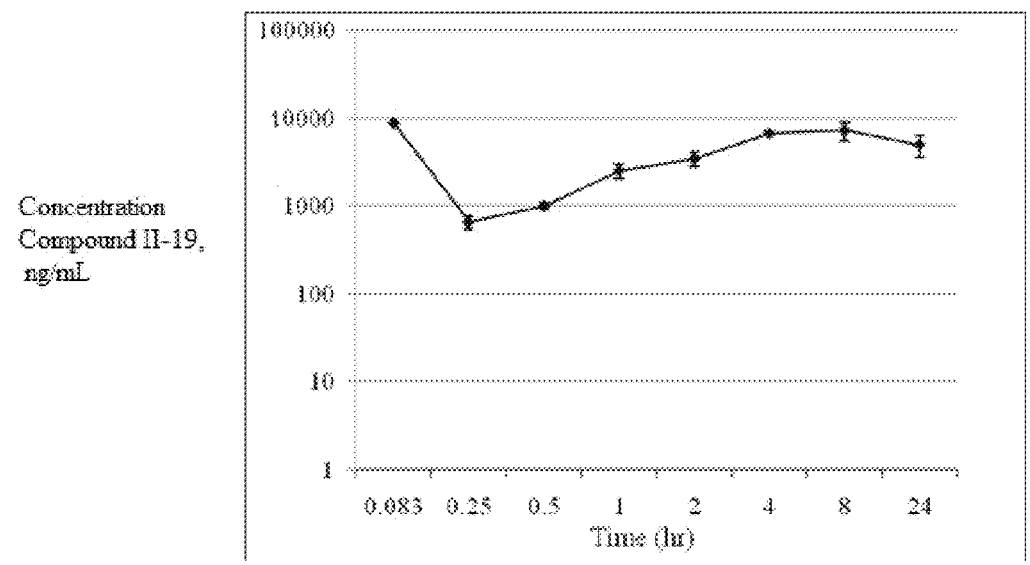
FIG. 11 is a graph of the pharmacokinetics of compound II-19 clearance in mouse plasma. Pharmacokinetic profile of Compound II-19 in. male ICR mice is shown. Compound II-19 was dissolved in 5% DMSO, 15% hydroxypropyl-beta-cyclodexmain, and 50 mM Tris in water to yield a nominal concentration of 5 mg/mL. This solution was administered intraperintoncally to 2-4 male ICR mice at a dose of 10 mg/kg. Three mice in each group were used for blood, collection, at each of 8 time points: 5 minutes, 0.25 hrs, 0.5 hrs, 1 hr, 2 hrs, 4 hrs, 8 hrs, and 24 hrs postdose. Plasma samples at these time points were analyzed for the quantity of compound II-19 by standard liquid chromatography/mass spectroscopy methods.

The compound exhibits good stability in the mouse with plasma half-live >20 h (FIG. 11). The results indicate that significant levels of circulating drug can be achieved in the mouse and that these levels can be sustained for >24 h. Significantly, the levels achieved are close to or in excess of the $EC_{50}$ observed in several cell lines (NCI H929, AML-3) for inhibition of multiple myeloma cell viability indicating that the levels of drug are potentially high enough to have a therapeutic effect against myeloma cancer cells in vivo.

Example 12

Activity of Compound II-19 in a Mouse Human Myeloma Xenograft Model

Efficacy Study

Cell Culture: Tumor cell line NCI H929 was cultured according to ATCC recommendations in RPMI8226 media containing 10% fetal bovine serum and pen-strep. On the day of implantation, cells were washed 1× with phosphate buffered saline (PBS) and harvested via centrifugation. Cells were pelleted (5 min at 1000 rpm, RT) then resuspended in serum-free matrigel and kept on ice until implantation.

Tumor Cell Implantation: The cell line was implanted via subcutaneous injection on the right rear flank at a volume of 200 µl containing 3×10^7 cells per mouse; the injection site was cleaned using alcohol before and after injection to prevent any infection.

Tumor Assessment: Beginning 1 week post cell implantation all animals were weighed and tagged and tumors were measured and body weights taken 3 times weekly (length× width×height) on Monday, Wednesday, and Friday for the duration of study. Once an average tumor volume of 100-200 $mm^3$ was reached, animals were randomized and placed into 4 treatment groups of a minimum of 10 mice per group based on tumor size. Randomization was determined by tumor volume (length×width×height)/0.52 for all of the mice and average volume was calculated using a average function in Excel (Microsoft Professional).

Treatment: The study involved 4 groups of 10 animals per group. Animals in all dose groups were weighed on days of tumor measurement. All doses were administered i.p. at 10 mL/kg. The Bortezormib (1 mg/kg) group was once every 3 days for 15 days. The mice receiving vehicle and compound II-19 were dosed every second day. Compound II-19 was formulated in 1% DMSO, 10 mM Tris pH 8, 30% hydroxypropyl-beta-cyclodextrin; this vehicle was used as the "vehicle" control. Bortezomib was formulated in 30% propylene glycol, 5% Tween 80, 3.3% dextrose in water, pH 4, 1% DMSO.

Results

Figure 12:
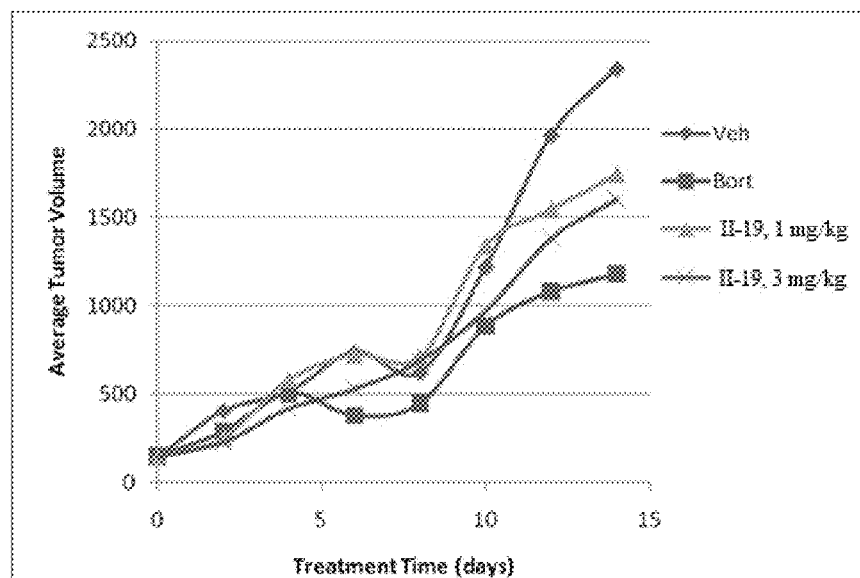
FIG. 12 is a graph, showing the effect of compound II-19 on the growth of tumors derived from the myeloma cell hue NCI H929 in a mouse human myeloma xenograft model. Activity of compound II-19 is compared to vehicle and to a dose of bortezomib known to show maximal activity.

Animals treated with both the 1 mg/kg cod and 3 mg/kg eod doses of compound II-19 exhibited a lower tumor burden than animals treated with vehicle (FIG. 12). At the end of the study, vehicle treated animals had on average a tumor size of 2300 $mm^3$ which was reduced in the 1 mg/kg and 3 mg/kg compound II-19 treated animals to 1740 $mm^3$ and 1600 $mm^3$, respectively. Tumor volume in the bortezomib treated animals was also reduced compared to vehicle with an average volume of 1180 $mm^3$. The results indicate that compound II-19 exhibits anti-tumor activity in vivo against multiple myeloma cancer cells that inhibit tumor growth and disease progression.

Example 13

Summary Structure-activity Results for Derivatives of Compound A

In addition to compound A (see example 2), compound II-19 (see Example 3) and compound II-20 (see Example 9), compounds Ic-1, Ic-6, Ic-7, Ic-8, Ic-17, and Ic-18 were tested for their ability to inhibit MCL1 by the fluorescent polarisation assay described in Example 2 and Example 3. These compounds inhibited MCL1 with IC50 values of <50 µM.

Equivalents

Those skilled in the art will recognize, or be able to ascertain, using no more than routine experimentation, numerous equivalents to the specific embodiments described specifically herein. Such equivalents are intended, to be encompassed in the scope of the following claims.

---

What is claimed is:

1. A method for inhibiting myeloid cell leukemia 1 activity in a patient having cancer, comprising administering to said patient a compound of Formula II:

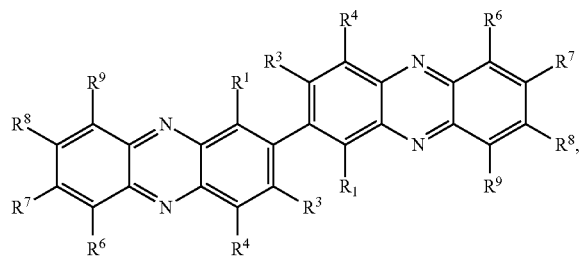

or a stereoisomer, tautomer, or pharmaceutically acceptable salt thereof, wherein:

$R^1$, $R^3$, and $R^6$ are each hydroxy;
$R^7$ and $R^8$ are each hydrogen;
$R^4$ and $R^9$ are each selected from the group consisting of hydrogen, hydroxy, —($C_1$-$C_6$) alkyl, —($C_1$-$C_6$)alkylhydroxy, —($C_1$-$C_6$)alkylamino, —($C_1$-$C_6$)alkylamido, —O($C_1$-$C_6$)alkylhalo, —OC(O)($C_1$-$C_6$)alkyl, halo, —C(O)R, —C(O)N(R)$_2$, and —C(O)OR;

where each R is independently selected from the group consisting of hydrogen, straight or branched $C_{1-10}$ alkyl, $C_{2-10}$ alkenyl, or $C_{2-10}$ alkynyl, $C_{3-10}$ cycloalkyl, $C_{5-8}$ cycloalkenyl, $C_{7-20}$ arylalkyl, saturated or unsaturated 3-11 member heterocyclyl or heterocyclylalkyl containing 1, 2, 3, or 4 heteroatoms selected independently from N, O, and S.

2. The method of claim 1, wherein the cancer is a hematopoietic cancer.

3. The method of claim 2, wherein the hematopoietic cancer is selected from the group consisting of multiple myeloma, B-cell lymphoma, T-cell lymphoma, chronic lymphocytic leukemia, acute myelogenous leukemia, acute lymphoblastic leukemia, chronic myelogenous leukemia, acute monocytic leukemia, Burkitt's lymphoma, Hodgkin's lymphoma, and Non-Hodgkin's lymphoma.

4. The method of claim 3, wherein the non-Hodgkin's lymphoma is selected from the group consisting of diffuse large B-cell lymphoma, follicular lymphoma, mantle cell lymphoma, and marginal zone lymphoma.

5. The method of claim 1, wherein the patient is also administered a 26S proteosome inhibitor.

6. The method of claim 5, wherein the 26S proteosome inhibitor is bortezomib.

7. The method of claim 6, wherein the patient is also administered lenalidomide or thalidomide, or any combination thereof.

8. The method of claim 1, wherein:
$R^1$, $R^3$, and $R^6$ are each hydroxy;
$R^7$ and $R^8$ are each hydrogen;
$R^4$ is —($C_1$-$C_6$)alkylhydroxy; and
$R^9$ is —C(O)OR, where R is selected from the group consisting of hydrogen, straight or branched $C_{1-10}$ alkyl, $C_{2-10}$ alkenyl, or $C_{2-10}$ alkynyl, $C_{3-10}$ cycloalkyl, $C_{5-8}$ cycloalkenyl, $C_{7-20}$ arylalkyl, saturated or unsaturated 3-11 member heterocyclyl or heterocyclylalkyl containing 1, 2, 3, or 4 heteroatoms selected independently from N, O, and S.

9. The method of claim 8, wherein $R^4$ is $CH_2OH$.

10. The method of claim 1, wherein the compound of Formula II is selected from the group consisting of:
dimethyl 4,4'-diformyl-1,1',3,3',6,6'-hexahydroxy-[2,2'-biphenazine]-9,9'-dicarboxylate;
dimethyl 1,1',3,3',6,6'-hexahydroxy-4,4'-bis(hydroxymethyl)-[2,2'-biphenazine]-9,9'-dicarboxylate;
dimethyl 1,1',3,3',6,6'-hexahydroxy-[2,2'-biphenazine]-9,9'-dicarboxylate;
1,1',3,3',6,6'-hexahydroxy-[2,2'-biphenazine]-9,9'-dicarboxylic acid;
1,1'-(1,1',3,3',6,6'-hexahydroxy-[2,2'-biphenazine]-9,9'-diyl)diethanone;
9,9'-bis(1-hydroxyethyl)-[2,2'-biphenazine]-1,1',3,3',6,6'-hexaol;
9,9'-bis(2-hydroxypropan-2-yl)-[2,2'-biphenazine]-1,1',3,3',6,6'-hexaol;
9,9'-diisopropyl-[2,2'-biphenazine]-1,1',3,3',6,6'-hexaol;
[2,2'biphenazine]-1,1',3,3',6,6'-hexaol;
dimethyl 4,4'-bis((dimethylamino)methyl)-1,1',3,3',6,6'-hexahydroxy-[2,2'-biphenazine]-9,9'-dicarboxylate;
dimethyl 4,4'-bis((benzylamino)methyl)-1,1',3,3',6,6'-hexahydroxy-[2,2'biphenazine]-9,9'-dicarboxylate;
dimethyl 1,1',3,3',6,6'-hexahydroxy-4,4'-bis((methylamino)methyl)-[2,2'-biphenazine]-9,9'-dicarboxylate
dimethyl 1,1',3,3',6,6'-hexahydroxy-4,4'-bis((isopropylamino)methyl)-[2,2'-biphenazine]-9,9'-dicarboxylate;
dimethyl 1,1',3,3',6,6'-hexahydroxy-4,4'-bis((phenylamino)methyl)-[2,2'-biphenazine]-9,9'-dicarboxylate;
dimethyl 1,1',3,3',6,6'-hexahydroxy-4,4'-bis(pyrrolidin-1-yl-methyl)-[2,2'-biphenazine]-9,9'-dicarboxylate;
dimethyl 4,4'-bis(((cyclopropylmethyl)amino)methyl-1,1',3,3',6,6'-hexahydroxy-[2,2'-biphenazine]-9,9'-dicarboxylate;
dimethyl 1,1',3,3',6,6'-hexahydroxy-[2,2'-biphenazine]-9,9'-dicarboxylate;
dimethyl 4,4'-bis(aminomethyl)-1,1',3,3',6,6'-hexahydroxy-[2,2'-biphenazine]-9,9'-dicarboxylate;
dimethyl 4,4'-bis(acetamidomethyl)-1,1',3,3',6,6'-hexahydroxy-[2,2'-biphenazine]-9,9'-dicarboxylate;
dimethyl 4,4'-bis (benzamidomethyl)-1,1',3,3',6,6'-hexahydroxy-[2,2'-biphenazine]-9,9'-dicarboxylate;
N9,N9'-dibenzyl-1,1',3,3',6,6'-hexahydroxy-4,4'-bis(hydroxymethyl)-[2,2'-biphenazine]-9,9'-dicarboxamid;
1,1',3,3',6,6'-hexahydroxy-4,4'-bis(hydroxymethyl)-N9,N9'-bis(2phenylpropyl)-[2,2'-biphenazine]-9,9'-dicarboxylate;
1,1',3,3',6,6'-hexahydroxy-4,4'-bis(hydroxymethyl)-N9,N9'-diisobutyl-[2,2'-biphenazine]-9,9'-dicarboxylate;
1,1',3,3',6,6'-hexahydroxy-4,4'-bis(hydroxymethyl)-N9,N9'-diisopropyl-[2,2'-biphenazine]-9,9'-dicarboxylate; and
1,1',3,3',6,6'-hexahydroxy-4,4'-bis(hydroxymethyl)-N9,N9'-dimethyl-[2,2'-biphenazine]-9,9'-dicarboxylate.

11. A method for inhibiting myeloid cell leukemia 1 activity in a patient having cancer, comprising administering to said patient a compound of Formula II, wherein the compound of Formula II is dimethyl 4,4'-diformyl-1,1',3,3',6,6'-hexahydroxy-[2,2'-biphenazine]-9,9'-dicarboxylate or dimethyl 1,1',3,3',6,6'-hexahydroxy-4,4'-bis(hydroxymethyl)-[2,2'-biphenazine]-9,9'-dicarboxylate, or a stereoisomer, tautomer, or pharmaceutically acceptable salt thereof.

12. The method of claim 11, wherein the cancer is a hematopoietic cancer.

13. The method of claim 12, wherein the hematopoietic cancer is selected from the group consisting of multiple myeloma, B-cell lymphoma, T-cell lymphoma, chronic lymphocytic leukemia, acute myelogenous leukemia, acute lymphoblastic leukemia, chronic myelogenous leukemia, acute monocytic leukemia, Burkitt's lymphoma, Hodgkin's lymphoma, non-Hodgkin's lymphoma.

14. The method of claim 13, wherein the non-Hodkin's lymphoma is selected from the group consisting of diffuse large B-cell lymphoma, follicular lymphoma, mantle cell lymphoma, and marginal zone lymphoma.

15. A method for inhibiting B-cell lymphoma-extra large activity in a patient having an autoimmune disease, comprising administering to said patient a compound of Formula II:

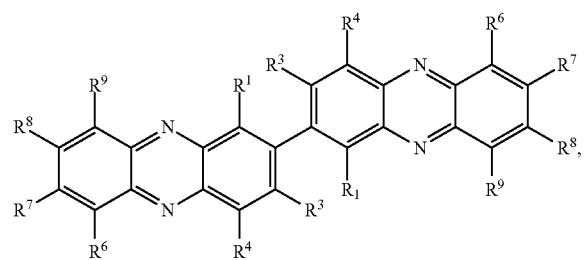

or a stereoisomer, tautomer, or pharmaceutically acceptable salt thereof, wherein:
$R^1$, $R^3$, and $R^6$ are each hydroxy;
$R^7$ and $R^8$ are each hydrogen;
$R^4$ and $R^9$ are each selected from the group consisting of hydrogen, hydroxyl, —($C_1$-$C_6$) alkyl, —($C_1$-$C_6$)alkylhydroxy, —($C_1$-$C_6$)alkylamino, —($C_1$-$C_6$)alkylamido, —O($C_1$-$C_6$)alkylhalo, —OC(O)($C_1$-$C_6$)alkyl, halo, —C(O)R, —C(O)N(R)$_2$ and —C(O)OR;
where each R is independently selected from, the group consisting of hydrogen, straight or branched $C_{1-10}$ alkyl, $C_{2-10}$ alkenyl, or $C_{2-10}$ alkynyl, $C_{3-10}$ cycloalkyl, $C_{5-8}$ cycloalkenyl, $C_{7-20}$ arylalkyl, saturated or unsaturated 3-11 member heterocyclyl or heterocyclylalkyl containing 1, 2, 3, or 4 heteroatoms selected independently from N, O, and S.

16. The method of claim 15, wherein the autoimmune disease is selected from the group consisting of rheumatoid arthritis, osteo arthritis, psoriatic arthritis, psoriasis, neuromyaotonia, mayasthenia gravis, lupus erythematosus, endometriosis, Graves'disease, granulomatosis, Crohn's disease, interstitial cystitis, uveitis, and multiple sclerosis.

17. The method of claim 15, wherein:
$R^1$, $R^3$, and $R^6$ are each hydroxy;
$R^7$ and $R^8$ are each hydrogen;
$R^4$ is —($C_1$-$C_6$)alkylhydroxy; and
$R^9$ is —C(O)OR, where R is selected from the group consisting of hydrogen, straight or branched $C_{1-10}$ alkyl, $C_{2-10}$ alkenyl, or $C_{2-10}$ alkynyl, $C_{3-10}$ cycloalkyl, $C_{5-8}$ cycloalkenyl, $C_{7-20}$ arylalkyl, saturated or unsaturated 3-11 member heterocyclyl or heterocyclylalkyl containing 1, 2, 3, or 4 heteroatoms selected independently from N, O, and S.

18. The method of claim 17, wherein $R^4$ is $CH_2OH$.

19. The method of claim 1, wherein the compound of Formula II is dimethyl 4,4'-diformyl-1,1',3,3',6,6'-hexahydroxy-[2,2'-biphenazine]-9,9'-dicarboxylate or dimethyl 1,1',3,3',6,6'-hexahydroxy-4,4'-bis(hydroxymethyl)-[2,2'-biphenazine]-9,9'-dicarboxylate, or a stereoisomer, tautomer, or pharmaceutically acceptable salt thereof.

20. The method of claim 15, wherein the compound of Formula II is selected from the group consisting of:
dimethyl 4,4'-diformyl-1,1',3,3',6,6'-hexahydroxy-[2,2'-biphenazine]-9,9'-dicarboxylate;
dimethyl 1,1',3,3',6,6'-hexahydroxy-4,4'-bis(hydroxymethyl)-[2,2'-biphenazine]-9,9'-dicarboxylate;
dimethyl 1,1',3,3',6,6'-hexahydroxy-[2,2'-biphenazine]-9,9'-dicarboxylate;
1,1',3,3',6,6'-hexahydroxy-[2,2'biphenazine]-9,9'-dicarboxylic acid;
1,1'-(1,1',3,3',6,6'-hexahydroxy-[2,2'-biphenazine]-9,9'-diyl)diethanone;
9,9'-bis(1-hydroxyethyl)-[2,2'-biphenazine]-1,1',3,3',6,6'-hexaol;
9,9'-bis(2-hydroxypropan-2-yl)-[2,2'-biphenazine]-1,1',3,3',6,6'-hexaol;
9,9'-diisopropyl-[2,2'-biphenazine]-1,1',3,3',6,6'-hexaol;
[2,2'biphenazine]-1,1',3,3',6,6'-hexaol;
dimethyl 4,4'-bis((dimethylamino)methyl)-1,1',3,3',6,6'-hexahydroxy-[2,2'-biphenazine]-9,9'-dicarboxylate;
dimethyl 4,4'-bis((benzylamino)methyl)-1,1',3,3',6,6'-hexahydroxy-[2,2'biphenazine]-9,9'-dicarboxylate;
dimethyl 1,1',3,3',6,6'-hexahydroxy-4,4'-bis((methylamino)methyl)-[2,2'-biphenazine]-9,9'-dicarboxylate
dimethyl 1,1',3,3',6,6'-hexahydroxy-4,4'-bis((isopropylamino)methyl)-[2,2'-biphenazine]-9,9'-dicarboxylate;
dimethyl 1,1',3,3',6,6'-hexahydroxy-4,4'-bis((phenylamino)methyl)-[2,2'-biphenazine]-9,9'-dicarboxylate;
dimethyl 1,1',3,3',6,6'-hexahydroxy-4,4'-bis(pyrrolidin-1-yl-methyl)-[2,2'-biphenazine]-9,9'-dicarboxylate;
dimethyl 4,4'-bis(((cyclopropylmethyl)amino)methyl)-1,1',3,3',6,6'-hexahydroxy-[2,2'-biphenazine]-9,9'-dicarboxylate;
dimethyl 1,1',3,3',6,6'-hexahydroxy-[2,2'-biphenazine]-9,9'-dicarboxylate;
dimethyl 4,4'-bis(aminomethyl)-1,1',3,3',6,6'-hexahydroxy-[2,2'-biphenazine]-9,9'-dicarboxylate;
dimethyl 4,4'-bis(acetamidomethyl)-1,1',3,3',6,6'-hexahydroxy-[2,2'-biphenazine]-9,9'-dicarboxylate;
dimethyl 4,4'-bis(benzamidomethyl)-1,1',3,3',6,6'-hexahydroxy-[2,2'-biphenazine]-9,9'-dicarboxylate;
N9,N9'-dibenzyl-1,1',3,3',6,6'-hexahydroxy-4,4'-bis(hydroxymethyl)-[2,2'-biphenazine]-9,9'-dicarboxamide;
1,1',3,3',6,6'-hexahydroxy-4,4'-bis(hydroxymethyl)-N9,N9'-bis(2phenylpropyl)-[2,2'-biphenazine]-9,9'-dicarboxamide;
1,1',3,3',6,6'-hexahydroxy-4,4'-bis(hydroxymethyl)-N9,N9'-diisobutyl-[2,2'-biphenazine]-9,9'-dicarboxamide;
1,1',3,3',6,6'-hexahydroxy-4,4'-bis(hydroxymethyl)-N9,N9'-diisopropyl-[2,2'-biphenazine]-9,9'-dicarboxamide; and
1,1',3,3',6,6'-hexahydroxy-4,4'-bis(hydroxymethyl)-N9,N9'-dimethyl-[2,2'-biphenazine]-9,9'-dicarboxamide.

* * * * *

SEQUENCE LISTING

```
<160> NUMBER OF SEQ ID NOS: 1

<210> SEQ ID NO 1
<211> LENGTH: 18
<212> TYPE: PRT
<213> ORGANISM: Unknown
<220> FEATURE:
<223> OTHER INFORMATION: FITC labeled BH3 domain of Bim
<220> FEATURE:
<221> NAME/KEY: MISC_FEATURE
<222> LOCATION: (1)..(1)
<223> OTHER INFORMATION: May be labeled with FITC fluorophore

<400> SEQUENCE: 1
```

-continued

```
Gly Gly Gly Ile Ala Gln Glu Leu Arg Arg Ile Gly Asp Glu Phe Asn
1               5                   10                  15
Ala Tyr
```